(12) United States Patent
Corti

(10) Patent No.: US 10,047,145 B2
(45) Date of Patent: Aug. 14, 2018

(54) ANTIBODIES THAT POTENTLY NEUTRALIZE RSV AND USES THEREOF

(71) Applicant: Humabs Biomed SA, Bellinzona (CH)

(72) Inventor: Davide Corti, Bellinzona (CH)

(73) Assignee: Humabs Biomed SA, Bellinzona (CH)

( * ) Notice: Subject to any disclaimer, the term of this patent is extended or adjusted under 35 U.S.C. 154(b) by 86 days.

(21) Appl. No.: 14/911,966

(22) PCT Filed: Jul. 24, 2014

(86) PCT No.: PCT/EP2014/002027
§ 371 (c)(1),
(2) Date: Feb. 12, 2016

(87) PCT Pub. No.: WO2015/010792
PCT Pub. Date: Jan. 29, 2015

(65) Prior Publication Data
US 2016/0200802 A1    Jul. 14, 2016

Related U.S. Application Data

(60) Provisional application No. 61/857,942, filed on Jul. 24, 2013.

(51) Int. Cl.
*C07K 16/10* (2006.01)
*C07K 14/005* (2006.01)
*C12N 7/00* (2006.01)
*A61K 39/00* (2006.01)

(52) U.S. Cl.
CPC ........ *C07K 16/1027* (2013.01); *C07K 14/005* (2013.01); *C12N 7/00* (2013.01); *A61K 39/00* (2013.01); *C07K 2317/14* (2013.01); *C07K 2317/21* (2013.01); *C07K 2317/33* (2013.01); *C07K 2317/51* (2013.01); *C07K 2317/515* (2013.01); *C07K 2317/56* (2013.01); *C07K 2317/565* (2013.01); *C07K 2317/76* (2013.01); *C12N 2760/18534* (2013.01)

(58) Field of Classification Search
None
See application file for complete search history.

(56) References Cited

FOREIGN PATENT DOCUMENTS

| EP | 1997830 | * | 3/2008 |
| EP | 1997830 A1 | | 12/2008 |
| WO | 2006050280 A2 | | 5/2006 |
| WO | 2011020079 A1 | | 2/2011 |
| WO | WO2011/020078 | * | 2/2011 |

OTHER PUBLICATIONS

Rudikoff et al Proc Natl Acad Sci USA 1982 vol. 79 p. 1979.*
MacCallum et al. J. Mol. Biol. (1996) 262, 732-745.*
Casset et al. (2003) BBRC 307, 198-205.*
Corti, D., et al., "Cross-Neutralization of Four Paramyxoviruses by a Human Monoclonal Antibody", Nature, vol. 501, No. 7467, Sep. 19, 2013, pp. 439-443.
Corti, D., et al., Cross-Neutralization of Four Paramyxoviruses by a Human Monoclonal Antibody-Supplementary Information, Nature, vol. 501, No. 7467, Aug. 18, 2013. pp. 1-16.
McLellan, J. S. et al., "Structure of RSV Fusion Glycoprotein Trimer Bound to a Perfusion-Specific Neutralizing Antibody," Science, May 31, 2013, vol. 340, No. 6136, pp. 1113-1117.
Wu, H., et al., "Development of Motavizumab, an Ultra-Potent Antibody for the Prevention of Respiratory Syncytial Virus Infection in the Upper and Lower Respiratory Tract," J Mol Bio, May 4, 2007, 368, pp. 652-665.

* cited by examiner

*Primary Examiner* — Shanon A. Foley
*Assistant Examiner* — Myron G Hill
(74) *Attorney, Agent, or Firm* — Seed Intellectual Property Law Group LLP

(57) ABSTRACT

The invention relates to antibodies, and antigen binding fragments thereof, that neutralize infection of both group A and group B RSV. The invention also relates to antigenic sites to which the antibodies and antigen binding fragments bind, as well as to nucleic acids that encode and immortalized B cells and cultured plasma cells that produce such antibodies and antibody fragments. In addition, the invention relates to the use of the antibodies, antibody fragments, and polypeptides recognized by the antibodies of the invention in screening methods as well as in the diagnosis, treatment and prevention of RSV infection and group A and group B RSV co-infection.

33 Claims, 13 Drawing Sheets

HMB2435

Homsap IGHV3-30*01 F, or Homsap IGHV3-30-3*01 F (87.15%), Homsap IGHJ6*02 F (a)
(75.81%), Homsap IGHD3-10*01 F
Homsap IGLV2-14*01 F (93.75%), Homsap IGLJ2*01 F, or Homsap IGLJ3*01 F or Homsap
IGLJ3*02 F (85.29%)

VH nucleic acid sequence caggtgcagctggtggagtctggggggaggcgtggtccagcctggggaggccctcagactctcct
gtgcagcctctggattcgccttcaataattttgctttacactgggtccgccaggctccaggcaa
gggtccagagtggctggcagctgtgtcctatgacggaaccagtccatactacgcagagtccgtc
agggcccgattcagcatctccagagacaattccaagaaaacattctatctgcaattggacagcc
tgcgacctgaagacacggctgtctattactgt**gcgagagggcttggttcggggagttattcgtg
gattggttactttttatgcaatggacgtc**tggggccgagggacgacggtcaccgtctcctca

VH amino acid sequence

QVQLVESGGGVVQPGRPLRLSCAASGFAFNNFALHWVRQAPGKGPEWLAAVSYDGTSPYYAESV
RARFSISRDNSKKTFYLQLDSLRPEDTAVYYCARGLGSGSYSWIGYFYAMDVWGRGTTVTVSS

VL nucleic acid sequence cagtctgccctgactcagcctgcctccgtgtctgggtctcctggacaatcgatcaccatctcct
gcactggaaccagcagtgacgttggtggttatgtctatgtcgcctggtaccaacaacacccagg
cacagcccccaaactcatcatttatgatgtcagtgatcggccctcaggggtttctaatcgattc
tctgggtccaagtctggcaacacggcctccctgaccatctctgggctccaggctgaggacgacg
ctgattattactgcatctcgtataccgacagaaacactgtcgtttttggcggcgggaccaagtt
gaccgtcctg

VL amino acid sequence

QSALTQPASVSGSPGQSITISCTGTSSDVGGYVYVAWYQQHPGTAPKLIIYDVSDRPSGVSNRF
SGSKSGNTASLTISGLQAEDDADYYCISYTDRNTVVFGGGTKLTVL

FIGURE 7

HMB2437

Homsap IGHV2-26*01 F (95.19%), Homsap IGHJ6*02 F (83.87%), Homsap IGHD5-24*01 ORF
Homsap IGKV1-39*01 F, or Homsap IGKV1D-39*01 F (91.40%), Homsap IGKJ5*01 F (97.37%)

VH nucleic acid sequence caggtcaccttgaaggagtctggtcctgtgctggtgaaacccctcagagacccctcacgctgacct
gcaccgtctctggattctcactcacagatgctagaatgggtgtgagttggatccgtcagccccc
agggaaggccctggagtggcttgcacacattttctcgaatgacgaaaaattctacagcacatct
ctgaagaccaggctcaccatctccaaggacacctccacaagccaggtggtccttaggatgacca
acatggaccctgtggacacagccacttattattgt**gcacgagtcgatcagggatgggtaaacac
gtacagcgccttttattatggtatggacttc**tggggccaagggaccacggtcaccgtctcctca

VH amino acid sequence

QVTLKESGPVLVKPSETLTLTCTVSGFSLTDARMGVSWIRQPPGKALEWLAHIFSNDEKFYSTS
LKTRLTISKDTSTSQVVLRMTNMDPVDTATYYCARVDQGWVNTYSAFYYGMDFWGQGTTVTVSS

VK nucleic acid sequence gacatccagatgacccagtctccatcctccctgtctgcatctgtaggagaaagagtcaccatca
cttgccgggcaagtcagtacattagcacccatttaaattggtatcagcacaaaccagggaaagc
ccctcgtctcctgatctatggtgcctcccatttggaaggtggggacccatcacggttcagtggc
agtggatctgggacagatttcagtctcaccattaccagtctgcaacctgaagattttgcaactt
actactgtcaacagacttataaaccccgatcaccttcgcccaagggacacgactggagattaa
a

VK amino acid sequence

DIQMTQSPSSLSASVGERVTITCRASQYISTHLNWYQHKPGKAPRLLIYGASHLEGGDPSRFSG
SGSGTDFSLTITSLQPEDFATYYCQQTYKTPITFAQGTRLEIK

FIGURE 8

HMB2416

IGHV4-30-4*01 (96.22%), IGHJ4*02 (89.58%), IGHD5-5*01
IGLV3-21*01 (93.55%), IGLJ2*01, or IGLJ3*01 (97.37%)

VH nucleic acid sequence caggtgcagctgcaggagtcgggcccaggactcgtgaagccttcacagaccctgtccctcacct
gcactgtctctggtggctccatcagcagtggtgattactactggagttggatccgccagcccc
agggaagggcctggagtggattgggtacatctacttcagtggcagcacctactacaatccgtcc
ctcaagagtcgagttaccatgtcaggggacacgtccaagaatcagttctccctgaggctgagct
ctgtgactgccgcagacacggccgtgtattattgt**gccagagaggatacaactatggctattcc
atactacttcgacccc**tggggccggggaatcctggtcaccgtctcctca

VH amino acid sequence

QVQLQESGPGLVKPSQTLSLTCTVSGGSISSGDYYWSWIRQPPGKGLEWIGYIYFSGSTYYNPS
LKSRVTMSGDTSKNQFSLRLSSVTAADTAVYYCAREDTTMAIPYYFDPWGRGILVTVSS

VL nucleic acid sequence tcctatgtcctgactcagccaccctcagtgtcagtggcccccggaaggacggccaggatcacct
gtgggagacataatattggaaatgaaaatgttcactggtaccagcagaggccaggccaggcccc
tgtgctggtcatctattctgatagcgaccggccctcagggatccctgagcgattctctggctcc
aactctgggaacacggccaccctaagcatcagcagggtcgaagccggggatgaggccgactatt
attgtcaggtgtgggatagtagtactgatcaagtggtattcggcggagggaccaagctgaccgt
cctag

VL amino acid sequence

SYVLTQPPSVSVAPGRTARITCGRHNIGNENVHWYQQRPGQAPVLVIYSDSDRPSGIPERFSGS
NSGNTATLSISRVEAGDEADYYCQVWDSSTDQVVFGGGTKLTVL

FIGURE 9

HMB2432

Homsap IGHV5-51*01 F (92.01%), Homsap IGHJ6*02 F (a) (90.32%), Homsap IGHD2-15*01 F
Homsap IGKV1-39*01 F, or Homsap IGKV1D-39*01 F (91.76%), Homsap IGKJ1*01 F (97.22%)

VH.1 nucleic acid sequence gaggtgcagctggtgcagtctggagcggaggtgaaaaaacccggggacgtctctgaagatctcct
gcaagggttctggatttagttttagcaactattggatcggctgggtgcgccagatgcccgggaa
aggcctggagtggatggggatcgtctatccggctgactctgacaccagatacagcccgtccttc
cagggccaggtcaccatctcaggcgacaactccatcaataccgcctacctgcagtggagccgcc
tgaaggcctcggacaccgccacctattactgt**gtgagacaaatcggggggggtggtgacaactgc
tactgacgactacttctacggtatggacatc**tggggcccagggaccacggtcatcgtctcctca

VH.1 amino acid sequence

EVQLVQSGAEVKKPGTSLKISCKGSGFSFSNYWIGWVRQMPGKGLEWMGIVYPADSDTRYSPSF
QGQVTISGDNSINTAYLQWSRLKASDTATYYCVRQIGGVVTTATDDYFYGMDIWGPGTTVIVSS

VH.2 nucleic acid sequence gaggtgcagctggtgcagtctggagcggaggtgaaaaaacccggggacgtctctgaagatctcct
gcaagggttctggatttagttttagcaactattggatcggctgggtgcgccagatgcccgggaa
aggcctggagtggatggggatcgtctatccggctgactctgacaccagatacagcccgtccttc
cagggccaggtcaccatctcaggcgacaactccatcaataccgcctacctgcagtggagccgcc
tgaaggcctcggacaccgccacctattactgt**gtgagacaaatcggggggggtggtgacaactgc
tactgacgactacttctacggtatggacatc**tggggcccagggaccacggtcaccgtctcctca

VH.2 amino acid sequence

EVQLVQSGAEVKKPGTSLKISCKGSGFSFSNYWIGWVRQMPGKGLEWMGIVYPADSDTRYSPSF
QGQVTISGDNSINTAYLQWSRLKASDTATYYCVRQIGGVVTTATDDYFYGMDIWGPGTTVTVSS

FIGURE 10A

HMB2432

<u>Homsap IGHV5-51*01 F</u> (92.01%), <u>Homsap IGHJ6*02 F (a)</u> (90.32%), <u>Homsap IGHD2-15*01 F</u>
<u>Homsap IGKV1-39*01 F, or Homsap IGKV1D-39*01 F</u> (91.76%), <u>Homsap IGKJ1*01 F</u> (97.22%)

<u>VK.1 nucleic acid sequence</u> gaaacgacactcacgcagtctccatcctccctgtctgcatctgtaggagacagagtcaccatca
cttgccgggcaagtcagaccgttaaaagctttttaaattggtatcagcagaagccagggaaagc
cctaaactcctgatctatgatgcatccgatttgcaaagtggggtcccatccaggttcagtggc
agtggatctgggacagatttcactctcaccatcagccgtctgcaacctgaagatttgcaactt
acttctgtcaacagagttacaggaccctctgacgttcggccaagggaccagggtggaaatcaa
a <u>VK.1 amino acid sequence</u>

ETTLTQSPSSLSASVGDRVTITCRASQTVKSFLNWYQQKPGKAPKLLIYDASDLQSGVPSRFSG
SGSGTDFTLTISRLQPEDFATYFCQQSYRTPLTFGQGTRVEIK

<u>VK.2 nucleic acid sequence</u> gaaacgacactcacgcagtctccatcctccctgtctgcatctgtaggagacagagtcaccatca
cttgccgggcaagtcagaccgttaaaagctttttaaattggtatcagcagaagccagggaaagc
cctaaactcctgatctatgatgcatccgatttgcaaagtggggtcccatccaggttcagtggc
agtggatctgggacagatttcactctcaccatcagccgtctgcaacctgaagatttgcaactt
acttctgtcaacagagttacaggaccctctgacgttcggccaagggaccaaggtggaaatcaa
a <u>VK.2 amino acid sequence</u>

ETTLTQSPSSLSASVGDRVTITCRASQTVKSFLNWYQQKPGKAPKLLIYDASDLQSGVPSRFSG
SGSGTDFTLTISRLQPEDFATYFCQQSYRTPLTFGQGTKVEIK

FIGURE 10B

| | | |
|---|---|---|
| HMB2435 heavy chain | QVQLVESGGGVVQPGRPLRLSCAASgfafnnfaLHWVRQAPGKGPEWLAAvsydgispYYAESVR | 65 |
| HMB2435 FR-GL heavy chain | ................S.........................M..........L..V..V.........D..K | 65 |
| HMB2435 heavy chain | ARFSISRDNSKKTFYLQLDSLRPEDTAVYYCargigsgsyswigyfyamdvWGRGTTVTVSS | 127 |
| HMB2435 FR-GL heavy chain | G...T........N.L...MN....A...........................Q....... | 127 |
| HMB2435 light chain | QSALTQPASVSGSPGQSITISCTGTSsdvggyyyVAWYQQHPGTAPKLIIYdvSDRPSGVSNRFS | 65 |
| HMB2435 FR-GL light chain | ................................S..............K....M....N... | 65 |
| HMB2435 light chain | GSKSGNTASLTISGLQAEDDADYYCIsyIdrnIvvFGGGTKLTVL | 110 |
| HMB2435 FR-GL light chain | .....................E..................... | 110 |
| HMB2437 heavy chain | QVTLKESGPVLVKPSETLTLTCTVSgfsIIdarmgVSWIRQPPGKALEWLAHIfsndekFYSTSL | 65 |
| HMB2437 FR-GL heavy chain | ........................T................................S... | 65 |
| HMB2437 heavy chain | KTRLTISKDTSTSQVVLRMTNMDPVDTATYYCarvdqgwvntysafygmdfWGQGTTVTVSS | 128 |
| HMB2437 FR-GL heavy chain | .S................K.....T................................... | 128 |
| HMB2437 light chain | DIQMTQSPSSLSASVGERVTITCRASqyIsthLNWYQHKPGKAPRLLIYgashLEGGDPSRFSGS | 65 |
| HMB2437 FR-GL light chain | ..................D............Q......K.......S..QS..V........ | 65 |
| HMB2437 light chain | GSGTDFSLTITSLQPEDFATYYCqqtykIpItFAQGTRLEIK | 107 |
| HMB2437 FR-GL light chain | ..T...S...............G.................. | 107 |

ANTIBODIES THAT POTENTLY NEUTRALIZE RSV AND USES THEREOF

BACKGROUND

The invention relates to antibodies, and antigen binding fragments thereof, that neutralize infection of both group A and group B Respiratory Syncytial Virus (RSV). The invention also relates to antigenic sites to which the antibodies and antigen binding fragments bind, as well as to nucleic acids that encode and immortalized B cells and cultured plasma cells that produce such antibodies and antibody fragments. In addition, the invention relates to the use of the antibodies, antibody fragments, and polypeptides recognized by the antibodies of the invention in screening methods as well as in the diagnosis, treatment and prevention of RSV infection and group A and group B RSV co-infection.

Respiratory Syncytial Virus (RSV) is a common cold virus that belongs to the family of paramixoviruses. The virion of RSV is enveloped with a lipid bilayer, which contains glycoproteins including the attachment protein G and the fusion protein F. RSV strains are separated into two major groups (A and B) on the basis of antigenic and genetic variability. The amino acid sequences of the G and F proteins of RSV are classified into A and B groups. The F protein of RSV is a type I trans-membrane surface protein that has an N-terminal cleaved signal peptide and a membrane anchor near the C-terminus. The F protein is synthesized as an inactive F0 precursor that assembles into homotrimers and is activated by cleavage. The F protein is formed by three domains (DI to DIII), a fusion peptide (FP) and three heptad-repeats regions (HR-A, -B and -C). The F glycoprotein of RSV directs viral penetration by fusion between the virion envelope and the host cell plasma membrane. The N-terminus of the F subunit, that is created by proteolytic cleavage and contains the fusion peptide, inserts directly into the target membrane to initiate fusion. After binding to the target cell and subsequent activation, the metastable pre-fusion F protein undergoes a series of structural rearrangements that result in the insertion of the fusion peptide into the target cell membrane, followed by the formation of a stable helical bundle that forms as the viral and cell membranes are apposed. These structural changes lead to the formation of a stable post-fusion F protein. Later in infection, the F protein expressed on the cell surface of infected cells can mediate fusion with adjacent non-infected cells forming large syncytia.

Respiratory Syncytial Virus (RSV) is the most common cause of lower respiratory tract disease in children less than two years. It is also the cause of severe disease in premature newborns, hospitalized children (Hall, C. B. et al., 2009, *N Engl J Med* 360, 588-598), immune-compromised patients (Falsey, A. R. et al., 2005, *N Engl J Med* 352, 1749-1759), and patients with chronic lung disease and congenital heart disease. RSV plays a role in acute asthma exacerbations (Edwards, M. R. et al., 2012, *Nat Rev Immunol* 10, 459-471) and is also a cause of acute respiratory tract illness in lung transplant recipients leading to increased risk of chronic rejection.

Immunocompromised patients have a 5% to 15% rate of RSV infection and the progression to low respiratory tract infection (LRTI) is observed in 38% of these patients with an average mortality of 32%. There is no effective treatments to prevent the spread of the virus or to control LRTI. Ribavirin and IVIG have been used with limited success. Immunity to RSV appears to be short-lived, and thus re-infections are frequent (Ogra, 2003, *Paediatric Respiratory Reviews* 5 Suppl A:S119-126).

Vaccines for RSV infection are currently not available. A formalin-inactivated and alum-adjuvanted RSV vaccine (FI-RSV) tested in the 1960s was found to predispose infants for enhanced disease following natural RSV infection leading to high fever and severe pneumonia, resulting in high hospitalization rates and even some fatalities (Fulginiti et al., 1969, *American Journal of Epidemiology* 89:435-448; Kapikian et al., 1969, *American Journal of Epidemiology* 89:405-421; Kim et al., 1969, *American Journal of Epidemiology* 89:422-434).

Evidence for the role of serum antibodies in protection against RSV virus has emerged from epidemiological as well as animal studies. In infants, titers of maternally transmitted antibodies correlate with resistance to serious disease (Glezen et al., 1981, *The Journal of Pediatrics* 98:708-715) and in adults incidence and severity of lower respiratory tract involvement is diminished in the presence of high levels of serum RSV neutralizing antibodies (McIntosh et al., 1978, *The Journal of Infectious Diseases* 138: 24-32).

A monoclonal antibody, palivizumab (SYNAGIS®), is registered for the prevention of RSV infection in premature newborns. In addition to palivizumab, other monoclonal antibodies shown to neutralize RSV infection, such as 101F and D25, as disclosed in EP 1 997 830 A1, have also been described. The antibody registered for the prevention of RSV infection, palivizumab, is, however, not potent and the response to palivizumab is varied among individuals. Further, it fails to prevent RSV infections effectively in some cases (Weisman, L. E., 2005, *Curr. Opin. Mol. Ther.* 11, 208-218) and prolonged pulmonary replication of RSV in the presence of palivizumab is followed in animals by the appearance of resistant virus strains (Zhao and Sullender, 2005, *Journal of Virology* 79:3962-3968).

Accordingly, there is still a need for agents capable of preventing as well as treating or attenuating RSV infection in high-risk patients with high potency and efficacy. Further, it is important to have antibodies that target different epitopes and different antigenic sites on the various strains in order to avoid appearance of resistant virus strains.

SUMMARY

The objectives described above are solved by the present invention, preferably by the subject-matter of the appended claims.

The invention is based, in part, on the discovery of antibodies that potently neutralize infection of RSV, as well as antigenic sites and epitopes to which the antibodies of the invention bind. Accordingly, in one aspect of the invention, the invention comprises an isolated antibody, for example a monoclonal antibody, a human antibody, a human monoclonal antibody, an antibody variant, or an antigen binding fragment, that neutralizes infection of RSV.

More specifically, the present invention comprises an isolated antibody, or an antigen binding fragment thereof, that neutralizes infection of both group A RSV and group B RSV, but does preferably not neutralize infection of MPV, wherein preferably the antibody or the antigen binding fragment specifically binds the pre-fusion F protein of RSV, but not the post-fusion RSV F protein. Preferably, the antibody or the antigen binding fragment has an isoelectric point (pI) of 7.5 or higher. Preferably, the antibody or the antigen binding fragment does not specifically bind to the pre-fusion F protein of RSV at antigenic site S1 and/or does not bind to the pre-fusion F protein of RSV at antigenic site S1, respectively. Preferably, the antibody or the antigen binding fragment specifically binds to antigenic site S2, antigenic site S3, antigenic site S5 or a site in between antigenic sites S2 and S3 on the pre-fusion F protein of RSV. Preferably, the concentration of the antibody or the antigen binding fragment thereof required for 50% neutralization of RSV is 150 ng/ml or less.

It is moreover preferred that the antibody, or the antigen binding fragment thereof, comprises a heavy chain comprising CDRH1, CDRH2 and CDRH3 and a light chain comprising CDRL1, CDRL2 and CDRL3, wherein the heavy chain CDRH3 comprises an amino acid sequence that is at least 90% identical to SEQ ID NOs: 3, 19, 35 or 51. More preferably, the heavy chain CDRH3 of the antibody, or of the antigen binding fragment thereof, comprises the amino acid sequence of SEQ ID NOs: 3, 19, 35 or 51.

Preferably, the antibody, or the antigen binding fragment thereof, comprises: (i) heavy chain CDRH1, CDRH2, and CDRH3 amino acid sequences and light chain CDRL1, CDRL2, and CDRL3 amino acid sequences that are at least 90% identical to the amino acid sequences of SEQ ID NOs: 1-6, respectively; (ii) heavy chain CDRH1, CDRH2, and CDRH3 amino acid sequences and light chain CDRL1, CDRL2, and CDRL3 amino acid sequences that are at least 90% identical to the amino acid sequences of SEQ ID NOs: 17-22, respectively; (iii) heavy chain CDRH1, CDRH2, and CDRH3 amino acid sequences and light chain CDRL1, CDRL2, and CDRL3 amino acid sequences that are at least 90% identical to the amino acid sequences of SEQ ID NOs: 33-38, respectively; or (iv) heavy chain CDRH1, CDRH2, and CDRH3 amino acid sequences and light chain CDRL1, CDRL2, and CDRL3 amino acid sequences that are at least 90% identical to the amino acid sequences of SEQ ID NOs: 49-54, respectively. More preferably, the antibody or the antigen binding fragment comprises: (i) heavy chain CDRH1, CDRH2, and CDRH3 amino acid sequences and light chain CDRL1, CDRL2, and CDRL3 amino acid sequences as set forth in SEQ ID NOs: 1-6, respectively; (ii) heavy chain CDRH1, CDRH2, and CDRH3 amino acid sequences and light chain CDRL1, CDRL2, and CDRL3 amino acid sequences as set forth in SEQ ID NOs: 17-22, respectively; (iii) heavy chain CDRH1, CDRH2, and CDRH3 amino acid sequences and light chain CDRL1, CDRL2, and CDRL3 amino acid sequences as set forth in SEQ ID NOs: 33-38, respectively; or (iv) heavy chain CDRH1, CDRH2, and CDRH3 amino acid sequences and light chain CDRL1, CDRL2, and CDRL3 amino acid sequences as set forth in SEQ ID NOs: 49-54, respectively.

It is furthermore preferred that the antibody, or the antigen binding fragment thereof, comprises: (i) a heavy chain variable region having at least 80% sequence identity to the amino acid sequence of SEQ ID NO: 13 and a light chain variable region having at least 80% sequence identity to the amino acid sequence of SEQ ID NO: 14; or (ii) a heavy chain variable region having at least 80% sequence identity to the amino acid sequence of SEQ ID NO: 29 and a light chain variable region having at least 80% sequence identity to the amino acid sequence of SEQ ID NO: 30; (iii) or a heavy chain variable region having at least 80% sequence identity to the amino acid sequence of SEQ ID NO: 45 and a light chain variable region having at least 80% sequence identity to the amino acid sequence of SEQ ID NO: 46; or (iv) a heavy chain variable region having at least 80% sequence identity to the amino acid sequence of SEQ ID NO: 61 and a light chain variable region having at least 80% sequence identity to the amino acid sequence of SEQ ID NO: 62; or (v) a heavy chain variable region having at least 80% sequence identity to the amino acid sequence of SEQ ID NO: 61 and a light chain variable region having at least 80% sequence identity to the amino acid sequence of SEQ ID NO: 66; or (vi) a heavy chain variable region having at least 80% sequence identity to the amino acid sequence of SEQ ID NO: 65 and a light chain variable region having at least 80% sequence identity to the amino acid sequence of SEQ ID NO: 62; or (vii) a heavy chain variable region having at least 80% sequence identity to the amino acid sequence of SEQ ID NO: 65 and a light chain variable region having at least 80% sequence identity to the amino acid sequence of SEQ ID NO: 66; or (viii) a heavy chain variable region having at least 80% sequence identity to the amino acid sequence of SEQ ID NO: 13 and a light chain variable region having at least 80% sequence identity to the amino acid sequence of SEQ ID NO: 76; or (ix) a heavy chain variable region having at least 80% sequence identity to the amino acid sequence of SEQ ID NO: 75 and a light chain variable region having at least 80% sequence identity to the amino acid sequence of SEQ ID NO: 14; or (x) a heavy chain variable region having at least 80% sequence identity to the amino acid sequence of SEQ ID NO: 75 and a light chain variable region having at least 80% sequence identity to the amino acid sequence of SEQ ID NO: 76; or (xi) a heavy chain variable region having at least 80% sequence identity to the amino acid sequence of SEQ ID NO: 29 and a light chain variable region having at least 80% sequence identity to the amino acid sequence of SEQ ID NO: 86; or (xii) a heavy chain variable region having at least 80% sequence identity to the amino acid sequence of SEQ ID NO: 85 and a light chain variable region having at least 80% sequence identity to the amino acid sequence of SEQ ID NO: 30; or (xiii) a heavy chain variable region having at least 80% sequence identity to the amino acid sequence of SEQ ID NO: 85 and a light chain variable region having at least 80% sequence identity to the amino acid sequence of SEQ ID NO: 86. More preferably, the antibody or the antigen binding fragment comprises: (i) a heavy chain variable region comprising the amino acid sequence of SEQ ID NO: 13 and a light chain variable region comprising the amino acid sequence of SEQ ID NO: 14; or (ii) a heavy chain variable region comprising the amino acid sequence of SEQ ID NO: 29 and a light chain variable region comprising the amino acid sequence of SEQ ID NO: 30; (iii) or a heavy chain variable region comprising the amino acid sequence of SEQ ID NO: 45 and a light chain variable region comprising the amino acid sequence of SEQ ID NO: 46; or (iv) a heavy chain variable region comprising the amino acid sequence of SEQ ID NO: 61 and a light chain variable region comprising the amino acid sequence of SEQ ID NO: 62; or (v) a heavy chain variable region comprising the amino acid sequence of SEQ ID NO: 61 and a light chain variable region comprising the amino acid sequence of SEQ ID NO: 66; or (vi) a heavy chain variable region comprising the amino acid sequence of SEQ ID NO: 65 and a light chain variable region comprising the amino acid sequence of SEQ ID NO: 62; or (vii) a heavy chain variable region comprising the amino acid sequence of SEQ ID NO: 65 and a light chain variable region comprising the amino acid sequence of SEQ ID NO: 66; or (viii) a heavy chain variable region comprising the amino acid sequence of SEQ ID NO: 13 and a light chain variable region comprising the amino acid sequence of SEQ ID NO: 76; or (ix) a heavy chain variable region comprising the amino acid sequence of SEQ ID NO: 75 and a light chain variable region comprising the amino acid sequence of SEQ ID NO: 14; or (x) a heavy chain variable region comprising the amino acid sequence of SEQ ID NO: 75 and a light chain variable region comprising the amino acid sequence of SEQ ID NO: 76; or (xi) a heavy chain variable region comprising the amino acid sequence of SEQ ID NO: 29 and a light chain variable region comprising the amino acid sequence of SEQ ID NO: 86; or (xii) a heavy chain variable region comprising the amino acid sequence of SEQ ID NO: 85 and a light chain variable region comprising the amino acid sequence of SEQ ID NO: 30; or (xiii) a heavy chain variable region comprising the amino acid sequence of SEQ ID NO: 85 and a light chain variable region comprising the amino acid sequence of SEQ ID NO: 86.

Preferably, the antibody, or the antigen binding fragment thereof, is according to gHMB2435, gHMB2435 variant 2, gHMB2435 variant 3, gHMB2435 variant 4, gHMB2437, gHMB2437 variant 2, gHMB2437 variant 3, gHMB2437 variant 4, gHMB2416, gHMB2432 variant 1, gHMB2432 variant 2, gHMB2432 variant 3 or gHMB2432 variant 4. More preferably, the antibody, or the antigen binding fragment thereof, is HMB2435, HMB2435 variant 2, HMB2435 variant 3, HMB2435 variant 4, HMB2437, HMB2437 variant 2, HMB2437 variant 3, HMB2437 variant 4, HMB2416, HMB2432 variant 1, HMB2432 variant 2, HMB2432 variant 3 or HMB2432 variant 4. It is particularly preferred that the antibody, or the antigen binding fragment thereof, specifically binds to antigenic site S5 on the pre-fusion F protein of RSV.

Moreover, it is preferred that the antibody, or the antigen binding fragment thereof, is a human antibody, a monoclonal antibody, a human monoclonal antibody, a purified antibody, a single chain antibody, Fab, Fab', F(ab')2, Fv or scFv.

The present invention also comprises an antibody, or an antigen binding fragment thereof, that binds to the same epitope as the antibody according to the present invention as described above, wherein the antibody or the antigen binding fragment thereof neutralizes infection of both group A and group B RSV, but does not neutralize infection of MPV and wherein the antibody or the antigen binding fragment specifically binds the pre-fusion F protein of RSV, but not the post-fusion RSV F protein, and wherein the antibody or fragment has an isoelectric point (pI) of 7.5 or higher.

The antibody, or the antigen binding fragment thereof, according to the present invention is preferably used in the treatment or attenuation of infection by group A RSV or group B RSV.

In another aspect the present invention also comprises a nucleic acid molecule comprising a polynucleotide encoding the antibody, or the antigen binding fragment thereof, according to the present invention. Preferably, the polynucleotide sequence of the nucleic acid molecule is at least 75% identical to the nucleic acid sequence of any one of SEQ ID NOs: 7-12, 15, 16, 23-28, 31, 32, 39-44, 47, 48, 55-60, 63, 64, 67, 68, 69-74, 77, 78, 79-84, 87, or 88.

In yet another aspect, the present invention also comprises a vector comprising the nucleic acid molecule according to the present invention.

In yet another aspect, the present invention also relates to a cell expressing the antibody, or the antigen binding fragment thereof, according to the present invention; or comprising the vector according to the present invention.

Furthermore, the present invention comprises an isolated or purified immunogenic polypeptide comprising an epitope that specifically binds to the antibody, or the antigen binding fragment thereof, according to the present invention.

In yet another aspect, the present invention also comprises (i) a pharmaceutical composition comprising the antibody, or the antigen binding fragment thereof, the nucleic acid, the vector, the cell, or the immunogenic polypeptide according to the present invention, and a pharmaceutically acceptable excipient, diluent or carrier and/or (ii) a pharmaceutical composition comprising a first antibody or an antigen binding fragment thereof, and a second antibody, or an antigen binding fragment thereof, wherein the first antibody is the antibody according to the present invention, and the second antibody neutralizes infection of RSV or MPV or PVM or any combination of RSV, MPV and PVM.

According to another aspect, the present invention provides the antibody, or the antigen binding fragment thereof, the nucleic acid, the vector, the cell, the immunogenic polypeptide, or the pharmaceutical composition according to the present invention for use as a medicament (i) for the treatment or attenuation of group A RSV or group B RSV infection; (ii) for vaccination against group A RSV or group B RSV infection; or (iii) for diagnosis of group A RSV or group B RSV infection.

Furthermore, the present invention also relates to the use of the antibody, or the antigen binding fragment thereof, according to the present invention, for monitoring the quality of anti-group A RSV or anti-group B RSV vaccines by checking that the antigen of said vaccine contains the specific epitope in the correct conformation.

In one embodiment of the invention, the invention comprises an isolated antibody, or an antigen binding fragment thereof, that neutralizes infection of both group A RSV and group B RSV, but does not neutralize infection of metapneumovirus (MPV), wherein the antibody or antigen binding fragment specifically binds the pre-fusion F protein of RSV, but not the post-fusion RSV F protein. The antibody, or antigen binding fragment thereof, specifically binds the pre-fusion F protein of both group A and group B RSV, but not the post-fusion F protein of group A or group B RSV. Further, the antibody, or an antigen binding fragment thereof, specifically binds the pre-fusion F protein of RSV, but not the pre-fusion F protein of MPV or pneumonia virus of mice (PVM). The antibody, or antigen binding fragment thereof, potently neutralizes infection of both group A and B RSV; the concentration of antibody or antigen binding fragment required for 50% neutralization is 150 ng/ml or less.

In another embodiment of the invention, the invention comprises an isolated antibody, or an antigen binding fragment thereof, that neutralizes infection of both group A RSV and group B RSV, but does not neutralize infection of MPV, wherein the antibody or antigen binding fragment specifically binds the pre-fusion F protein of RSV, but not the post-fusion RSV F protein, and wherein the antibody or fragment has an isoelectric point (pI) of 7.5 or higher. In yet another embodiment of the invention, the invention comprises an isolated antibody, or an antigen binding fragment thereof, that neutralizes infection of both group A RSV and group B RSV, wherein the antibody or antigen binding fragment specifically binds to antigenic site S5 on the pre-fusion F protein of RSV.

In another embodiment of the invention, the invention comprises an isolated antibody, or an antigen binding fragment thereof, that neutralizes infection of both group A and group B RSV and comprises a heavy chain comprising CDR1, CDR2 and CDR3 and a light chain comprising CDR1, CDR2 and CDR3, wherein the heavy chain CDR3 comprises the amino acid sequence of SEQ ID NOs: 3, 19, 35 or 51.

In yet another embodiment of the invention, the invention comprises an isolated antibody or antigen binding fragment thereof, that neutralizes infection of both group A and group B RSV, comprising: (i) heavy chain CDR1, CDR2, and CDR3 amino acid sequences and light chain CDR1, CDR2, and CDR3 amino acid sequences as set forth in SEQ ID NOs: 1-6, respectively; (ii) heavy chain CDR1, CDR2, and CDR3 amino acid sequences and light chain CDR1, CDR2, and CDR3 amino acid sequences as set forth in SEQ ID NOs: 17-22, respectively; (iii) heavy chain CDR1, CDR2, and CDR3 amino acid sequences and light chain CDR1, CDR2, and CDR3 amino acid sequences as set forth in SEQ ID NOs: 33-38, respectively; or (iv) heavy chain CDR1, CDR2, and CDR3 amino acid sequences and light chain CDR1, CDR2, and CDR3 amino acid sequences as set forth in SEQ ID NOs: 49-54, respectively.

In still another embodiment of the invention, the invention comprises an isolated antibody, or an antigen binding fragment thereof, that neutralizes infection of both group A and group B RSV, comprising: (i) a heavy chain variable region comprising the amino acid sequence of SEQ ID NO: 13 and a light chain variable region comprising the amino acid sequence of SEQ ID NO: 14; or (ii) a heavy chain variable region comprising the amino acid sequence of SEQ ID NO: 29 and a light chain variable region comprising the amino acid sequence of SEQ ID NO: 30; (iii) or a heavy chain variable region comprising the amino acid sequence of SEQ ID NO: 45 and a light chain variable region comprising the amino acid sequence of SEQ ID NO: 46; or (iv) a heavy chain variable region comprising the amino acid sequence of SEQ ID NO: 61 and a light chain variable region comprising the amino acid sequence of SEQ ID NO: 62; or (v) a heavy chain variable region comprising the amino acid sequence of SEQ ID NO: 61 and a light chain variable region comprising the amino acid sequence of SEQ ID NO: 66; or (vi) a heavy chain variable region comprising the amino acid sequence of SEQ ID NO: 65 and a light chain variable region comprising the amino acid sequence of SEQ ID NO: 62; or (vii) a heavy chain variable region comprising the amino acid sequence of SEQ ID NO: 65 and a light chain variable region comprising the amino acid sequence of SEQ ID NO: 66. The invention further comprises an isolated antibody, or an antigen binding fragment thereof, described herein as HMB2435, HMB2437, HMB2416, HMB2432 variant 1, HMB2432 variant 2, HMB2432 variant 3 or HMB2432 variant 4. In another embodiment, the invention comprises an antibody, or antigen binding fragment thereof, that neutralizes infection of group A and group B RSV, wherein the antibody or fragment thereof is expressed by an immortalized B cell clone that produces HMB2435, HMB2437, HMB2416, HMB2432 variant 1, HMB2432 variant 2, HMB2432 variant 3 or HMB2432 variant 4.

In another aspect, the invention comprises a nucleic acid molecule comprising a polynucleotide encoding an antibody or antibody fragment of the invention. In yet another aspect, the invention comprises a vector comprising a nucleic acid molecule of the invention. The invention also comprises a cell that expresses an antibody of the invention or an antigen binding fragment thereof. In still another aspect, the invention comprises an isolated or purified immunogenic polypeptide comprising an epitope that binds to an antibody or antigen binding fragment of the invention.

The invention further comprises a pharmaceutical composition comprising an antibody of the invention or an antigen binding fragment thereof, a nucleic acid molecule of the invention, a vector comprising a nucleic acid molecule of the invention, a cell expressing an antibody or an antibody fragment of the invention, or an immunogenic polypeptide of the invention, and a pharmaceutically acceptable diluent or carrier. The invention also comprises a pharmaceutical composition comprising a first antibody or an antigen binding fragment thereof, and a second antibody, or an antigen binding fragment thereof, wherein the first antibody is an antibody of the invention, and the second antibody is an antibody, or an antigen binding fragment thereof, that neutralizes infection of RSV, MPV or PVM, or any two of RSV, MPV and PVM, or all three of RSV, MPV, and PVM.

Use of an antibody of the invention, or an antigen binding fragment thereof, a nucleic acid of the invention, a vector comprising a nucleic acid of the invention, a cell expressing a vector of the invention, an isolated or purified immunogenic polypeptide comprising an epitope that binds to an antibody or antibody fragment of the invention, or a pharmaceutical composition of the invention in the manufacture of a medicament for (i) the treatment or attenuation of RSV or group A and group B RSV co-infection, (ii) for vaccination against RSV (group A and group B RSV) infection, or (iii) for diagnosis of RSV (group A or group B RSV) infection is also contemplated to be within the scope of the invention. Further, use of an antibody of the invention, or an antigen binding fragment thereof, for monitoring the quality of a vaccine against RSV or both group A and group B RSV by checking that the antigen of said vaccine contains the specific epitope in the correct conformation is also contemplated to be within the scope of the invention.

In another aspect of the invention, the invention comprises a method of treating or attenuating RSV infection or lowering the risk of RSV infection comprising administering to a subject in need thereof, a therapeutically effective amount of an antibody or an antigen binding antibody fragment of the invention.

In yet another aspect of the invention, the invention comprises a polypeptide which specifically binds to an antibody of the invention, or an antigen binding fragment thereof, for use (i) in therapy, (ii) in the manufacture of a medicament for the treatment or attenuation of RSV, (iii) as a vaccine, or (iv) in screening for ligands able to neutralise infection of RSV.

DESCRIPTION OF FIGURES

FIG. 7 shows the amino acid sequences for the heavy and light chains of antibody HMB2435 as well as the nucleic acid sequences that encode them.

FIG. 8 shows the amino acid sequences for the heavy and light chains of antibody HMB2437 as well as the nucleic acid sequences that encode them.

FIG. 9 shows the amino acid sequences for the heavy and light chains of antibody HMB2416 as well as the nucleic acid sequences that encode them.

FIG. 10 shows the amino acid sequences for the two heavy chains of the variants of antibody HMB2432 and the nucleic acid sequences that encode them (FIG. 10A); as well as the amino acid sequences for the two light chains of the variants of antibody HMB2432 and the nucleic acid sequences that encode them (FIG. 10B).

FIG. 11 shows the amino acid sequence of the heavy and light chains of antibodies HMB2435 and HMB2437 aligned with the corresponding framework regions germlined sequences (FR-GL).

DETAILED DESCRIPTION

Figure 1:
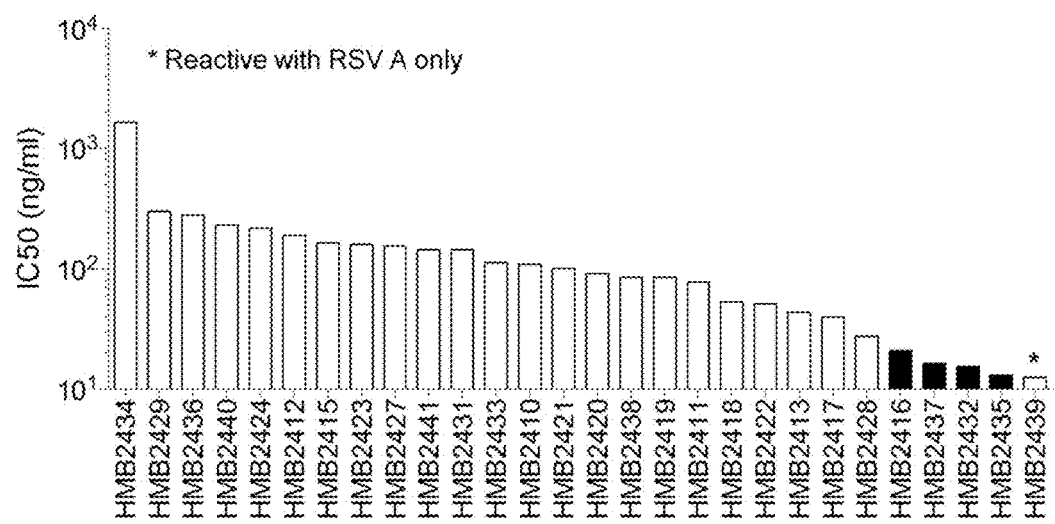
FIG. 1 shows the results of neutralization (IC50 values) of RSV by the panel of 28 monoclonal antibodies isolated.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

As used herein, the terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')$_2$, Fv or scFv. Further, the term "antibody" as used herein includes both antibodies and antigen binding fragments thereof.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

The term "specifically binding" and similar reference does not encompass non-specific sticking.

As used herein, "sequence variant" refers to any alteration in a reference sequence, whereby a reference sequence is any of the sequences listed in the "Table of Sequences and SEQ ID Numbers" (sequence listing), i.e. SEQ ID NO:1 to SEQ ID NO:88. Thus, the term "sequence variant" includes nucleotide sequence variants and amino acid sequence variants.

Sequence identity is usually calculated with regard to the full length of the reference sequence (i.e. the sequence recited in the application). Percentage identity, as referred to herein, can be determined, for example, using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

As used herein, a "nucleotide sequence variant" has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "nucleotide sequence variant" can either result in a change in the respective reference amino acid sequence, i.e. in an "amino acid sequence variant" or not. Preferred sequence variants are such nucleotide sequence variants, which do not result in amino acid sequence variants (silent mutations), but other non-silent mutations are within the scope as well, in particular mutant nucleotide sequences, which result in an amino acid sequence, which is at least 80%, preferably at least 90%, more preferably at least 95% sequence identical to the reference sequence.

An "amino acid sequence variant" has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 80% identical to the reference sequence, preferably, at least 90% identical, more preferably at least 95% identical, most preferably at least 99% identical to the reference sequence. Variant sequences which are at least 90% identical have no more than 10 alterations, i.e. any combination of deletions, insertions or substitutions, per 100 amino acids of the reference sequence.

While it is possible to have non-conservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydoxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Importantly, the alterations in the sequence variants do not abolish the functionality of the respective reference sequence, in the present case, e.g., the functionality of a sequence of an antibody, or antigen binding fragment thereof, to bind to the same epitope and/or to sufficiently neutralize infection of RSV. Guidance in determining which nucleotides and amino acid residues, respectively, may be substituted, inserted or deleted without abolishing such functionality are found by using computer programs well known in the art.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

The invention is based, in part, on the discovery and isolation of antibodies that are highly potent in neutralizing RSV, as well as antigenic sites and epitopes to which the antibodies of the invention bind. Such antibodies are desirable, as only small quantities of the antibodies are required in order to neutralize RSV infection and are highly effective in preventing as well as treating or attenuating RSV infection in high-risk patients. This reduces the costs of production of medicaments comprising the antibodies for the treatment of RSV infection. In addition, the antigenic sites or immunogenic polypeptides comprising epitopes recognized by the antibodies of the invention may be part of a vaccine capable of inducing protection against RSV.

The present invention comprises an isolated antibody, or an antigen binding fragment thereof, that neutralizes infection of both group A RSV and group B RSV, but does preferably not neutralize infection of MPV, wherein preferably the antibody or the antigen binding fragment specifically binds the pre-fusion F protein of RSV, but not the post-fusion RSV F protein. Additionally, the antibody or the antigen binding fragment may preferably not bind the RSV G protein.

In one aspect of the invention, the invention provides an isolated antibody, antibody variants and antigen binding fragments thereof, that neutralize infection of RSV. In one embodiment, the RSV is a human RSV. In another embodiment, the RSV is a bovine RSV.

The antibodies of the invention neutralize infection of both group A RSV (RSV A) and group B RSV (RSV B). As used herein, "group A RSV" and "RSV A" are used interchangeably to refer to an A strain of RSV, and "group B RSV" and "RSV B" are used interchangeably to refer to a B strain of RSV. In one embodiment of the invention, the invention comprises an isolated antibody, or an antigen binding fragment thereof, that neutralizes infection of both group A RSV and group B RSV, but does not neutralize infection of MPV or PVM, wherein the antibody or antigen binding fragment specifically binds the pre-fusion F protein of RSV, but not the post-fusion RSV F protein.

The amino acid sequences of the G and F proteins of RSV are classified into A and B groups. The F protein of RSV is a type I trans-membrane surface protein that has an N-terminal cleaved signal peptide and a membrane anchor near the C-terminus. The F protein is synthesized as an inactive F0 precursor that assembles into homotrimers and is activated by cleavage. The F protein is formed by three domains (DI to DIII), a fusion peptide (FP) and three heptad-repeats regions (HR-A, -B and -C). The F glycoprotein of RSV directs viral penetration by fusion between the virion envelope and the host cell plasma membrane. The N-terminus of the F subunit, that is created by proteolytic cleavage and contains the fusion peptide, inserts directly into the target membrane to initiate fusion. After binding to the target cell and subsequent activation, the metastable pre-fusion F protein undergoes a series of structural rearrangements that result in the insertion of the fusion peptide into the target cell membrane, followed by the formation of a stable helical bundle that forms as the viral and cell membranes are apposed. These structural changes lead to the formation of a stable post-fusion F protein. Later in infection, the F protein expressed on the cell surface of infected cells can mediate fusion with adjacent non-infected cells forming large syncytia.

The epitope for palivizumab has been mapped on the post-fusion RSV F protein antigenic site II (also called site A) formed by residues 255-275, and antibody 101F targets the post-fusion RSV F protein antigenic site IV (also called site C) of RSV formed by residues 422-438. To be effective, antibodies should recognize the pre-fusion F protein, which is the relevant conformation to block virus entry, and preferably avoids recognition of the abundant post-fusion F protein that can act as a decoy, thus consuming the antibody and reducing its efficacy.

In one embodiment of the invention, the invention comprises an isolated antibody, or an antigen binding fragment thereof, that specifically binds RSV pre-fusion F protein, but not RSV post-fusion F protein. The antibody, or antigen binding fragment thereof, specifically binds the pre-fusion F protein of both group A and group B RSV, but not the post-fusion F protein of group A or group B RSV. In yet another embodiment, the invention comprises an isolated antibody, or an antigen binding fragment thereof, that specifically binds the pre-fusion F protein of RSV, but not the pre-fusion F protein of MPV or PVM.

The antibodies of the invention do not, for example, bind the antigenic site II of the RSV F protein (recognized by palivizumab) or antigenic site IV of the RSV F protein (recognized by mAb 101F). The epitopes recognized by the antibodies of the invention on the RSV F protein are also distinct from that recognized by the antibodies disclosed in U.S. application Ser. No. 13/827,845 (and PCT application No. PCT/IB2013/000627).

Preferably, the antibody according to the present invention, or the antigen binding fragment thereof, has an isoelectric point (pI) of 7.5 or higher. The isoelectric point (pI) can, for example, be calculated based on the amino acid sequences.

Preferably, the isoelectric point of the antibodies and the antigen binding fragments of the invention is about 7.5 to about 8.6, for example, about 7.5, about 7.6, about 7.7, about 7.8, about 7.9, about 8.0, about 8.1, about 8.2, about 8.3, about 8.4, about 8.5 or about 8.6. It is also preferred that the isoelectric point of the antibodies and the antigen binding fragments of the invention is higher than 7.5, higher than 7.6, higher than 7.7, higher than 7.8, higher than 7.9, higher than 8.0, higher than 8.05, higher than 8.1, higher than 8.15, higher than 8.2, higher than 8.25, higher than 8.3, higher than 8.35, higher than 8.4, higher than 8.45, higher than 8.5 or higher than 8.55.

It is known in the art that physical aggregation of monoclonal antibodies is pH dependent, since pH has an impact on the tertiary structure conformation as well as the net charge of the protein, thus affecting net protein-protein interactions (Ejima et al., 2007, *Proteins Structural Function Bioinformatics*, 66, 954-962). Aggregation of monoclonal antibodies is favored when the working pH is near to the isoelectric point of the antibody. While solution environment higher than pH 7.0 can promote deamidation of the aspara-gine residues, disulphide exchange and aggregation, lower pH values (pH 4 and below) can promote isomerization, hydrolysis and fragmentation (Zheng et al., 2006, *Internal Journal of Pharmacology*, 308, 46-51). In general currently marketed antibodies have a pI between 7.4 to 8.6 and are formulated in the pH range of 5.0 to 7.2, with most of the antibodies being formulated at slightly acidic pH. Thus, an antibody according to the present invention, or the antigen binding fragment thereof, having an isoelectric point (pI) of 7.5 or higher, makes them excellent candidates for production and formulation in marketable quantities.

The invention further provides antibodies and antigen binding fragments thereof that neutralize infection of RSV A and RSV B and have a higher isoelectric point than some of the other antibodies that neutralize RSV infection. The antibodies of the invention and fragments thereof, for example, have a higher isoelectric point than D25. In one embodiment, the isoelectric point of the antibodies and antigen binding fragments of the invention is about 7.5 to about 8.6, for example, about 7.5, about 7.6, about 7.7, about 7.8, about 7.9, about 8.0, about 8.1, about 8.2, about 8.3, about 8.4, about 8.5 or about 8.6. In another embodiment, the isoelectric point of the antibodies and antigen binding fragments of the invention is higher than 7.5, higher than 7.6, higher than 7.7, higher than 7.8, higher than 7.9, higher than 8.0, higher than 8.05, higher than 8.1, higher than 8.15, higher than 8.2, higher than 8.25, higher than 8.3, higher than 8.35, higher than 8.4, higher than 8.45, higher than 8.5 or higher than 8.55.

Preferably, the antibody or the antigen binding fragment thereof does not specifically bind to the pre-fusion F protein of RSV at antigenic site S1 and/or does not bind to the pre-fusion F protein of RSV at antigenic site S1, respectively. Preferably, the antibody, or the antigen binding fragment thereof, specifically binds to antigenic site S2, antigenic site S3, antigenic site S5 or a site in between antigenic sites S2 and S3 on the pre-fusion F protein of RSV. It is particularly preferred that the antibody, or the antigen binding fragment thereof, specifically binds to antigenic site S5 on the pre-fusion F protein of RSV.

Figure 6:
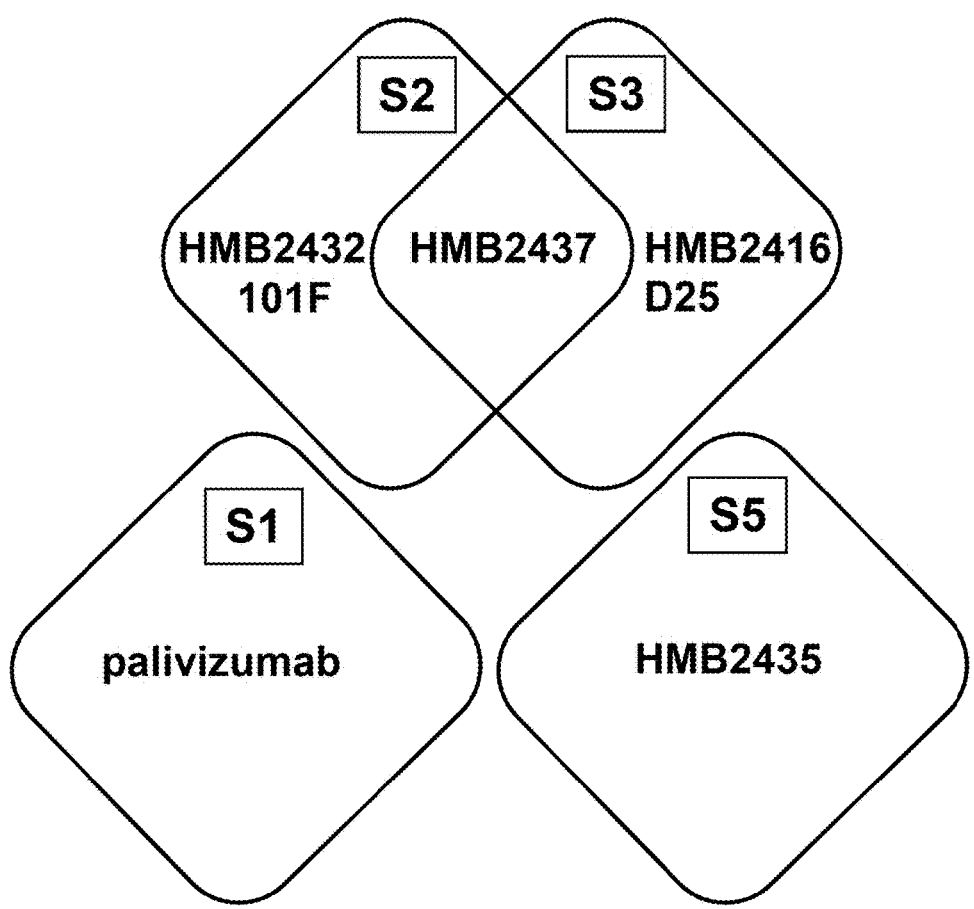
FIG. 6 shows the antigenic sites targeted by HMB2437, HMB2435, HMB2416, HMB2432, D25, palivizumab and 101F monoclonal antibodies on RSV pre-fusion F protein as determined by cross-competition data obtained by surface plasmon resonance (SPR).

Using surface plasmon resonance (SPR), four antigenic sites (S1, S2, S3 and S5) on the pre-fusion F protein of RSV have been identified. More specifically, using cross-competition SPR experiments and a panel of available antibodies of known specificity (palivizumab, D25 and 101F), as well as antibodies according to the present invention, as specified in the Examples, four antigenic sites (S1, S2, S3 and S5) have been identified on the pre-fusion F protein (FIG. 6, Table 6).

For SPR, any SPR system may be used, for example ProteOn-XPR36 instrument (Bio-Rad). Antibodies may be immobilized, for example on a ProteOn GLC sensor chip surface, for example, through amine coupling. For use as a reference, for example, a blank surface with no antibody may be created under identical coupling conditions. RSV F protein may be injected, for example at a flow rate of 100 ml $min^{-1}$, for example at concentrations of 200, 100, 75, 50 and/or 25 nM. The data may be processed for example using Proteon software. For competition experiment, antibodies may be covalently coupled to a GLC sensor chip, RSV F protein may be injected, and the competing antibody may be injected after a dissociation time, for example of 20 s.

Palivizumab binds to antigenic site S1 of the RSV pre-fusion F protein. The antibodies provided as examples of the present invention specifically bind, for example, to antigenic sites S2, S3, S5 or a site in between S2 and S3 on the RSV pre-fusion F protein. In particular, none of the antibodies provided as examples of the present invention competed with palivizumab. Moreover, a preferred antibody or antigen binding fragment thereof according to the present invention does not compete with any of palivizumab, D25 and 101F, indicating that it binds to a novel site, S5, on the pre-fusion F protein.

In one embodiment, the invention provides an isolated antibody, or an antigen binding fragment thereof, that neutralizes infection of both group A RSV and group B RSV and specifically binds to antigenic site S5 on the pre-fusion F protein of RSV. No other antibody known in the art binds to the antigenic site identified for the first time herein as S5.

Four antigenic sites (S1, S2, S3 and S5) on the pre-fusion F protein of RSV have thus been identified herein. In one embodiment, the invention provides an antibody or antigen binding fragment thereof that specifically binds antigenic site S5 of the RSV A or RSV B pre-fusion F protein. In another embodiment, the invention provides an antibody or antigen binding fragment thereof that specifically binds antigenic site S2 of the RSV A or RSV B pre-fusion F protein. In another embodiment, the invention provides an antibody or antigen binding fragment thereof that specifically binds antigenic site S3 of the RSV A or RSV B pre-fusion F protein. In another embodiment, the invention provides an antibody or antigen binding fragment thereof that specifically binds an antigenic site that overlaps sites S2 and S3 of the RSV A or RSV B pre-fusion F protein. In yet another embodiment, the invention provides an antibody or antigen binding fragment thereof that does not specifically bind antigenic site S1 of the RSV A or RSV B pre-fusion F protein.

Preferably, the concentration of the antibody according to the present invention, or the antigen binding fragment thereof, required for 50% neutralization of RSV is 150 ng/ml or less. More preferably, the concentration of the antibody of the invention required for 50% neutralization of both RSV A and RSV B is about 150 ng/ml to about 200 ng/ml. The antibody and antigen binding fragment of the invention have high neutralizing potency. The concentration of the antibody of the invention required for 50% neutralization of RSV A or RSV B is, for example, about 50 ng/ml or less.

This means that only low concentrations of antibody are required for 50% neutralization of RSV. Specificity and potency can be measured using standard assays as known to one of skill in the art. A neutralization assay for RSV typically measures the loss of infectivity through reaction of the virus with specific antibodies. A loss of infectivity is caused by interference by the bound antibody with any of the virus replication steps including binding to target cells, entry, and/or viral release. Usually, a given amount of RSV, e.g. 50-100 TCDID50 (50% tissue culture infective dose), and different concentrations of the (monoclonal) antibodies are mixed under appropriate conditions, e.g. for 1 hour at room temperature, and then inoculated into an appropriate target cell culture, e.g. Hep-2 cells. Values are typically provided per ml cell culture. The presence of unneutralized virus is detected after a predetermined amount of time, e.g. 6 days, by measuring the cytopathic effect of the (unneutralized) virus on target cells, e.g. by using a colorimetric assay for the quantification of cellular viability, like for instance the WST-1 reagent. The more target cells are rescued from cell death or are measured to be viable, the more virus was neutralized by the antibodies. The effects measured are usually dose-dependent: The higher the antibody titer, the more cells are rescued. Depending on the neutralizing character of the antibody, the $TCID_{50}$ values vary, e.g. an antibody of significant neutralizing character will require lower amounts (of the antibody) to be added (for, e.g., achieving the same amount of "rescued" target cells in the assay, i.e. cells measured to be viable) than another antibody of less pronounced neutralizing character.

In one embodiment, the concentration of the antibody of the invention required for 50% neutralization of both RSV A and RSV B is about 150 ng/ml to about 200 ng/ml. In other embodiments, the concentration of the antibody of the invention required for 50% neutralization of group A or group B RSV is about 150 ng/ml or about 120, 100, 90, 80, 75, 70, 60, 50, 45, 40, 35, 30, 25, or about 20 ng/ml or less. In other embodiments, the concentration of the antibody of the invention required for 50% neutralization of RSV A or RSV B is about 20 ng/ml or about 19, 18, 17, 16, 15, 14, 13, 12, 11, 10, 9, 8, 7, 6 5, 4, 3, 2 or about 1 ng/ml or less. In other embodiments, the concentration of the antibody of the invention required for 50% neutralization of RSV A or RSV B is about 1 ng/ml or about 0.9, 0.8, 0.7, 0.6, 0.5, 0.4, 0.3, 0.2 or about 0.1 ng/ml or less. This means that only low concentrations of antibody are required for 50% neutralization of RSV. Specificity and potency can be measured using standard assays as known to one of skill in the art.

Preferably, the antibody according to the present invention, or the antigen binding fragment thereof, is a human antibody, a monoclonal antibody, a human monoclonal antibody, a purified antibody, a single chain antibody, Fab, Fab', F(ab')2, Fv or scFv.

The antibodies of the invention may be human antibodies, monoclonal antibodies, human monoclonal antibodies, recombinant antibodies or purified antibodies. The invention also provides fragments of the antibodies of the invention, particularly fragments that retain the antigen-binding activity of the antibodies. Such fragments include, but are not limited to, single chain antibodies, Fab, Fab', F(ab')2, Fv or scFv. Although the specification, including the claims, may, in some places, refer explicitly to antigen binding fragment(s), antibody fragment(s), variant(s) and/or derivative(s) of antibodies, it is understood that the term "antibody" or "antibody of the invention" includes all categories of antibodies, namely, antigen binding fragment(s), antibody fragment(s), variant(s) and derivative(s) of antibodies.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Preferably, the antibody according to the present invention, or the antigen binding fragment thereof, comprises a heavy chain comprising CDRH1, CDRH2 and CDRH3 and a light chain comprising CDRL1, CDRL2 and CDRL3, wherein the heavy chain CDRH3 comprises an amino acid sequence that is at least 90% identical to SEQ ID NOs: 3, 19, 35 or 51. More preferably, the heavy chain CDRH3 of the antibody, or of the antigen binding fragment thereof, comprises the amino acid sequence of SEQ ID NOs: 3, 19, 35 or 51. In more general terms, the present invention also comprises an antibody, or an antigen binding fragment thereof, comprising a heavy chain comprising CDRH1, CDRH2 and CDRH3 and a light chain comprising CDRL1, CDRL2 and CDRL3, wherein the heavy chain CDRH3 comprises an amino acid sequence variant to SEQ ID NOs: 3, 19, 35 or 51.

In one embodiment, an isolated antibody of the invention, or antigen binding fragment thereof, neutralizes infection of RSV A and RSV B and comprises a heavy chain comprising CDR1, CDR2 and CDR3 and a light chain comprising CDR1, CDR2 and CDR3, wherein the heavy chain CDR3 comprises an amino acid sequence that is at least 90%, for example, 90%, 91%, 92%, 93%, 94%, 95%, 96%, 97%, 98%, 99% or 100% identical to SEQ ID NOs: 3, 19, 35 or 51.

In this context, the antibody according to the present invention, or the antigen binding fragment thereof, preferably comprises (at least) three CDRs on the heavy chain and (at least) three CDRs on the light chain. In general, complementarity determining regions (CDRs) are the hypervariable regions present in heavy chain variable domains and light chain variable domains. Typically, the CDRs of a heavy chain and the connected light chain of an antibody together form the antigen receptor. Usually, the three CDRs (CDR1, CDR2, and CDR3) are arranged non-consecutively in the variable domain. Since antigen receptors are typically composed of two variable domains (on two different polypeptide chains, i.e. heavy and light chain), there are six CDRs for each antigen receptor (heavy chain: CDRH1, CDRH2, and CDRH3; light chain: CDRL1, CDRL2, and CDRL3). A single antibody molecule usually has two antigen receptors and therefore contains twelve CDRs. The CDRs on the heavy and/or light chain may be separated by framework regions, whereby a framework region (FR) is a region in the variable domain which is less "variable" than the CDR. For example, a chain (or each chain, respectively) may be composed of four framework regions, separated by three CDR.

The sequences of the heavy chains and light chains of several antibodies of the invention, each comprising three CDRs on the heavy chain and three CDRs on the light chain have been determined. The position of the CDR amino acids are defined according to the IMGT numbering system (IMGT: http://www.imgt.org/; cf. Lefranc, M.-P. et al. (2009) Nucleic Acids Res. 37, D1006-D1012). The sequences of the CDRs, heavy chains, light chains as well as the sequences of the nucleic acid molecules encoding the CDRs, heavy chains, light chains of the antibodies of the invention, i.e. of several antibodies according to the invention, are disclosed in the sequence listing. The CDRs of the antibody heavy chains are also referred to as CDRH1, CDRH2 and CDRH3, respectively. Similarly, the CDRs of the antibody light chains are also referred to as CDRL1, CDRL2 and CDRL3, respectively. Table 1 provides the SEQ ID numbers for the amino acid sequences of the six CDRs of the heavy and light chains, respectively, of the exemplary antibodies of the invention.

TABLE 1

SEQ ID Numbers for CDR Polypeptides of Antibodies that Neutralize RSV A and RSV B.

| | SEQ ID NOs. for CDR Polypeptides | | | | | |
|---|---|---|---|---|---|---|
| | CDRH1 | CDRH2 | CDRH3 | CDRL1 | CDRL2 | CDRL3 |
| HMB2435 | 1 | 2 | 3 | 4 | 5 | 6 |
| HMB2437 | 17 | 18 | 19 | 20 | 21 | 22 |
| HMB2416 | 33 | 34 | 35 | 36 | 37 | 38 |
| HMB2432 variant 1 | 49 | 50 | 51 | 52 | 53 | 54 |
| HMB2432 variant 2 | 49 | 50 | 51 | 52 | 53 | 54 |
| HMB2432 variant 3 | 49 | 50 | 51 | 52 | 53 | 54 |
| HMB2432 variant 4 | 49 | 50 | 51 | 52 | 53 | 54 |
| HMB2435 Variant 2 | 1 | 2 | 3 | 4 | 5 | 6 |
| HMB2435 variant 3 | 1 | 2 | 3 | 4 | 5 | 6 |
| HMB2435 variant 4 | 1 | 2 | 3 | 4 | 5 | 6 |
| HMB2437 variant 2 | 17 | 18 | 19 | 20 | 21 | 22 |
| HMB2437 variant 3 | 17 | 18 | 19 | 20 | 21 | 22 |
| HMB2437 variant 4 | 17 | 18 | 19 | 20 | 21 | 22 |

The present invention provides RSV-specific antibodies or an antigen binding fragment thereof having improved properties as compared to prior art antibodies. The RSV-specific antibodies according to the present invention have very low $IC_{50}$ values. Such antibodies have a particular high or strong affinity for RSV and are therefore particularly suitable for counteracting and/or at least in part preventing an RSV-infection and/or adverse effects of an RSV infection.

Variant antibodies are also included within the scope of the invention. Thus, variants of the sequences recited in the application are also included within the scope of the invention. Such variants include natural variants generated by somatic mutation in vivo during the immune response or in vitro upon culture of immortalized B cell clones. Alternatively, variants may arise due to the degeneracy of the genetic code or may be produced due to errors in transcription or translation.

Further variants of the antibody sequences having improved affinity and/or potency may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

Preferably, variant antibody sequences may share 70% or more (i.e. 75%, 80%, 85%, 88%, 90%, 92%, 95%, 96%, 97%, 98%, 99% or more) amino acid sequence identity with the sequences recited in the application. Such variants usually have a greater homology to the sequences listed herein in the CDRs of the heavy chain variable region ($V_H$) and light chain variable region ($V_L$) than in the framework region. As is known to one of skill in the art, mutations are more tolerated, i.e., limited or no loss of function (e.g., specificity or neutralization ability) in the framework regions than in the CDRs.

The invention thus comprises an antibody, or an antigen binding fragment thereof, wherein the variation from the sequences provided herein is preferably in the framework region(s) of the antibody or in the nucleic acid residues that encode the framework region(s) of the antibody.

In the present invention, such (variant) antibodies are preferred, in which the number of somatic mutations is reduced (i.e. "germlined" antibodies: reverted back to the "germline" configuration). Germline sequences of antibodies may be determined, for example, with reference to IMGT database (e.g., according to the IMGT VDJ and VJ assignments and rearrangement interpretation: http://www.imgt.org/; cf. Lefranc, M.-P. et al. (2009) Nucleic Acids Res. 37, D1006-D1012) and "germlined" antibody variants may be produced, for example, by gene synthesis or by site-directed mutagenesis. A low level of somatic mutations reduces the potential risk of antibody immunogenicity. Preferably, the number of somatic mutations is reduced in the framework regions (FR) (i.e. "framework regions germlined" antibodies, also referred to herein as FR-GL variants). (Variant) antibodies, or an antigen binding fragment thereof, and FR-GL variants, respectively, without any somatic mutations in the framework regions (FR) are more preferred. Particularly preferred are such (variant) antibodies, or an antigen binding fragment thereof, and FR-GL variants, respectively, with as few somatic mutations as possible, whereby on the other hand the neutralizing activity is not impaired (as compared to the reference antibody/fragment containing (more) somatic mutations). Such antibodies are on the one hand not impaired in their neutralizing activities, thus showing a very high potency and breadth. On the other hand, a potential risk of antibody immunogenicity is significantly reduced.

In one embodiment, an isolated antibody or antibody fragment of the invention comprises at least one CDR with a sequence that has at least 95% sequence identity to any one of SEQ ID NOs: 1-6, 17-22, 33-38, or 49-54. The amino acid sequences of the heavy and light chain variable regions of the antibodies of the invention as well as the nucleic acid sequences that encode them are provided in FIGS. 7-10. The amino acid residues corresponding to the six CDRs and the nucleic acid residues that encode them are highlighted in bold text.

Preferably, an isolated antibody, or antigen binding fragment thereof, according to the present invention comprises more than one CDR with a sequence that has at least 95% sequence identity to any one of SEQ ID NOs: 1-6, 17-22, 33-38, or 49-54.

Preferably, the antibody, or antigen binding fragment thereof, comprises two CDRs with a sequence that has at least 95% sequence identity to any one of SEQ ID NOs: 1-6, 17-22, 33-38, or 49-54. Thereby it is preferred that the antibody, or antigen binding fragment thereof, comprises (i) a CDRH1 that has at least 95% sequence identity to any one of SEQ ID NOs: 1, 17, 33 or 49, and a CDRL1 that has at least 95% sequence identity to any one of SEQ ID NOs: 4, 20, 36 or 52; (ii) a CDRH2 that has at least 95% sequence identity to any one of SEQ ID NOs: 2, 18, 34 or 50, and a CDRL2 that has at least 95% sequence identity to any one of SEQ ID NOs: 5, 21, 37 or 53; or (iii) a CDRH3 that has at least 95% sequence identity to any one of SEQ ID NOs: 3, 19, 35 or 51, and a CDRL3 that has at least 95% sequence identity to any one of SEQ ID NOs: 6, 22, 38 or 54.

Preferably, the antibody, or antigen binding fragment thereof, comprises three CDRs with a sequence that has at least 95% sequence identity to any one of SEQ ID NOs: 1-6, 17-22, 33-38, or 49-54. Thereby it is preferred that the antibody, or antigen binding fragment thereof, comprises (i) a CDRH1 that has at least 95% sequence identity to any one of SEQ ID NOs: 1, 17, 33 or 49, a CDRH2 that has at least 95% sequence identity to any one of SEQ ID NOs: 2, 18, 34 or 50, and a CDRH3 that has at least 95% sequence identity to any one of SEQ ID NOs: 3, 19, 35 or 51; or (ii) a CDRL1 that has at least 95% sequence identity to any one of SEQ ID NOs: 4, 20, 36 or 52, a CDRL2 that has at least 95% sequence identity to any one of SEQ ID NOs: 5, 21, 37 or 53, and a CDRL3 that has at least 95% sequence identity to any one of SEQ ID NOs: 6, 22, 38 or 54.

Preferably, the antibody, or antigen binding fragment thereof, comprises four CDRs with a sequence that has at least 95% sequence identity to any one of SEQ ID NOs: 1-6, 17-22, 33-38, or 49-54. Thereby it is preferred that the antibody, or antigen binding fragment thereof, comprises (i) a CDRH1 that has at least 95% sequence identity to any one of SEQ ID NOs: 1, 17, 33 or 49, a CDRH2 that has at least 95% sequence identity to any one of SEQ ID NOs: 2, 18, 34 or 50, a CDRH3 that has at least 95% sequence identity to any one of SEQ ID NOs: 3, 19, 35 or 51, and a CDRL that has at least 95% sequence identity to any one of SEQ ID NOs: 4-6, 20-22, 36-38, or 52-54; (ii) a CDRL1 that has at least 95% sequence identity to any one of SEQ ID NOs: 4, 20, 36 or 52, a CDRL2 that has at least 95% sequence identity to any one of SEQ ID NOs: 5, 21, 37 or 53, a CDRL3 that has at least 95% sequence identity to any one of SEQ ID NOs: 6, 22, 38 or 54, and a CDRH that has at least 95% sequence identity to any one of SEQ ID NOs: 1-3, 17-19, 33-35, or 49-51, whereby a CDRH3 that has at least 95% sequence identity to any one of SEQ ID NOs: 3, 19, 35 or 51 is particularly preferred; (iii) a CDRH1 that has at least 95% sequence identity to any one of SEQ ID NOs: 1, 17, 33 or 49, a CDRL1 that has at least 95% sequence identity to any one of SEQ ID NOs: 4, 20, 36 or 52, a CDRH2 that has at least 95% sequence identity to any one of SEQ ID NOs: 2, 18, 34 or 50, and a CDRL2 that has at least 95% sequence identity to any one of SEQ ID NOs: 5, 21, 37 or 53; (iv) a CDRH1 that has at least 95% sequence identity to any one of SEQ ID NOs: 1, 17, 33 or 49, a CDRL1 that has at least 95% sequence identity to any one of SEQ ID NOs: 4, 20, 36 or 52, a CDRH3 that has at least 95% sequence identity to any one of SEQ ID NOs: 3, 19, 35 or 51, and a CDRL3 that has at least 95% sequence identity to any one of SEQ ID NOs: 6, 22, 38 or 54; or (v) a CDRH2 that has at least 95% sequence identity to any one of SEQ ID NOs: 2, 18, 34 or 50, a CDRL2 that has at least 95% sequence identity to any one of SEQ ID NOs: 5, 21, 37 or 53, a CDRH3 that has at least 95% sequence identity to any one of SEQ ID NOs: 3, 19, 35 or 51, and a CDRL3 that has at least 95% sequence identity to any one of SEQ ID NOs: 6, 22, 38 or 54.

Preferably, the antibody, or antigen binding fragment thereof, comprises five CDRs with a sequence that has at least 95% sequence identity to any one of SEQ ID NOs: 1-6, 17-22, 33-38, or 49-54. Thereby it is preferred that the antibody, or antigen binding fragment thereof, comprises five CDRs selected from the group of a CDRH1 that has at least 95% sequence identity to any one of SEQ ID NOs: 1, 17, 33 or 49, a CDRH2 that has at least 95% sequence identity to any one of SEQ ID NOs: 2, 18, 34 or 50, a CDRH3 that has at least 95% sequence identity to any one of SEQ ID NOs: 3, 19, 35 or 51, a CDRL1 that has at least 95% sequence identity to any one of SEQ ID NOs: 4, 20, 36 or 52, a CDRL2 that has at least 95% sequence identity to any one of SEQ ID NOs: 5, 21, 37 or 53, and a CDRL3 that has at least 95% sequence identity to any one of SEQ ID NOs: 6, 22, 38 or 54.

Preferably, the antibody, or antigen binding fragment thereof, comprises six CDRs with a sequence that has at least 95% sequence identity to any one of SEQ ID NOs: 1-6, 17-22, 33-38, or 49-54. Thereby it is preferred that the antibody, or antigen binding fragment thereof, comprises six CDRs selected from the group of a CDRH1 that has at least 95% sequence identity to any one of SEQ ID NOs: 1, 17, 33 or 49, a CDRH2 that has at least 95% sequence identity to any one of SEQ ID NOs: 2, 18, 34 or 50, a CDRH3 that has at least 95% sequence identity to any one of SEQ ID NOs: 3, 19, 35 or 51, a CDRL1 that has at least 95% sequence identity to any one of SEQ ID NOs: 4, 20, 36 or 52, a CDRL2 that has at least 95% sequence identity to any one of SEQ ID NOs: 5, 21, 37 or 53, and a CDRL3 that has at least 95% sequence identity to any one of SEQ ID NOs: 6, 22, 38 or 54. More preferably, the antibody, or antigen binding fragment thereof, comprises: (i) heavy chain CDRH1, CDRH2, and CDRH3 amino acid sequences and light chain CDRL1, CDRL2, and CDRL3 amino acid sequences that are at least 90% identical to the amino acid sequences of SEQ ID NOs: 1-6, respectively; (ii) heavy chain CDRH1, CDRH2, and CDRH3 amino acid sequences and light chain CDRL1, CDRL2, and CDRL3 amino acid sequences that are at least 90% identical to the amino acid sequences of SEQ ID NOs: 17-22, respectively; (iii) heavy chain CDRH1, CDRH2, and CDRH3 amino acid sequences and light chain CDRL1, CDRL2, and CDRL3 amino acid sequences that are at least 90% identical to the amino acid sequences of SEQ ID NOs: 33-38, respectively; or (iv) heavy chain CDRH1, CDRH2, and CDRH3 amino acid sequences and light chain CDRL1, CDRL2, and CDRL3 amino acid sequences that are at least 90% identical to the amino acid sequences of SEQ ID NOs: 49-54, respectively.

Among the embodiments described above of the antibody, or antigen binding fragment thereof, of the invention having at least one CDR, i.e. one, two, three, four, five six CDRs as described above, such an embodiment of the antibody, or antigen binding fragment thereof, is preferred, which comprises a CDRH3 that has at least 95% sequence identity to any one of SEQ ID NOs: 3, 19, 35 or 51.

In yet another embodiment, the isolated antibody or antigen binding fragment of the invention comprises a heavy chain CDR1 with the amino acid sequence of SEQ ID NOs: 1, 17, 33 or 49 or sequence variants thereof; a heavy chain CDR2 with the amino acid sequence of SEQ ID NOs: 2, 18, 34 or 50 or sequence variants thereof; and a heavy chain CDR3 with the amino acid sequence of SEQ ID NOs: 3, 19, 35 or 51 or sequence variants thereof. In certain embodiments, an antibody or antibody fragment as provided herein comprises a heavy chain comprising the amino acid sequence of (i) SEQ ID NO: 1 for CDRH1, SEQ ID NO: 2 for CDRH2 and SEQ ID NO: 3 for CDRH3, (ii) SEQ ID NO: 17 for CDRH1, SEQ ID NO: 18 for CDRH2, and SEQ ID NO: 19 for CDRH3, (iii) SEQ ID NO: 33 for CDRH1, SEQ ID NO; 34 for CDRH2, and SEQ ID NO: 35 for CDRH3, or (iv) or SEQ ID NO: 49 for CDRH1, SEQ ID NO: 50 for CDRH2, and SEQ ID NO: 51 for CDRH3.

In one embodiment, the antibody or antigen binding fragment of the invention comprises a light chain CDR1 with the amino acid sequence of SEQ ID NOs: 4, 20, 36 or 52 or sequence variants thereof; a light chain CDR2 with the amino acid sequence of SEQ ID NOs: 5, 21, 37 or 53 or sequence variants thereof; and a light chain CDR3 with the amino acid sequence of SEQ ID NO: 6, 22, 38 or 54 or sequence variants thereof. In certain embodiments, an antibody or antibody fragment as provided herein comprises a light chain comprising the amino acid sequence of (i) SEQ ID NO: 4 for CDRL1, SEQ ID NO: 5 for CDRL2, and SEQ ID NO: 6 for CDRL3; (ii) SEQ ID NO: 20 for CDRL1, SEQ ID NO: 21 for CDRL2, and SEQ ID NO: 22 for CDRL3; (iii) SEQ ID NO: 36 for CDRL1, SEQ ID NO: 37 for CDRL2, and SEQ ID NO: 38 for CDRL3; or (iv) SEQ ID NO: 52 for CDRL1, SEQ ID NO; 53 for CDRL2, and SEQ ID NO: 54 for CDRL3.

In another embodiment of the invention, the invention comprises an isolated antibody or antigen binding fragment thereof, comprising heavy chain CDR1, CDR2 and CDR3 and light chain CDR1, CDR2, and CDR3 amino acid sequences that are at least 90%, for example, 90%, 91%, 92%, 93%, 94%, 95%, 96%, 97%, 98%, 99% or 100% identical to the amino acid sequences of SEQ ID NOs: 1-6; 17-22; 33-38; or 49-54, respectively, wherein the antibody neutralizes infection of both group A and group B RSV.

In another embodiment, the invention comprises an isolated antibody or antigen binding fragment thereof, that neutralizes infection of both group A and group B RSV, comprising: (i) heavy chain CDR1, CDR2, and CDR3 amino acid sequences and light chain CDR1, CDR2, and CDR3 amino acid sequences that are at least 90% identical to the amino acid sequences of SEQ ID NOs: 1-6, respectively; (ii) heavy chain CDR1, CDR2, and CDR3 amino acid sequences and light chain CDR1, CDR2, and CDR3 amino acid sequences that are at least 90% identical to the amino acid sequences of SEQ ID NOs: 17-22, respectively; (iii) heavy chain CDR1, CDR2, and CDR3 amino acid sequences and light chain CDR1, CDR2, and CDR3 amino acid sequences that are at least 90% identical to the amino acid sequences of SEQ ID NOs: 33-38, respectively; or (iv) heavy chain CDR1, CDR2, and CDR3 amino acid sequences and light chain CDR1, CDR2, and CDR3 amino acid sequences that are at least 90% identical to the amino acid sequences of SEQ ID NOs: 49-54, respectively.

In yet another embodiment of the invention, the invention comprises an isolated antibody or antigen binding fragment thereof, that neutralizes infection of both group A and group B RSV, comprising: (i) heavy chain CDR1, CDR2, and CDR3 amino acid sequences and light chain CDR1, CDR2, and CDR3 amino acid sequences as set forth in SEQ ID NOs: 1-6, respectively; (ii) heavy chain CDR1, CDR2, and CDR3 amino acid sequences and light chain CDR1, CDR2, and CDR3 amino acid sequences as set forth in SEQ ID NOs: 17-22, respectively; (iii) heavy chain CDR1, CDR2, and CDR3 amino acid sequences and light chain CDR1, CDR2, and CDR3 amino acid sequences as set forth in SEQ ID NOs: 33-38, respectively; or (iv) heavy chain CDR1, CDR2, and CDR3 amino acid sequences and light chain CDR1, CDR2, and CDR3 amino acid sequences as set forth in SEQ ID NOs: 49-54, respectively.

Preferably, the antibody, or the antigen binding fragment thereof, is according to gHMB2435, gHMB2435 variant 2, gHMB2435 variant 3, gHMB2435 variant 4, gHMB2437, gHMB2437 variant 2, gHMB2437 variant 3, gHMB2437 variant 4, gHMB2416, gHMB2432 variant 1, gHMB2432 variant 2, gHMB2432 variant 3 or gHMB2432 variant 4. More preferably, the antibody, or the antigen binding fragment thereof, is HMB2435, HMB2435 variant 2, HMB2435 variant 3, HMB2435 variant 4, HMB2437, HMB2437 variant 2, HMB2437 variant 3, HMB2437 variant 4, HMB2416, HMB2432 variant 1, HMB2432 variant 2, HMB2432 variant 3 or HMB2432 variant 4.

The present inventors have isolated four monoclonal antibodies (mAbs), which are referred to herein as "HMB2437", "HMB2435", "HMB2416", and "HMB2432" (cf. Example 1). These antibodies have been further analyzed and the VH and VL genes of HMB2437, HMB2435, HMB2416, and HMB2432 have been cloned into appropriate expression vectors and recombinant antibodies were produced (cf. Example 1). Based on the antibodies HMB2437, HMB2435, HMB2416, and HMB2432, in particular on the VH and VL genes of HMB2437, HMB2435, HMB2416, and HMB2432, the terms "gHMB2435", "gHMB2435 variant 2", "gHMB2435 variant 3", "gHMB2435 variant 4", "gHMB2437", "gHMB2437 variant 2", "gHMB2437 variant 3", "gHMB2437 variant 4", "gHMB2416", "gHMB2432 variant 1", "gHMB2432 variant 2", "gHMB2432 variant 3" and "gHMB2432 variant 4", as used herein, refer to respective "generic" antibodies, or antigen binding fragments thereof, having the specific amino acid sequences, encoded by the specific nucleotide sequences, as outlined below.

As used herein, "gHMB2435" refers to an antibody, or antigen binding fragment thereof, having a CDRH1 amino acid sequence according to SEQ ID NO: 1, which is encoded by a CDRH1 nucleotide sequence according to SEQ ID NO: 7, a CDRH2 amino acid sequence according to SEQ ID NO: 2, which is encoded by a CDRH2 nucleotide sequence according to SEQ ID NO: 8, a CDRH3 amino acid sequence according to SEQ ID NO: 3, which is encoded by a CDRH3 nucleotide sequence according to SEQ ID NO: 9, a CDRL1 amino acid sequence according to SEQ ID NO: 4, which is encoded by a CDRL1 nucleotide sequence according to SEQ ID NO: 10, a CDRL2 amino acid sequence according to SEQ ID NO: 5, which is encoded by a CDRL2 nucleotide sequence according to SEQ ID NO: 11, and a CDRL3 amino acid sequence according to SEQ ID NO: 6, which is encoded by a CDRL3 nucleotide sequence according to SEQ ID NO: 12. The heavy chain variable region ($V_H$) of "gHMB2435" has an amino acid sequence according to SEQ ID NO: 13, which is encoded by a nucleotide sequence according to SEQ ID NO: 15, and the light chain variable region ($V_L$) of "gHMB2435" has an amino acid sequence according to SEQ ID NO: 14, which is encoded by a nucleotide sequence according to SEQ ID NO: 16.

As used herein, "gHMB2435 variant 2", "gHMB2435 variant 3", and "gHMB2435 variant 4" refers to antibodies, or antigen binding fragments thereof, which are framework regions germlined (FR-GL) variants of "gHMB2435". "gHMB2435 variant 2", "gHMB2435 variant 3", and "gHMB2435 variant 4" have the same CDR amino acid sequences as "gHMB2435", i.e. having a CDRH1 amino acid sequence according to SEQ ID NO: 1, a CDRH2 amino acid sequence according to SEQ ID NO: 2, a CDRH3 amino acid sequence according to SEQ ID NO: 3, a CDRL1 amino acid sequence according to SEQ ID NO: 4, a CDRL2 amino acid sequence according to SEQ ID NO: 5, and a CDRL3 amino acid sequence according to SEQ ID NO: 6.

In the "gHMB2435 variant 2", the CDRH1 amino acid sequence is encoded by a CDRH1 nucleotide sequence according to SEQ ID NO: 7, the CDRH2 amino acid sequence is encoded by a CDRH2 nucleotide sequence according to SEQ ID NO: 8, the CDRH3 amino acid sequence is encoded by a CDRH3 nucleotide sequence according to SEQ ID NO: 9, the CDRL1 amino acid sequence is encoded by a CDRL1 nucleotide sequence according to SEQ ID NO: 72, the CDRL2 amino acid sequence is encoded by a CDRL2 nucleotide sequence according to SEQ ID NO: 73, and the CDRL3 amino acid sequence is encoded by a CDRL3 nucleotide sequence according to SEQ ID NO: 74. The heavy chain variable region ($V_H$) of "gHMB2435 variant 2" has an amino acid sequence according to SEQ ID NO: 13, which is encoded by a nucleotide sequence according to SEQ ID NO: 15, and the light chain variable region ($V_L$) of "gHMB2435 variant 2" has an amino acid sequence according to SEQ ID NO: 76, which is encoded by a nucleotide sequence according to SEQ ID NO: 78.

In the "gHMB2435 variant 3", the CDRH1 amino acid sequence is encoded by a CDRH1 nucleotide sequence according to SEQ ID NO: 69, the CDRH2 amino acid sequence is encoded by a CDRH2 nucleotide sequence according to SEQ ID NO: 70, the CDRH3 amino acid sequence is encoded by a CDRH3 nucleotide sequence according to SEQ ID NO: 71, the CDRL1 amino acid sequence is encoded by a CDRL1 nucleotide sequence according to SEQ ID NO: 10, the CDRL2 amino acid sequence is encoded by a CDRL2 nucleotide sequence according to SEQ ID NO: 11, and the CDRL3 amino acid sequence is encoded by a CDRL3 nucleotide sequence according to SEQ ID NO: 12. The heavy chain variable region ($V_H$) of "gHMB2435 variant 3" has an amino acid sequence according to SEQ ID NO: 75, which is encoded by a nucleotide sequence according to SEQ ID NO: 77, and the light chain variable region ($V_L$) of "gHMB2435 variant 3" has an amino acid sequence according to SEQ ID NO: 14, which is encoded by a nucleotide sequence according to SEQ ID NO: 16.

In the "gHMB2435 variant 4", the CDRH1 amino acid sequence is encoded by a CDRH1 nucleotide sequence according to SEQ ID NO: 69, the CDRH2 amino acid sequence is encoded by a CDRH2 nucleotide sequence according to SEQ ID NO: 70, the CDRH3 amino acid sequence is encoded by a CDRH3 nucleotide sequence according to SEQ ID NO: 71, the CDRL1 amino acid sequence is encoded by a CDRL1 nucleotide sequence according to SEQ ID NO: 72, the CDRL2 amino acid sequence is encoded by a CDRL2 nucleotide sequence according to SEQ ID NO: 73, and the CDRL3 amino acid sequence is encoded by a CDRL3 nucleotide sequence according to SEQ ID NO: 74. The heavy chain variable region ($V_H$) of "gHMB2435 variant 4" has an amino acid sequence according to SEQ ID NO: 75, which is encoded by a nucleotide sequence according to SEQ ID NO: 77, and the light chain variable region ($V_L$) of "gHMB2435 variant 4" has an amino acid sequence according to SEQ ID NO: 76, which is encoded by a nucleotide sequence according to SEQ ID NO: 78.

"gHMB2435 variant 4" has, for example, only 14 amino acids somatic mutations in total in the heavy and light chains, which are all located in the CDRs. "gHMB2435", in contrast, has 34 amino acids somatic mutations, with 20 out of the 34 amino acids somatic mutations located in the framework regions, while the other 14 amino acids somatic mutations are located in the CDRs. Therefore, the number of somatic mutations in the framework regions is considerably reduced in "gHMB2435 variant 4" as compared to "gHMB2435"—in fact, "gHMB2435 variant 4" does not have any amino acid somatic mutations in the framework regions. However, "gHMB2435 variant 4" is not impaired in neutralization activity compared to "gHMB2435" and, thus, shows a very high potency and breadth, whereby the potential risk of antibody immunogenicity is significantly reduced due to the low level of somatic mutations. For these reasons an antibody, or antigen binding fragment thereof, according to "gHMB2435 variant 4" is particularly preferred. Accordingly, an antibody, or antigen binding fragment thereof, having a heavy chain variable region ($V_H$) having an amino acid sequence according to SEQ ID NO: 75, which is preferably encoded by a nucleotide sequence according to SEQ ID NO: 77 or sequence variants thereof, and a light chain variable region ($V_L$) having an amino acid sequence according to SEQ ID NO: 76, which is preferably encoded by a nucleotide sequence according to SEQ ID NO: 78 or sequence variants thereof, is particularly preferred.

As used herein, "gHMB2437" refers to an antibody, or antigen binding fragment thereof, having a CDRH1 amino acid sequence according to SEQ ID NO: 17, which is encoded by a CDRH1 nucleotide sequence according to SEQ ID NO: 23, a CDRH2 amino acid sequence according to SEQ ID NO: 18, which is encoded by a CDRH2 nucleotide sequence according to SEQ ID NO: 24, a CDRH3 amino acid sequence according to SEQ ID NO: 19, which is encoded by a CDRH3 nucleotide sequence according to SEQ ID NO: 25, a CDRL1 amino acid sequence according to SEQ ID NO: 20, which is encoded by a CDRL1 nucleotide sequence according to SEQ ID NO: 26, a CDRL2 amino acid sequence according to SEQ ID NO: 21, which is encoded by a CDRL2 nucleotide sequence according to SEQ ID NO: 27, and a CDRL3 amino acid sequence according to SEQ ID NO: 22, which is encoded by a CDRL3 nucleotide sequence according to SEQ ID NO: 28. The heavy chain variable region ($V_H$) of "gHMB2437" has an amino acid sequence according to SEQ ID NO: 29, which is encoded by a nucleotide sequence according to SEQ ID NO: 31, and the light chain variable region ($V_L$) of "gHMB2437" has an amino acid sequence according to SEQ ID NO: 30, which is encoded by a nucleotide sequence according to SEQ ID NO: 32.

As used herein, "gHMB2437 variant 2", "gHMB2437 variant 3", and "gHMB2437 variant 4" refers to antibodies, or antigen binding fragments thereof, which are framework regions germlined (FR-GL) variants of "gHMB2437". "gHMB2437 variant 2", "gHMB2437 variant 3", and "gHMB2437 variant 4" have the same CDR amino acid sequences as "gHMB2437", i.e. having a CDRH1 amino acid sequence according to SEQ ID NO: 17, a CDRH2 amino acid sequence according to SEQ ID NO: 18, a CDRH3 amino acid sequence according to SEQ ID NO: 19, a CDRL1 amino acid sequence according to SEQ ID NO: 20, a CDRL2 amino acid sequence according to SEQ ID NO: 21, and a CDRL3 amino acid sequence according to SEQ ID NO: 22.

In the "gHMB2437 variant 2", the CDRH1 amino acid sequence is encoded by a CDRH1 nucleotide sequence according to SEQ ID NO: 23, the CDRH2 amino acid sequence is encoded by a CDRH2 nucleotide sequence according to SEQ ID NO: 24, the CDRH3 amino acid sequence is encoded by a CDRH3 nucleotide sequence according to SEQ ID NO: 25, the CDRL1 amino acid sequence is encoded by a CDRL1 nucleotide sequence according to SEQ ID NO: 82, the CDRL2 amino acid sequence is encoded by a CDRL2 nucleotide sequence according to SEQ ID NO: 83, and the CDRL3 amino acid sequence is encoded by a CDRL3 nucleotide sequence according to SEQ ID NO: 84. The heavy chain variable region ($V_H$) of "gHMB2437 variant 2" has an amino acid sequence according to SEQ ID NO: 29, which is encoded by a nucleotide sequence according to SEQ ID NO: 31, and the light chain variable region ($V_L$) of "gHMB2437 variant 2" has an amino acid sequence according to SEQ ID NO: 86, which is encoded by a nucleotide sequence according to SEQ ID NO: 88.

In the "gHMB2437 variant 3", the CDRH1 amino acid sequence is encoded by a CDRH1 nucleotide sequence according to SEQ ID NO: 79, the CDRH2 amino acid sequence is encoded by a CDRH2 nucleotide sequence according to SEQ ID NO: 80, the CDRH3 amino acid sequence is encoded by a CDRH3 nucleotide sequence according to SEQ ID NO: 81, the CDRL1 amino acid sequence is encoded by a CDRL1 nucleotide sequence according to SEQ ID NO: 26, the CDRL2 amino acid sequence is encoded by a CDRL2 nucleotide sequence according to SEQ ID NO: 27, and the CDRL3 amino acid sequence is encoded by a CDRL3 nucleotide sequence according to SEQ ID NO: 28. The heavy chain variable region ($V_H$) of "gHMB2437 variant 3" has an amino acid sequence according to SEQ ID NO: 85, which is encoded by a nucleotide sequence according to SEQ ID NO: 87, and the light chain variable region ($V_L$) of "gHMB2437 variant 3" has an amino acid sequence according to SEQ ID NO: 30, which is encoded by a nucleotide sequence according to SEQ ID NO: 32.

In the "gHMB2437 variant 4", the CDRH1 amino acid sequence is encoded by a CDRH1 nucleotide sequence according to SEQ ID NO: 79, the CDRH2 amino acid sequence is encoded by a CDRH2 nucleotide sequence according to SEQ ID NO: 80, the CDRH3 amino acid sequence is encoded by a CDRH3 nucleotide sequence according to SEQ ID NO: 81, the CDRL1 amino acid sequence is encoded by a CDRL1 nucleotide sequence according to SEQ ID NO: 82, the CDRL2 amino acid sequence is encoded by a CDRL2 nucleotide sequence according to SEQ ID NO: 83, and the CDRL3 amino acid sequence is encoded by a CDRL3 nucleotide sequence according to SEQ ID NO: 84. The heavy chain variable region ($V_H$) of "gHMB2437 variant 4" has an amino acid sequence according to SEQ ID NO: 85, which is encoded by a nucleotide sequence according to SEQ ID NO: 87, and the light chain variable region ($V_L$) of "gHMB2437 variant 4" has an amino acid sequence according to SEQ ID NO: 86, which is encoded by a nucleotide sequence according to SEQ ID NO: 88.

As used herein, "gHMB2416" refers to an antibody, or antigen binding fragment thereof, having a CDRH1 amino acid sequence according to SEQ ID NO: 33, which is encoded by a CDRH1 nucleotide sequence according to SEQ ID NO: 39, a CDRH2 amino acid sequence according to SEQ ID NO: 34, which is encoded by a CDRH2 nucleotide sequence according to SEQ ID NO: 40, a CDRH3 amino acid sequence according to SEQ ID NO: 35, which is encoded by a CDRH3 nucleotide sequence according to SEQ ID NO: 41, a CDRL1 amino acid sequence according to SEQ ID NO: 36, which is encoded by a CDRL1 nucleotide sequence according to SEQ ID NO: 42, a CDRL2 amino acid sequence according to SEQ ID NO: 37, which is encoded by a CDRL2 nucleotide sequence according to SEQ ID NO: 43, and a CDRL3 amino acid sequence according to SEQ ID NO: 38, which is encoded by a CDRL3 nucleotide sequence according to SEQ ID NO: 44. The heavy chain variable region ($V_H$) of "gHMB2416" has an amino acid sequence according to SEQ ID NO: 45, which is encoded by a nucleotide sequence according to SEQ ID NO: 47, and the light chain variable region ($V_L$) of "gHMB2416" has an amino acid sequence according to SEQ ID NO: 46, which is encoded by a nucleotide sequence according to SEQ ID NO: 48.

As used herein, "gHMB2432 variant 1", "gHMB2432 variant 2", "gHMB2432 variant 3", and "gHMB2432 variant 4" refers to antibodies, or antigen binding fragments thereof, having a CDRH1 amino acid sequence according to SEQ ID NO: 49, which is encoded by a CDRH1 nucleotide sequence according to SEQ ID NO: 55, a CDRH2 amino acid sequence according to SEQ ID NO: 50, which is encoded by a CDRH2 nucleotide sequence according to SEQ ID NO: 56, a CDRH3 amino acid sequence according to SEQ ID NO: 51, which is encoded by a CDRH3 nucleotide sequence according to SEQ ID NO: 57, a CDRL1 amino acid sequence according to SEQ ID NO: 52, which is encoded by a CDRL1 nucleotide sequence according to SEQ ID NO: 58, a CDRL2 amino acid sequence according to SEQ ID NO: 53, which is encoded by a CDRL2 nucleotide sequence according to SEQ ID NO: 59, and a CDRL3 amino acid sequence according to SEQ ID NO: 54, which is encoded by a CDRL3 nucleotide sequence according to SEQ ID NO: 60.

In the "gHMB2432 variant 1", the heavy chain variable region ($V_H$) has an amino acid sequence according to SEQ ID NO: 61, which is encoded by a nucleotide sequence according to SEQ ID NO: 63, and the light chain variable region ($V_L$) of "gHMB2432 variant 1" has an amino acid sequence according to SEQ ID NO: 62, which is encoded by a nucleotide sequence according to SEQ ID NO: 64.

In the "gHMB2432 variant 2", the heavy chain variable region ($V_H$) has an amino acid sequence according to SEQ ID NO: 61, which is encoded by a nucleotide sequence according to SEQ ID NO: 63, and the light chain variable region ($V_L$) of "gHMB2432 variant 2" has an amino acid sequence according to SEQ ID NO: 66, which is encoded by a nucleotide sequence according to SEQ ID NO: 68.

In the "gHMB2432 variant 3", the heavy chain variable region ($V_H$) has an amino acid sequence according to SEQ ID NO: 65, which is encoded by a nucleotide sequence according to SEQ ID NO: 67, and the light chain variable region ($V_L$) of "gHMB2432 variant 3" has an amino acid sequence according to SEQ ID NO: 62, which is encoded by a nucleotide sequence according to SEQ ID NO: 64.

In the "gHMB2432 variant 4", the heavy chain variable region ($V_H$) has an amino acid sequence according to SEQ ID NO: 65, which is encoded by a nucleotide sequence according to SEQ ID NO: 67, and the light chain variable region ($V_L$) of "gHMB2432 variant 4" has an amino acid sequence according to SEQ ID NO: 66, which is encoded by a nucleotide sequence according to SEQ ID NO: 68.

Antibodies according to gHMB2435, gHMB2435 variant 2, gHMB2435 variant 3, gHMB2435 variant 4, gHMB2437, gHMB2437 variant 2, gHMB2437 variant 3, gHMB2437 variant 4, gHMB2416, gHMB2432 variant 1, gHMB2432 variant 2, gHMB2432 variant 3 and gHMB2432 variant 4 neutralize infection of both group A RSV and group B RSV, but do not neutralize infection of MPV. Moreover, they specifically bind the pre-fusion F protein of RSV, but not the post-fusion RSV F protein or the RSV G protein.

Preferably, the antibodies according to gHMB2435, gHMB2435 variant 2, gHMB2435 variant 3, gHMB2435 variant 4, gHMB2437, gHMB2437 variant 2, gHMB2437 variant 3, gHMB2437 variant 4, gHMB2416, gHMB2432 variant 1, gHMB2432 variant 2, gHMB2432 variant 3 and gHMB2432 variant 4 are of the IgG1 type.

In another embodiment, the invention provides an isolated antibody or antigen binding fragment comprising a heavy chain comprising one or more (i.e., one, two or all three) heavy chain CDRs from HMB2435, HMB2435 variant 2, HMB2435 variant 3, HMB2435 variant 4, HMB2437, HMB2437 variant 2, HMB2437 variant 3, HMB2437 variant 4, HMB2416, HMB2432 variant 1, HMB2432 variant 2, HMB2432 variant 3 or HMB2432 variant 4.

Also provided is an isolated antibody or antigen binding fragment that neutralizes infection of RSV A and RSV B and comprises a light chain comprising one or more (i.e. one, two or all three) light chain CDRs from HMB2435, HMB2435 variant 2, HMB2435 variant 3, HMB2435 variant 4, HMB2437, HMB2437 variant 2, HMB2437 variant 3, HMB2437 variant 4, HMB2416, HMB2432 variant 1, HMB2432 variant 2, HMB2432 variant 3 or HMB2432 variant 4.

In one embodiment, an isolated antibody of the invention, or antigen binding fragment thereof, comprises all of the CDRs of antibody HMB2435 as listed in Table 1, and neutralizes infection of RSV A and RSV B. In another embodiment, an antibody of the invention, or antigen binding fragment thereof, comprises all of the CDRs of antibody HMB2437 as listed in Table 1, and neutralizes infection of RSV A and RSV B. In another embodiment, an antibody of the invention, or antigen binding fragment thereof, comprises all of the CDRs of antibody HMB2416 as listed in Table 1, and neutralizes infection of RSV A and RSV B. In another embodiment, an antibody of the invention, or antigen binding fragment thereof, comprises all of the CDRs of antibody HMB2432 as listed in Table 1, and neutralizes infection of RSV A and RSV B.

The SEQ ID numbers for the amino acid sequence for the heavy chain variable region ($V_H$) and the light chain variable region ($V_L$) of exemplary antibodies of the invention as well as the SEQ ID numbers for the nucleic acid sequences encoding them are listed in Table 2.

TABLE 2

SEQ ID Numbers for $V_H$ and $V_L$ amino acid and nucleic acid residues for Antibodies that Neutralize RSV A and RSV B.

|  | $V_H$ amino acid | $V_L$ amino acid | $V_H$ nucleic acid | $V_L$ nucleic acid |
|---|---|---|---|---|
| HMB2435 | 13 | 14 | 15 | 16 |
| HMB2437 | 29 | 30 | 31 | 32 |
| HMB2416 | 45 | 46 | 47 | 48 |
| HMB2432 variant 1 | 61 | 62 | 63 | 64 |
| HMB2432 variant 2 | 61 | 66 | 63 | 68 |
| HMB2432 variant 3 | 65 | 62 | 67 | 64 |
| HMB2432 variant 4 | 65 | 66 | 67 | 68 |
| HMB2435 variant 2 | 13 | 76 | 15 | 78 |
| HMB2435 variant 3 | 75 | 14 | 77 | 16 |
| HMB2435 variant 4 | 75 | 76 | 77 | 78 |
| HMB2437 variant 2 | 29 | 86 | 31 | 88 |
| HMB2437 variant 3 | 85 | 30 | 87 | 32 |
| HMB2437 variant 4 | 85 | 86 | 87 | 88 |

In one embodiment, an antibody or antibody fragment of the invention neutralizes infection of RSV A and RSV B and comprises a heavy chain variable region having an amino acid sequence that is about 70%, 75%, 80%, 85%, 88%, 90%, 92%, 95%, 96%, 97%, 98%, 99% or 100% identical to the sequence recited in any one of SEQ ID NOs: 13, 29, 45, 61, 65, 75 or 85. In another embodiment, the antibody or antibody fragment comprises a light chain variable region having an amino acid sequence that is about 70%, 75%, 80%, 85%, 90%, 85%, 88%, 90%, 92%, 95%, 96%, 97%, 98%, 99% or 100% identical to the sequence recited in SEQ ID NOs: 14, 30, 46, 62, 66, 76 or 86. In yet another embodiment, the antibody or antibody fragment comprises a heavy chain or a light chain variable region having an amino acid sequence that is about 70%, 75%, 80%, 85%, 88%, 90%, 92%, 95%, 96%, 97%, 98%, 99% or 100% identical to the sequences provided in FIGS. 7, 8, 9, 10A, 10B and 11.

FIGS. 7, 8, 9 and 10 show the amino acid sequences for the heavy and light chains of antibodies HMB2435, HMB2437, 2416 and 2432, respectively, as well as the nucleic acid sequences that encode them. The amino acid sequences of the CDRs and the nucleic acid sequences that encode the CDRs are in bold text whereas the amino acid sequences of the framework region and the nucleic acid sequences that encode the framework region are in plain text.

FIG. 11 shows the amino acid sequences of the heavy and light chains of antibodies HMB2435 and HMB2437 aligned with the corresponding framework regions germlined sequences (FR-GL). The amino acid sequences of the CDRs of the heavy and light chains are highlighted by grey boxes. For the FR-GL variants only the substituted amino acids are shown, i.e. the dots symbolize amino acids, which correspond to the respective amino acids of HMB2435 or HMB2437, respectively. The "variants 2" of HMB2435 or HMB2437, respectively, have a heavy chain according to HMB2435 or HMB2437, respectively, and a light chain according to HMB2435 FR-GL or HMB2437 FR-GL, respectively. The "variants 3" of HMB2435 or HMB2437, respectively, have a heavy chain according to HMB2435 FR-GL or HMB2437 FR-GL, respectively, and a light chain according to HMB2435 or HMB2437, respectively. Thus, only the "variants 4" of HMB2435 or HMB2437, respectively, have both, a heavy chain and a light chain according to HMB2435 FR-GL or HMB2437 FR-GL, respectively.

In another embodiment, the invention comprises an isolated antibody, or an antigen binding fragment thereof, that neutralizes infection of RSV A and RSV B and comprises (i) a heavy chain variable region having at least 80%, for example, 85%, 88%, 90%, 92%, 95%, 96%, 97%, 98%, 99% or 100% sequence identity to the amino acid sequence of SEQ ID NO: 13 and a light chain variable region having at least 80%, for example, 85%, 88%, 90%, 92%, 95%, 96%, 97%, 98%, 99% or 100% sequence identity to the amino acid sequence of SEQ ID NO: 14; or (ii) a heavy chain variable region having at least 80%, for example, 85%, 88%, 90%, 92%, 95%, 96%, 97%, 98%, 99% or 100% sequence identity to the amino acid sequence of SEQ ID NO: 29 and a light chain variable region having at least 80%, for example, 85%, 88%, 90%, 92%, 95%, 96%, 97%, 98%, 99% or 100% sequence identity to the amino acid sequence of SEQ ID NO: 30; (iii) or a heavy chain variable region having at least 80%, for example, 85%, 88%, 90%, 92%, 95%, 96%, 97%, 98%, 99% or 100% sequence identity to the amino acid sequence of SEQ ID NO: 45 and a light chain variable region having at least 80%, for example, 85%, 88%, 90%, 92%, 95%, 96%, 97%, 98%, 99% or 100% sequence identity to the amino acid sequence of SEQ ID NO: 46; or (iv) a heavy chain variable region having at least 80%, for example, 85%, 88%, 90%, 92%, 95%, 96%, 97%, 98%, 99% or 100% sequence identity to the amino acid sequence of SEQ ID NO: 61 and a light chain variable region having at least 80%, for example, 85%, 88%, 90%, 92%, 95%, 96%, 97%, 98%, 99% or 100% sequence identity to the amino acid sequence of SEQ ID NO: 62; or (v) a heavy chain variable region having at least 80%, for example, 85%, 88%, 90%, 92%, 95%, 96%, 97%, 98%, 99% or 100% sequence identity to the amino acid sequence of SEQ ID NO: 61 and a light chain variable region having at least 80%, for example, 85%, 88%, 90%, 92%, 95%, 96%, 97%, 98%, 99% or 100% sequence identity to the amino acid sequence of SEQ ID NO: 66; or (vi) a heavy chain variable region having at least 80%, for example, 85%, 88%, 90%, 92%, 95%, 96%, 97%, 98%, 99% or 100% sequence identity to the amino acid sequence of SEQ ID NO: 65 and a light chain variable region having at least 80%, for example, 85%, 88%, 90%, 92%, 95%, 96%, 97%, 98%, 99% or 100% sequence identity to the amino acid sequence of SEQ ID NO: 62; or (vii) a heavy chain variable region having at least 80%, for example, 85%, 88%, 90%, 92%, 95%, 96%, 97%, 98%, 99% or 100% sequence identity to the amino acid sequence of SEQ ID NO: 65 and a light chain variable region having at least 80%, for example, 85%, 88%, 90%, 92%, 95%, 96%, 97%, 98%, 99% or 100% sequence identity to the amino acid sequence of SEQ ID NO: 66; or (viii) a heavy chain variable region having at least 80%, for example, 85%, 88%, 90%, 92%, 95%, 96%, 97%, 98%, 99% or 100% sequence identity to the amino acid sequence of SEQ ID NO: 13 and a light chain variable region having at least 80%, for example, 85%, 88%, 90%, 92%, 95%, 96%, 97%, 98%, 99% or 100% sequence identity to the amino acid sequence of SEQ ID NO: 76; or (ix) a heavy chain variable region having at least 80%, for example, 85%, 88%, 90%, 92%, 95%, 96%, 97%, 98%, 99% or 100% sequence identity to the amino acid sequence of SEQ ID NO: 75 and a light chain variable region having at least 80%, for example, 85%, 88%, 90%, 92%, 95%, 96%, 97%, 98%, 99% or 100% sequence identity to the amino acid sequence of SEQ ID NO: 14; or (x) a heavy chain variable region having at least 80%, for example, 85%, 88%, 90%, 92%, 95%, 96%, 97%, 98%, 99% or 100% sequence identity to the amino acid sequence of SEQ ID NO: 75 and a light chain variable region having at least 80%, for example, 85%, 88%, 90%, 92%, 95%, 96%, 97%, 98%, 99% or 100% sequence identity to the amino acid sequence of SEQ ID NO: 76; or (xi) a heavy chain variable region having at least 80%, for example, 85%, 88%, 90%, 92%, 95%, 96%, 97%, 98%, 99% or 100% sequence identity to the amino acid sequence of SEQ ID NO: 29 and a light chain variable region having at least 80%, for example, 85%, 88%, 90%, 92%, 95%, 96%, 97%, 98%, 99% or 100% sequence identity to the amino acid sequence of SEQ ID NO: 86; or (xii) a heavy chain variable region having at least 80%, for example, 85%, 88%, 90%, 92%, 95%, 96%, 97%, 98%, 99% or 100% sequence identity to the amino acid sequence of SEQ ID NO: 85 and a light chain variable region having at least 80%, for example, 85%, 88%, 90%, 92%, 95%, 96%, 97%, 98%, 99% or 100% sequence identity to the amino acid sequence of SEQ ID NO: 30; or (xiii) a heavy chain variable region having at least 80%, for example, 85%, 88%, 90%, 92%, 95%, 96%, 97%, 98%, 99% or 100% sequence identity to the amino acid sequence of SEQ ID NO: 85 and a light chain variable region having at least 80%, for example, 85%, 88%, 90%, 92%, 95%, 96%, 97%, 98%, 99% or 100% sequence identity to the amino acid sequence of SEQ ID NO: 86.

It is thus preferred that the antibody, or the antigen binding fragment thereof, comprises: (i) a heavy chain variable region having at least 80%, for example, 85%, 88%, 90%, 92%, 95%, 96%, 97%, 98%, 99% or 100% sequence identity to the amino acid sequence of SEQ ID NO: 13 and a light chain variable region having at least 80%, for example, 85%, 88%, 90%, 92%, 95%, 96%, 97%, 98%, 99% or 100% sequence identity to the amino acid sequence of SEQ ID NO: 14; or (ii) a heavy chain variable region having at least 80%, for example, 85%, 88%, 90%, 92%, 95%, 96%, 97%, 98%, 99% or 100% sequence identity to the amino acid sequence of SEQ ID NO: 29 and a light chain variable region having at least 80%, for example, 85%, 88%, 90%, 92%, 95%, 96%, 97%, 98%, 99% or 100% sequence identity to the amino acid sequence of SEQ ID NO: 30; (iii) or a heavy chain variable region having at least 80%, for example, 85%, 88%, 90%, 92%, 95%, 96%, 97%, 98%, 99% or 100% sequence identity to the amino acid sequence of SEQ ID NO: 45 and a light chain variable region having at least 80%, for example, 85%, 88%, 90%, 92%, 95%, 96%, 97%, 98%, 99% or 100% sequence identity to the amino acid sequence of SEQ ID NO: 46; or (iv) a heavy chain variable region having at least 80%, for example, 85%, 88%, 90%, 92%, 95%, 96%, 97%, 98%, 99% or 100% sequence identity to the amino acid sequence of SEQ ID NO: 61 and a light chain variable region having at least 80%, for example, 85%, 88%, 90%, 92%, 95%, 96%, 97%, 98%, 99% or 100% sequence identity to the amino acid sequence of SEQ ID NO: 62; or (v) a heavy chain variable region having at least 80%, for example, 85%, 88%, 90%, 92%, 95%, 96%, 97%, 98%, 99% or 100% sequence identity to the amino acid sequence of SEQ ID NO: 61 and a light chain variable region having at least 80%, for example, 85%, 88%, 90%, 92%, 95%, 96%, 97%, 98%, 99% or 100% sequence identity to the amino acid sequence of SEQ ID NO: 66; or (vi) a heavy chain variable region having at least 80%, for example, 85%, 88%, 90%, 92%, 95%, 96%, 97%, 98%, 99% or 100% sequence identity to the amino acid sequence of SEQ ID NO: 65 and a light chain variable region having at least 80%, for example, 85%, 88%, 90%, 92%, 95%, 96%, 97%, 98%, 99% or 100% sequence identity to the amino acid sequence of SEQ ID NO: 62; or (vii) a heavy chain variable region having at least 80%, for example, 85%, 88%, 90%, 92%, 95%, 96%, 97%, 98%, 99% or 100% sequence identity to the amino acid sequence of SEQ ID NO: 65 and a light chain variable region having at least 80%, for example, 85%, 88%, 90%, 92%, 95%, 96%, 97%, 98%, 99% or 100% sequence identity to the amino acid sequence of SEQ ID NO: 66; or (viii) a heavy chain variable region having at least 80%, for example, 85%, 88%, 90%, 92%, 95%, 96%, 97%, 98%, 99% or 100% sequence identity to the amino acid sequence of SEQ ID NO: 13 and a light chain variable region having at least 80%, for example, 85%, 88%, 90%, 92%, 95%, 96%, 97%, 98%, 99% or 100% sequence identity to the amino acid sequence of SEQ ID NO: 76; or (ix) a heavy chain variable region having at least 80%, for example, 85%, 88%, 90%, 92%, 95%, 96%, 97%, 98%, 99% or 100% sequence identity to the amino acid sequence of SEQ ID NO: 75 and a light chain variable region having at least 80%, for example, 85%, 88%, 90%, 92%, 95%, 96%, 97%, 98%, 99% or 100% sequence identity to the amino acid sequence of SEQ ID NO: 14; or (x) a heavy chain variable region having at least 80%, for example, 85%, 88%, 90%, 92%, 95%, 96%, 97%, 98%, 99% or 100% sequence identity to the amino acid sequence of SEQ ID NO: 75 and a light chain variable region having at least 80%, for example, 85%, 88%, 90%, 92%, 95%, 96%, 97%, 98%, 99% or 100% sequence identity to the amino acid sequence of SEQ ID NO: 76; or (xi) a heavy chain variable region having at least 80%, for example, 85%, 88%, 90%, 92%, 95%, 96%, 97%, 98%, 99% or 100% sequence identity to the amino acid sequence of SEQ ID NO: 29 and a light chain variable region having at least 80%, for example, 85%, 88%, 90%, 92%, 95%, 96%, 97%, 98%, 99% or 100% sequence identity to the amino acid sequence of SEQ ID NO: 86; or (xii) a heavy chain variable region having at least 80%, for example, 85%, 88%, 90%, 92%, 95%, 96%, 97%, 98%, 99% or 100% sequence identity to the amino acid sequence of SEQ ID NO: 85 and a light chain variable region having at least 80%, for example, 85%, 88%, 90%, 92%, 95%, 96%, 97%, 98%, 99% or 100% sequence identity to the amino acid sequence of SEQ ID NO: 30; or (xiii) a heavy chain variable region having at least 80%, for example, 85%, 88%, 90%, 92%, 95%, 96%, 97%, 98%, 99% or 100% sequence identity to the amino acid sequence of SEQ ID NO: 85 and a light chain variable region having at least 80%, for example, 85%, 88%, 90%, 92%, 95%, 96%, 97%, 98%, 99% or 100% sequence identity to the amino acid sequence of SEQ ID NO: 86.

More preferably, the antibody or the antigen binding fragment comprises: (i) a heavy chain variable region comprising the amino acid sequence of SEQ ID NO: 13 and a light chain variable region comprising the amino acid sequence of SEQ ID NO: 14; or (ii) a heavy chain variable region comprising the amino acid sequence of SEQ ID NO: 29 and a light chain variable region comprising the amino acid sequence of SEQ ID NO: 30; (iii) or a heavy chain variable region comprising the amino acid sequence of SEQ ID NO: 45 and a light chain variable region comprising the amino acid sequence of SEQ ID NO: 46; or (iv) a heavy chain variable region comprising the amino acid sequence of SEQ ID NO: 61 and a light chain variable region comprising the amino acid sequence of SEQ ID NO: 62; or (v) a heavy chain variable region comprising the amino acid sequence of SEQ ID NO: 61 and a light chain variable region comprising the amino acid sequence of SEQ ID NO: 66; or (vi) a heavy chain variable region comprising the amino acid sequence of SEQ ID NO: 65 and a light chain variable region comprising the amino acid sequence of SEQ ID NO: 62; or (vii) a heavy chain variable region comprising the amino acid sequence of SEQ ID NO: 65 and a light chain variable region comprising the amino acid sequence of SEQ ID NO: 66; or (viii) a heavy chain variable region comprising the amino acid sequence of SEQ ID NO: 13 and a light chain variable region comprising the amino acid sequence of SEQ ID NO: 76; or (ix) a heavy chain variable region comprising the amino acid sequence of SEQ ID NO: 75 and a light chain variable region comprising the amino acid sequence of SEQ ID NO: 14; or (x) a heavy chain variable region comprising the amino acid sequence of SEQ ID NO: 75 and a light chain variable region comprising the amino acid sequence of SEQ ID NO: 76; or (xi) a heavy chain variable region comprising the amino acid sequence of SEQ ID NO: 29 and a light chain variable region comprising the amino acid sequence of SEQ ID NO: 86; or (xii) a heavy chain variable region comprising the amino acid sequence of SEQ ID NO: 85 and a light chain variable region comprising the amino acid sequence of SEQ ID NO: 30; or (xiii) a heavy chain variable region comprising the amino acid sequence of SEQ ID NO: 85 and a light chain variable region comprising the amino acid sequence of SEQ ID NO: 86.

In another embodiment of the invention, the invention comprises an antibody, or an antigen binding fragment thereof, that neutralizes infection of RSV A and RSV B and comprises a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 45 and a light chain variable region comprising the amino acid sequence of SEQ ID NO: 46; or a heavy chain variable region comprising the amino acid sequence of SEQ ID NO: 61 and a light chain variable region comprising the amino acid sequence of SEQ ID NO: 62; or a heavy chain variable region comprising the amino acid sequence of SEQ ID NO: 61 and a light chain variable region comprising the amino acid sequence of SEQ ID NO: 66; or a heavy chain variable region comprising the amino acid sequence of SEQ ID NO: 65 and a light chain variable region comprising the amino acid sequence of SEQ ID NO: 62; or a heavy chain variable region comprising the amino acid sequence of SEQ ID NO: 65 and a light chain variable region comprising the amino acid sequence of SEQ ID NO: 66; or a heavy chain variable region comprising the amino acid sequence of SEQ ID NO: 13 and a light chain variable region comprising the amino acid sequence of SEQ ID NO: 76; or a heavy chain variable region comprising the amino acid sequence of SEQ ID NO: 75 and a light chain variable region comprising the amino acid sequence of SEQ ID NO: 14; or a heavy chain variable region comprising the amino acid sequence of SEQ ID NO: 75 and a light chain variable region comprising the amino acid sequence of SEQ ID NO: 76; or a heavy chain variable region comprising the amino acid sequence of SEQ ID NO: 29 and a light chain variable region comprising the amino acid sequence of SEQ ID NO: 86; or a heavy chain variable region comprising the amino acid sequence of SEQ ID NO: 85 and a light chain variable region comprising the amino acid sequence of SEQ ID NO: 30; or a heavy chain variable region comprising the amino acid sequence of SEQ ID NO: 85 and a light chain variable region comprising the amino acid sequence of SEQ ID NO: 86.

Examples of antibodies of the invention include, but are not limited to, HMB2435, HMB2435 variant 2, HMB2435 variant 3, HMB2435 variant 4, HMB2437, HMB2437 variant 2, HMB2437 variant 3, HMB2437 variant 4, HMB2416, HMB2432 variant 1, HMB2432 variant 2, HMB2432 variant 3 or HMB2432 variant 4. Preferably, the antibody, or the antigen binding fragment thereof, is according to gHMB2435, gHMB2435 variant 2, gHMB2435 variant 3, gHMB2435 variant 4, gHMB2437, gHMB2437 variant 2, gHMB2437 variant 3, gHMB2437 variant 4, gHMB2416, gHMB2432 variant 1, gHMB2432 variant 2, gHMB2432 variant 3 or gHMB2432 variant 4.

The invention further comprises an antibody, or fragment thereof, that binds to the same epitope as an antibody or antigen binding fragment of the invention, or an antibody that competes with an antibody or antigen binding fragment of the invention.

Preferably, the antibody, or the antigen binding fragment thereof, according to the present invention that binds to the same epitope as the antibody as described above, (i) neutralizes infection of both group A and group B RSV, but does not neutralize infection of MPV; (ii) specifically binds the pre-fusion F protein of RSV, but not the post-fusion RSV F protein; and (iii) has an isoelectric point (pI) of 7.5 or higher.

Antibodies of the invention also include hybrid antibody molecules that neutralize infection of group A and group B RSV and that comprise one or more CDRs from an antibody of the invention and one or more CDRs from another antibody to the same epitope. In one embodiment, such hybrid antibodies comprise three CDRs from an antibody of the invention and three CDRs from another antibody to the same epitope. Exemplary hybrid antibodies comprise (i) the three heavy chain CDRs from an antibody of the invention and the three light chain CDRs from another antibody to the same epitope, or (ii) the three light chain CDRs from an antibody of the invention and the three heavy chain CDRs from another antibody to the same epitope.

Variant antibodies are also included within the scope of the invention. Thus, variants of the sequences recited in the application are also included within the scope of the invention. Such variants include natural variants generated by somatic mutation in vivo during the immune response or in vitro upon culture of immortalized B cell clones. Alternatively, variants may arise due to the degeneracy of the genetic code or may be produced due to errors in transcription or translation.

Further variants of the antibody sequences having improved affinity and/or potency may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

In one embodiment variant antibody sequences may share 70% or more (i.e. 75%, 80%, 85%, 88%, 90%, 92%, 95%, 96%, 97%, 98%, 99% or more) amino acid sequence identity with the sequences recited in the application. Such variants in general have a greater homology to the sequences listed herein in the CDRs of the $V_H$ and $V_L$ than in the framework region. As is known to one of skill in the art, mutations are more tolerated, i.e., limited or no loss of function (e.g., specificity or neutralization ability) in the framework regions than in the CDRs. In one embodiment, the invention comprises an antibody, or an antigen binding fragment thereof, wherein the variation from the sequences provided herein is in the framework region(s) of the antibody or in the nucleic acid residues that encode the framework region(s) of the antibody.

In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

In another aspect, the invention also includes nucleic acid sequences encoding part or all of the light and heavy chains and CDRs of the antibodies of the present invention. Provided herein are nucleic acid sequences encoding part or all of the light and heavy chains and CDRs of exemplary antibodies of the invention. Table 2 provides the SEQ ID numbers for the nucleic acid sequences encoding the heavy chain and light chain variable regions of some examples of antibodies of the invention. Table 3 provides the SEQ ID numbers for the nucleic acid sequences encoding the CDRs of some examples of the antibodies of the invention. Due to the redundancy of the genetic code, variants of these nucleic acid sequences will exist that encode the same amino acid sequences.

Thus, the present invention also comprises a nucleic acid molecule comprising a polynucleotide encoding the antibody, or the antigen binding fragment thereof, according to the present invention.

TABLE 3

SEQ ID Numbers for CDR Polynucleotides of
Antibodies that Neutralize RSV A and RSV B.

| | SEQ ID NOs. for CDR Polynucleotides | | | | | |
|---|---|---|---|---|---|---|
| | CDRH1 | CDRH2 | CDRH3 | CDRL1 | CDRL2 | CDRL3 |
| HMB2435 | 7 | 8 | 9 | 10 | 11 | 12 |
| HMB2437 | 23 | 24 | 25 | 26 | 27 | 28 |
| HMB2416 | 39 | 40 | 41 | 42 | 43 | 44 |
| HMB2432 variant 1 | 55 | 56 | 57 | 58 | 59 | 60 |
| HMB2432 variant 2 | 55 | 56 | 57 | 58 | 59 | 60 |
| HMB2432 variant 3 | 55 | 56 | 57 | 58 | 59 | 60 |
| HMB2432 variant 4 | 55 | 56 | 57 | 58 | 59 | 60 |
| HMB2435 variant 2 | 7 | 8 | 9 | 72 | 73 | 74 |
| HMB2435 variant 3 | 69 | 70 | 71 | 10 | 11 | 12 |
| HMB2435 variant 4 | 69 | 70 | 71 | 72 | 73 | 74 |
| HMB2437 variant 2 | 23 | 24 | 25 | 82 | 83 | 84 |
| HMB2437 variant 3 | 79 | 80 | 81 | 26 | 27 | 28 |
| HMB2437 variant 4 | 79 | 80 | 81 | 82 | 83 | 84 |

Preferably, the polynucleotide sequence of the nucleic acid molecule according to the invention is at least 75% identical to the nucleic acid sequence of any one of SEQ ID NOs: 7-12, 15, 16, 23-28, 31, 32, 39-44, 47, 48, 55-60, 63, 64, 67, 68, 69-74, 77, 78, 79-84, 87, or 88. Preferably, the nucleotide sequence of the nucleic acid molecule according to the invention is according to any one of SEQ ID NOs: 7-12, 15, 16, 23-28, 31, 32, 39-44, 47, 48, 55-60, 63, 64, 67, 68, 69-74, 77, 78, 79-84, 87, or 88, or sequence variants thereof.

In one embodiment, nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding the variable region of a heavy or light chain of an antibody of the invention. In another embodiment, a nucleic acid sequence of the invention has the sequence of a nucleic acid encoding a heavy or light chain CDR of an antibody of the invention. For example, a nucleic acid sequence according to the invention comprises a sequence that is at least 75%, at least 80%, at least 85%, at least 88%, at least 90%, at least 92%, at least 95%, at least 96%, at least 97%, at least 98% or at least 99% identical to the nucleic acid sequences of SEQ ID NOs: 7-12, 15, 16, 23-28, 31, 32, 39-44, 47, 48, 55-60, 63, 64, 67, 68, 69-74, 77, 78, 79-84, 87 or 88.

In yet another embodiment, nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a heavy or light chain of an antibody of the invention as provided in FIGS. 7, 8, 9, 10A and 10B.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

Further included within the scope of the invention are vectors, for example, expression vectors, comprising a nucleic acid sequence according to the invention. Preferably, a vector comprises a nucleic acid molecule according to the invention, for example a nucleic acid molecule as described above.

Cells transformed with such vectors are also included within the scope of the invention. Examples of such cells include but are not limited to, eukaryotic cells, e.g., yeast cells, animal cells or plant cells. In one embodiment the cells are mammalian, e.g., human, CHO, HEK293T, PER.C6, NS0, myeloma or hybridoma cells. Accordingly, the present invention also relates to a cell expressing the antibody, or the antigen binding fragment thereof, according to the present invention; or comprising the vector according to the present invention.

The invention also relates to monoclonal antibodies that bind to an epitope capable of binding the antibodies or antigen binding fragments of the invention. Accordingly, the present invention comprises an isolated or purified immunogenic polypeptide comprising an epitope that specifically binds to the antibody, or the antigen binding fragment thereof, according to the present invention.

The invention provides novel epitopes to which the neutralizing antibodies of the invention bind. These epitopes are found on the RSV pre-fusion, but not post-fusion, F protein. In one embodiment, the antibodies, or the antigen binding fragments thereof, bind RSV pre-fusion F protein and not RSV post-fusion F protein. In another embodiment, the antibodies, or the antigen binding fragments thereof, bind RSV pre-fusion F protein and not MPV or PVM pre-fusion F protein. In a preferred embodiment the antibodies, or the antigen binding fragments thereof, bind RSV pre-fusion F protein and neither RSV post-fusion F protein nor MPV or PVM pre-fusion F protein.

The epitopes to which the antibodies of the invention bind may be linear (continuous) or conformational (discontinuous). In one embodiment, the antibodies and antibody fragments of the invention bind a conformational epitope. In another embodiment, the conformational epitope is present only under non-reducing conditions.

In another embodiment, the epitope to which the antibodies of the invention bind is distinct from antigenic site I, antigenic site II, antigenic site IV as defined on the RSV post-fusion F protein and from antigenic site S1 as defined herein on the RSV pre-fusion F protein. In yet another embodiment, the antibodies and the antigen binding fragments of the invention do not cross-compete with palivizumab for binding to the F protein of RSV.

Four antigenic sites (S1, S2, S3 and S5) on the pre-fusion F protein of RSV have been identified herein. In one embodiment, the invention provides an antibody or antigen binding fragment thereof that specifically binds antigenic site S5 of the RSV A or RSV B pre-fusion F protein. In another embodiment, the invention provides an antibody or antigen binding fragment thereof that specifically binds antigenic site S2 of the RSV A or RSV B pre-fusion F protein. In another embodiment, the invention provides an antibody or antigen binding fragment thereof that specifically binds antigenic site S3 of the RSV A or RSV B pre-fusion F protein. In another embodiment, the invention provides an antibody or antigen binding fragment thereof that specifically binds an antigenic site that overlaps sites S2 and S3 of the RSV A or RSV B pre-fusion F protein. In yet another embodiment, the invention provides an antibody or antigen binding fragment thereof that does not specifically bind antigenic site S1 of the RSV A or RSV B pre-fusion F protein.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labeled with an analytically-detectable reagent such as a radioisotope, a fluorescent molecule or an enzyme. The antibodies may also be used for the molecular identification and characterization (epitope mapping) of antigens.

Antibodies of the invention can be coupled to a drug for delivery to a treatment site or coupled to a detectable label to facilitate imaging of a site comprising cells of interest, such as cells infected with RSV A or RSV B or both RSV A and RSV B. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (an epitope or RSV A or RSV B or both) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like. (See U.S. Pat. No. 3,766,162; U.S. Pat. No. 3,791,932; U.S. Pat. No. 3,817,837; and U.S. Pat. No. 4,233,402 for example).

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, or antibody fragment thereof, can be conjugated to a second antibody, or antibody fragment thereof, to form an antibody heteroconjugate as described in U.S. Pat. No. 4,676,980. In addition, linkers may be used between the labels and the antibodies of the invention (e.g., U.S. Pat. No. 4,831,175). Antibodies or, antigen-binding fragments thereof may be directly labeled with radioactive iodine, indium, yttrium, or other radioactive particle known in the art (e.g., U.S. Pat. No. 5,595,721). Treatment may consist of a combination of treatment with conjugated and non-conjugated antibodies administered simultaneously or subsequently (e.g., WO00/52031; WO00/52473).

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. No. 4,766,106; U.S. Pat. No. 4,179,337; U.S. Pat. No. 4,495,285 and U.S. Pat. No. 4,609,546. In some embodiments the polymers may be selected from polyoxyethylated polyols and polyethylene glycol (PEG). PEG is soluble in water at room temperature and has the general formula: R(O—CH2-CH2)nO—R where R can be hydrogen, or a protective group such as an alkyl or alkanol group. In one embodiment the protective group may have between 1 and 8 carbons. In a further embodiment the protective group is methyl. The symbol n is a positive integer. In one embodiment n is between 1 and 1,000. In another embodiment n is between 2 and 500. In one embodiment the PEG has an average molecular weight between 1,000 and 40,000. In a further embodiment the PEG has a molecular weight between 2,000 and 20,000. In yet a further embodiment the PEG has a molecular weight between 3,000 and 12,000. In one embodiment PEG has at least one hydroxy group. In another embodiment the PEG has a terminal hydroxy group. In yet another embodiment it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. In some embodiments POG has a molecular weight in the same range as PEG. Another drug delivery system that can be used for increasing circulatory half-life is the liposome. Methods of preparing liposome delivery systems are known to one of skill in the art. Other drug delivery systems are known in the art and are described in, for example, referenced in Poznansky et al. (1980) and Poznansky (1984).

Antibodies of the invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies of the invention may be immunogenic in non-human (or heterologous) hosts e.g., in mice. In particular, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanization or from xeno-mice.

Antibodies of the invention can be of any isotype (e.g., IgA, IgG, IgM i.e. an a, y or p heavy chain), but will generally be IgG. Within the IgG isotype, antibodies may be IgG1, IgG2, IgG3 or IgG4 subclass. Antibodies of the invention may have a κ or a λ light chain.

Production of Antibodies

Antibodies according to the invention can be made by any method known in the art. For example, the general methodology for making monoclonal antibodies using hybridoma technology is well known (Kohler, G. and Milstein, C. 1975; Kozbar et al. 1983). In one embodiment, the alternative EBV immortalization method described in WO2004/076677 is used.

Using the method described in WO 2004/076677, B cells producing the antibody of the invention can be transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Using the method described in WO 2010/046775, plasma cells can be cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL regions of the antibodies can be amplified by RT-PCR, sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

It is known in the art that physical aggregation of monoclonal antibodies is pH dependent, since pH has an impact on the tertiary structure conformation as well as the net charge of the protein, thus affecting net protein-protein interactions (Ejima et al., 2007, *Proteins Structural Function Bioinformatics*, 66, 954-962). Aggregation of monoclonal antibodies is favored when the working pH is near to the isoelectric point of the antibody. While solution environment higher than pH 7.0 can promote deamidation of the asparagine residues, disulfide exchange and aggregation, lower pH values (pH 4 and below) can promote isomerization, hydrolysis and fragmentation (Zheng et al., 2006, *Internal Journal of Pharmacology*, 308, 46-51). In general currently marketed antibodies have a pI between 7.4 to 8.6 and are formulated in the pH range of 5.0 to 7.2, with most of the antibodies being formulated at slightly acidic pH. The antibodies provided herein as examples of antibodies of the invention have a pI between about 8.1 and 8.5, making them excellent candidates for production and formulation in marketable quantities.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

The present invention also provides a process for the production of an antibody molecule according to the present invention comprising culturing a host cell comprising a vector encoding a nucleic acid of the present invention under conditions suitable for expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides. Alternatively, antibodies according to the invention may be produced by (i) expressing a nucleic acid sequence according to the invention in a host cell, and (ii) isolating the expressed antibody product. Additionally, the method may include (iii) purifying the isolated antibody. Transformed B cells and cultured plasma cells may be screened for those producing antibodies of the desired specificity or function.

The screening step may be carried out by any immunoassay, e.g., ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g., to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured plasma cells can be isolated, cloned and expressed in HEK293T cells or other known host cells using methods known in the art.

The immortalized B cell clones or the transfected hostcells of the invention can be used in various ways e.g., as a source of monoclonal antibodies, as a source of nucleic acid (DNA or mRNA) encoding a monoclonal antibody of interest, for research, etc.

The invention provides a composition comprising immortalized B memory cells or transfected host cells that produce antibodies that neutralize infection of group A RSV, group B RSV or both group A and group B RSV.

The immortalized B cell clone or the cultured plasma cells of the invention may also be used as a source of nucleic acid for the cloning of antibody genes for subsequent recombinant expression. Expression from recombinant sources is more common for pharmaceutical purposes than expression from B cells or hybridomas e.g., for reasons of stability, reproducibility, culture ease, etc.

Thus the invention provides a method for preparing a recombinant cell, comprising the steps of: (i) obtaining one or more nucleic acids (e.g., heavy and/or light chain mRNAs) from the B cell clone or the cultured plasma cells that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured plasma cells that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimize transcription and/or translation regulatory sequences.

The invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured plasma cell of the invention. Thus the procedures for first preparing the nucleic acid(s) and then using it to transfect a host cell can be performed at different times by different people in different places (e.g., in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells or plasma cells are well known in the art (e.g., see Chapter 4 of Kuby Immunology, 4th edition, 2000).

The transfected host cell may be a eukaryotic cell, including yeast and animal cells, particularly mammalian cells (e.g., CHO cells, NS0 cells, human cells such as PER.C6 or HKB-11 cells, myeloma cells), as well as plant cells. Preferred expression hosts can glycosylate the antibody of the invention, particularly with carbohydrate structures that are not themselves immunogenic in humans. In one embodiment the transfected host cell may be able to grow in serum-free media. In a further embodiment the transfected host cell may be able to grow in culture without the presence of animal-derived products. The transfected host cell may also be cultured to give a cell line.

The invention also provides a method for preparing one or more nucleic acid molecules (e.g., heavy and light chain genes) that encode an antibody of interest, comprising the steps of: (i) preparing an immortalized B cell clone or culturing plasma cells according to the invention; (ii) obtaining from the B cell clone or the cultured plasma cells nucleic acid that encodes the antibody of interest. Further, the invention provides a method for obtaining a nucleic acid sequence that encodes an antibody of interest, comprising the steps of: (i) preparing an immortalized B cell clone or culturing plasma cells according to the invention; (ii) sequencing nucleic acid from the B cell clone or the cultured plasma cells that encodes the antibody of interest.

The invention also provides a method of preparing nucleic acid molecule(s) that encode an antibody of interest, comprising the step of obtaining the nucleic acid that was obtained from a transformed B cell clone or cultured plasma cells of the invention. Thus the procedures for first obtaining the B cell clone or the cultured plasma cell, and then obtaining nucleic acid(s) from the B cell clone or the cultured plasma cells can be performed at different times by different people in different places (e.g., in different countries).

The invention provides a method for preparing an antibody (e.g., for pharmaceutical use), comprising the steps of: (i) obtaining and/or sequencing one or more nucleic acids (e.g., heavy and light chain genes) from the selected B cell clone or the cultured plasma cells expressing the antibody of interest; (ii) inserting the nucleic acid(s) into or using the nucleic acid(s) sequence(s) to prepare an expression vector; (iii) transfecting a host cell that can express the antibody of interest; (iv) culturing or sub-culturing the transfected host cells under conditions where the antibody of interest is expressed; and, optionally, (v) purifying the antibody of interest.

The invention also provides a method of preparing an antibody comprising the steps of: culturing or sub-culturing a transfected host cell population under conditions where the antibody of interest is expressed and, optionally, purifying the antibody of interest, wherein said transfected host cell population has been prepared by (i) providing nucleic acid(s) encoding a selected antibody of interest that is produced by a B cell clone or cultured plasma cells prepared as described above, (ii) inserting the nucleic acid(s) into an expression vector, (iii) transfecting the vector in a host cell that can express the antibody of interest, and (iv) culturing or sub-culturing the transfected host cell comprising the inserted nucleic acids to produce the antibody of interest. Thus the procedures for first preparing the recombinant host cell and then culturing it to express antibody can be performed at very different times by different people in different places (e.g., in different countries).

Epitopes

As mentioned above, the antibodies of the invention can be used to map the epitopes to which they bind. The invention provides novel epitopes to which the neutralizing antibodies of the invention bind. These epitopes are found on the pre-fusion, but not post-fusion, F protein. In one embodiment, the antibodies, or antigen binding fragments thereof, bind RSV pre-fusion F protein and not RSV post-fusion F protein. In another embodiment, the antibodies, or antigen binding fragments thereof, bind RSV pre-fusion F protein and not MPV or PVM pre-fusion F protein.

The epitopes to which the antibodies of the invention bind may be linear (continuous) or conformational (discontinuous). In one embodiment, the antibodies and antibody fragments of the invention bind a conformational epitope. In another embodiment, the conformational epitope is present only under non-reducing conditions.

In another embodiment, the epitope to which the antibodies of the invention bind is distinct from antigenic site I, antigenic site II, antigenic site IV as defined on the RSV post-fusion F protein and from antigenic site S1 as defined herein on the RSV pre-fusion F protein. In yet another embodiment, the antibodies and antigen binding fragments of the invention do not cross-compete with palivizumab for binding to the F protein of RSV.

Four antigenic sites (S1, S2, S3 and S5) on the pre-fusion F protein of RSV have been identified herein. In one embodiment, the invention provides an antibody or antigen binding fragment thereof that specifically binds antigenic site S5 of the RSV A or RSV B pre-fusion F protein. In another embodiment, the invention provides an antibody or antigen binding fragment thereof that specifically binds antigenic site S2 of the RSV A or RSV B pre-fusion F protein. In another embodiment, the invention provides an antibody or antigen binding fragment thereof that specifically binds antigenic site S3 of the RSV A or RSV B pre-fusion F protein. In another embodiment, the invention provides an antibody or antigen binding fragment thereof that specifically binds an antigenic site that overlaps sites S2 and S3 of the RSV A or RSV B pre-fusion F protein. In yet another embodiment, the invention provides an antibody or antigen binding fragment thereof that does not specifically bind antigenic site S1 of the RSV A or RSV B pre-fusion F protein.

The polypeptides that bind to the antibodies of the present invention may have a number of uses. The polypeptides and polypeptide variants thereof in purified or synthetic form can be used to raise immune responses (i.e., as a vaccine, or for the production of antibodies for other uses) or for screening sera for antibodies that immunoreact with the epitope or mimotopes thereof. In one embodiment such polypeptides or polypeptide variants, or antigen comprising such polypeptides or polypeptide variants may be used as a vaccine for raising an immune response that comprises antibodies of the same quality as those described in the present invention.

Furthermore, the present invention also relates to the use of the antibody, or the antigen binding fragment thereof, according to the present invention, for monitoring the quality of anti-group A RSV or anti-group B RSV vaccines by checking that the antigen of said vaccine contains the specific epitope in the correct conformation.

The antibodies and antibody fragments of the invention can also be used in a method of monitoring the quality of vaccines. In particular the antibodies can be used to check that the antigen in a vaccine contains the correct immunogenic epitope in the correct conformation. The use of an antibody of the invention, or an antigen binding fragment thereof, for monitoring the quality of a vaccine against RSV or MPV or both RSV and MPV by, for example, checking that the antigen of said vaccine contains the specific epitope in the correct conformation is also contemplated to be within the scope of the invention.

The polypeptides that bind to the antibodies of the present invention may also be useful in screening for ligands that bind to said polypeptides. Such ligands, include but are not limited to antibodies; including those from camels, sharks and other species, fragments of antibodies, peptides, phage display technology products, aptamers, adnectins or fragments of other viral or cellular proteins, may block the epitope and so prevent infection. Such ligands are encompassed within the scope of the invention.

Pharmaceutical Compositions

The invention provides a pharmaceutical composition comprising one or more of: the antibodies or antibody fragments of the invention; nucleic acid encoding such antibodies or fragments; vectors encoding the nucleic acids; or polypeptides recognized by the antibodies or antigen binding fragment of the invention. The pharmaceutical composition may also contain a pharmaceutically acceptable carrier or excipient. Preferably, the pharmaceutical composition comprises the antibody, or the antigen binding fragment thereof, according to the present invention, the nucleic acid according to the present invention, the vector according to the present invention, the cell according to the present invention, or the immunogenic polypeptide according to the present invention, and a pharmaceutically acceptable excipient, diluent or carrier.

Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid. Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hypossprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms. Preferably, the composition according to the invention is administered to a subject before an RSV-infection has taken place. Alternatively, the composition according to the invention is administered when a subject is already infected with RSV.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, like Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody can be provided in kit form with sterile water or a sterile buffer.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Pharmaceutical compositions will include an effective amount of one or more antibodies of the invention and/or a polypeptide comprising an epitope that binds an antibody of the invention i.e., an amount that is sufficient to treat, ameliorate, attenuate or prevent a desired disease or condition, or to exhibit a detectable therapeutic effect. Therapeutic effects also include reduction or attenuation in pathogenic potency or physical symptoms. The precise effective amount for any particular subject will depend upon their size, weight, and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.01 mg/kg to about 50 mg/kg, or about 0.05 mg/kg to about 10 mg/kg of the compositions of the present invention in the individual to which it is administered. Known antibody-based pharmaceuticals provide guidance in this respect e.g., Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; etc.

Preferably, a pharmaceutical composition according to the present invention comprises a first antibody or an antigen binding fragment thereof, and a second antibody, or an antigen binding fragment thereof, wherein the first antibody, or the antigen binding fragment thereof, is the antibody, or the antigen binding fragment thereof, according to the present invention, and the second antibody neutralizes infection of RSV or MPV or PVM or any combination of RSV, MPV and PVM.

In one embodiment compositions can include more than one or more (e.g., 2, 3, etc.) antibodies of the invention to provide an additive or synergistic therapeutic effect. In another embodiment, the composition may comprise one or more (e.g., 2, 3, etc.) antibodies of the invention and one or more (e.g., 2, 3, etc.) additional antibodies against RSV, MPV or both RSV and MPV. Further, the administration of antibodies of the invention together with antibodies specific to other pathogens, for example, influenza A or influenza B virus, are within the scope of the invention. The antibodies of the invention can be administered either combined/simultaneously or at separate times from antibodies of specific to pathogens other than RSV.

In another embodiment, the invention provides a pharmaceutical composition comprising two or more antibodies, wherein the first antibody is an antibody of the invention as described herein and the second antibody is specific for RSV, MPV or both RSV and MPV or a different pathogen that may have co-infected the subject to whom the pharmaceutical composition is being administered.

Examples of antibodies of the invention specific for, and that neutralize RSV include, but are not limited to, HMB2435, HMB2435 variant 2, HMB2435 variant 3, HMB2435 variant 4, HMB2437, HMB2437 variant 2, HMB2437 variant 3, HMB2437 variant 4, HMB2416, HMB2432 variant 1, HMB2432 variant 2, HMB2432 variant 3 or HMB2432 variant 4. Preferably, the antibody, or the antigen binding fragment thereof, is according to gHMB2435, gHMB2435 variant 2, gHMB2435 variant 3, gHMB2435 variant 4, gHMB2437, gHMB2437 variant 2, gHMB2437 variant 3, gHMB2437 variant 4, gHMB2416, gHMB2432 variant 1, gHMB2432 variant 2, gHMB2432 variant 3 or gHMB2432 variant 4.

In one embodiment, the invention provides a pharmaceutical composition comprising the antibody HMB2435 or an antigen binding fragment thereof, and a pharmaceutically acceptable carrier. In another embodiment, the invention provides a pharmaceutical composition comprising the antibody HMB2435 variant 2 or an antigen binding fragment thereof, and a pharmaceutically acceptable carrier. In another embodiment, the invention provides a pharmaceutical composition comprising the antibody HMB2435 variant 3 or an antigen binding fragment thereof, and a pharmaceutically acceptable carrier. In another embodiment, the invention provides a pharmaceutical composition comprising the antibody HMB2435 variant 4 or an antigen binding fragment thereof, and a pharmaceutically acceptable carrier. In another embodiment, the invention provides a pharmaceutical composition comprising the antibody HMB2437 or an antigen binding fragment thereof, and a pharmaceutically acceptable carrier. In another embodiment, the invention provides a pharmaceutical composition comprising the antibody HMB2437 variant 2 or an antigen binding fragment thereof, and a pharmaceutically acceptable carrier. In another embodiment, the invention provides a pharmaceutical composition comprising the antibody HMB2437 variant 3 or an antigen binding fragment thereof, and a pharmaceutically acceptable carrier. In another embodiment, the invention provides a pharmaceutical composition comprising the antibody HMB2437 variant 4 or an antigen binding fragment thereof, and a pharmaceutically acceptable carrier. In another embodiment, the invention provides a pharmaceutical composition comprising the antibody HMB2416 or an antigen binding fragment thereof, and a pharmaceutically acceptable carrier. In another embodiment, the invention provides a pharmaceutical composition comprising the antibody HMB2432 variant 1 or an antigen binding fragment thereof, and a pharmaceutically acceptable carrier. In another embodiment, the invention provides a pharmaceutical composition comprising the antibody HMB2432 variant 2 or an antigen binding fragment thereof, and a pharmaceutically acceptable carrier. In another embodiment, the invention provides a pharmaceutical composition comprising the antibody HMB2432 variant 3 or an antigen binding fragment thereof, and a pharmaceutically acceptable carrier. In another embodiment, the invention provides a pharmaceutical composition comprising the antibody HMB2432 variant 4 or an antigen binding fragment thereof, and a pharmaceutically acceptable carrier.

In one embodiment, the invention provides a pharmaceutical composition comprising an antibody, or an antigen binding fragment thereof, according to gHMB2435 and a pharmaceutically acceptable carrier. In another embodiment, the invention provides a pharmaceutical composition comprising an antibody, or an antigen binding fragment thereof, according to gHMB2435 variant 2 and a pharmaceutically acceptable carrier. In another embodiment, the invention provides a pharmaceutical composition comprising an antibody, or an antigen binding fragment thereof, according to gHMB2435 variant 3 and a pharmaceutically acceptable carrier. In a preferred embodiment, the invention provides a pharmaceutical composition comprising an antibody, or an antigen binding fragment thereof, according to gHMB2435 variant 4 and a pharmaceutically acceptable carrier. In another embodiment, the invention provides a pharmaceutical composition comprising an antibody, or an antigen binding fragment thereof, according to gHMB2437 and a pharmaceutically acceptable carrier. In another embodiment, the invention provides a pharmaceutical composition comprising an antibody, or an antigen binding fragment thereof, according to gHMB2437 variant 2 and a pharmaceutically acceptable carrier. In another embodiment, the invention provides a pharmaceutical composition comprising an antibody, or an antigen binding fragment thereof, according to gHMB2437 variant 3 and a pharmaceutically acceptable carrier. In another embodiment, the invention provides a pharmaceutical composition comprising an antibody, or an antigen binding fragment thereof, according to gHMB2437 variant 4, and a pharmaceutically acceptable carrier. In another embodiment, the invention provides a pharmaceutical composition comprising an antibody, or an antigen binding fragment thereof, according to gHMB2416, and a pharmaceutically acceptable carrier. In another embodiment, the invention provides a pharmaceutical composition comprising an antibody, or an antigen binding fragment thereof, according to gHMB2432 variant 1, and a pharmaceutically acceptable carrier. In another embodiment, the invention provides a pharmaceutical composition comprising an antibody, or an antigen binding fragment thereof, according to gHMB2432 variant 2, and a pharmaceutically acceptable carrier. In another embodiment, the invention provides a pharmaceutical composition comprising an antibody, or an antigen binding fragment thereof, according to gHMB2432 variant 3, and a pharmaceutically acceptable carrier. In another embodiment, the invention provides a pharmaceutical composition comprising an antibody, or an antigen binding fragment thereof, according to gHMB2432 variant 4, and a pharmaceutically acceptable carrier.

Antibodies of the invention may be administered (either combined or separately) with other therapeutics e.g., with chemotherapeutic compounds, with radiotherapy, etc. In one embodiment, the therapeutic compounds include anti-viral compounds such as Tamiflu™. Such combination therapy provides an additive or synergistic improvement in therapeutic efficacy relative to the individual therapeutic agents when administered alone. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Antibodies may be administered to those subjects who have previously shown no response, i.e., have been shown to be refractive to treatment for RSV infection. Such treatment may include previous treatment with an anti-viral agent. This may be due to, for example, infection with an anti-viral resistant strain of RSV A, RSV B or both RSV A and RSV B.

In one embodiment, a composition of the invention may include antibodies of the invention, wherein the antibodies may make up at least 50% by weight (e.g., 60%, 70%, 75%, 80%, 85%, 90%, 95%, 97%, 98%, 99% or more) of the total protein in the composition. In such a composition, the antibodies are in purified form.

The invention provides a method of preparing a pharmaceutical composition comprising the steps of: (i) preparing an antibody of the invention; and (ii) admixing the purified antibody with one or more pharmaceutically-acceptable carriers.

In another embodiment, a method of preparing a pharmaceutical composition comprises the step of: admixing an antibody with one or more pharmaceutically-acceptable carriers, wherein the antibody is a monoclonal antibody that was obtained from a transformed B cell or a cultured plasma cell of the invention. Thus the procedures for first obtaining the monoclonal antibody and then preparing the pharmaceutical can be performed at very different times by different people in different places (e.g., in different countries).

As an alternative to delivering antibodies or B cells for therapeutic purposes, it is possible to deliver nucleic acid (typically DNA) that encodes the monoclonal antibody (or active fragment thereof) of interest derived from the B cell or the cultured plasma cells to a subject, such that the nucleic acid can be expressed in the subject in situ to provide a desired therapeutic effect. Suitable gene therapy and nucleic acid delivery vectors are known in the art.

Compositions of the invention may be immunogenic compositions, and in some embodiments may be vaccine compositions comprising an antigen comprising an epitope recognized by an antibody of the invention or an antigen binding fragment thereof. Vaccines according to the invention may either be prophylactic (i.e., prevent infection) or therapeutic (i.e., treat or ameliorate infection).

Compositions may include an antimicrobial, particularly if packaged in a multiple dose format. They may comprise detergent e.g., a Tween (polysorbate), such as Tween 80. Detergents are generally present at low levels e.g., less than 0.01%. Compositions may also include sodium salts (e.g., sodium chloride) to give tonicity. A concentration of 10±2 mg/ml NaCl is typical.

Further, compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilisation may be adjusted to between 5 and 8, or between 5.5 and 7, or around 6.1 prior to lyophilisation.

The compositions of the invention may also comprise one or more immunoregulatory agents. In one embodiment, one or more of the immunoregulatory agents include(s) an adjuvant.

The epitope compositions of the invention may elicit both a cell mediated immune response as well as a humoral immune response in order to effectively address RSV and MPV infection. This immune response may induce long lasting (e.g., neutralizing) antibodies and a cell mediated immunity that can quickly respond upon exposure to RSV or MPV or both RSV and MPV.

Medical Treatments and Uses

The antibodies and antibody fragments of the invention or derivatives and variants thereof may be used for the treatment of RSV infection, i.e., RSV A infection or RSV B infection or co-infection with both RSV A and RSV B; for the prevention of infection of RSV A or RSV B or both RSV A and RSV B; or for the diagnosis of RSV A or RSV B infection. Preferably, the antibody, or the antigen binding fragment thereof, according to the present invention may be used in the treatment or attenuation of infection by group A RSV or group B RSV.

The antibody, or the antigen binding fragment thereof, the nucleic acid, the vector, the cell, the immunogenic polypeptide, or the pharmaceutical composition according to the present invention may be provided for use as a medicament (i) for the treatment or attenuation of group A RSV or group B RSV infection; (ii) for vaccination against group A RSV or group B RSV infection; or (iii) for diagnosis of group A RSV or group B RSV infection.

Within the scope of the invention are several forms of administration of the antibody, or the antigen binding fragment thereof, the nucleic acid, the vector, the cell, the immunogenic polypeptide, or the pharmaceutical composition; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid.

The antibody, or the antigen binding fragment thereof, the nucleic acid, the vector, the cell, the immunogenic polypeptide, or the pharmaceutical composition of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Delivery of the antibody, or the antigen binding fragment thereof, the nucleic acid, the vector, the cell, the immunogenic polypeptide, or the pharmaceutical composition may generally be accomplished by injection, subcutaneously, intraperitoneally, intravenously or intramuscularly, or delivered to the interstitial space of a tissue. They can also be administered into a lesion. Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms. Preferably, the antibody, or the antigen binding fragment thereof, the nucleic acid, the vector, the cell, the immunogenic polypeptide, or the pharmaceutical composition according to the invention is administered to a subject before an RSV-infection has taken place. Alternatively, the antibody, or the antigen binding fragment thereof, the nucleic acid, the vector, the cell, the immunogenic polypeptide, or the pharmaceutical composition according to the invention is administered when a subject is already infected with RSV.

Methods of diagnosis may include contacting an antibody or an antibody fragment with a sample. Such samples may be tissue samples taken from, for example, nasal passages, sinus cavities, salivary glands, lung, liver, pancreas, kidney, ear, eye, placenta, alimentary tract, heart, ovaries, pituitary, adrenals, thyroid, brain or skin. The methods of diagnosis may also include the detection of an antigen/antibody complex.

The invention therefore provides (i) an antibody, an antibody fragment, or variants and derivatives thereof according to the invention, (ii) an immortalized B cell clone according to the invention, (iii) an epitope capable of binding an antibody of the invention or (iv) a ligand, preferably an antibody, capable of binding an epitope that binds an antibody of the invention for use in therapy.

The invention also provides a method of treating a subject comprising administering to the subject an antibody, an antibody fragment, or variants and derivatives thereof according to the invention, or, a ligand, preferably an antibody, capable of binding an epitope that binds an antibody of the invention. In one embodiment, the method results in reduced RSV (i.e., RSV A or RSV B) infection in the subject. In another embodiment, the method prevents, reduces the risk or delays of RSV (i.e., RSV A or RSV B) infection in the subject.

The invention also provides the use of (i) an antibody, an antibody fragment, or variants and derivatives thereof according to the invention, (ii) an immortalized B cell clone according to the invention, (iii) an epitope capable of binding an antibody of the invention, (iv) a ligand, preferably an antibody, that binds to an epitope capable of binding an antibody of the invention, or (v) a pharmaceutical composition of the invention in (i) the manufacture of a medicament for the treatment or attenuation of infection by RSV A or RSV B or both RSV A and RSV B (ii) a vaccine, or (iii) diagnosis of RSV A or RSV B infection.

The invention provides a composition of the invention for use as a medicament for the prevention or treatment of RSV A or RSV B infection. It also provides the use of an antibody of the invention and/or a protein comprising an epitope to which such an antibody binds in the manufacture of a medicament for treatment of a subject and/or diagnosis in a subject. It also provides a method for treating a subject, comprising the step of administering to the subject a composition of the invention. In some embodiments the subject may be a human. One way of checking efficacy of therapeutic treatment involves monitoring disease symptoms after administration of the composition of the invention. Treatment can be a single dose schedule or a multiple dose schedule.

In one embodiment, an antibody, antibody fragment, immortalized B cell clone, epitope or composition according to the invention is administered to a subject in need of such treatment. Such a subject includes, but is not limited to, one who is particularly at risk of or susceptible to RSV A or RSV B infection, including, for example, an immunocompromised subject. The antibody or antibody fragment of the invention can also be used in passive immunization or active vaccination.

Antibodies and fragments thereof as described in the present invention may also be used in a kit for the diagnosis of RSV A or RSV B infection. Further, epitopes capable of binding an antibody of the invention may be used in a kit for monitoring the efficacy of vaccination procedures by detecting the presence of protective anti-RSV A or anti-RSV B antibodies. Antibodies, antibody fragment, or variants and derivatives thereof, as described in the present invention may also be used in a kit for monitoring vaccine manufacture with the desired immunogenicity.

The invention also provides an epitope that specifically binds to an antibody of the invention or an antigen binding fragment thereof, for use (i) in therapy, (ii) in the manufacture of a medicament for the treatment or attenuation of RSV A or RSV B or both RSV A and RSV B infection, (iii) as a vaccine, or (iv) in screening for ligands able to neutralize RSV A or RSV B or both RSV A and RSV B infection.

The invention also provides a method of preparing a pharmaceutical, comprising the step of admixing a monoclonal antibody with one or more pharmaceutically-acceptable carriers, wherein the monoclonal antibody is a monoclonal antibody that was obtained from a transfected host cell of the invention. Thus the procedures for first obtaining the monoclonal antibody (e.g., expressing it and/or purifying it) and then admixing it with the pharmaceutical carrier(s) can be performed at very different times by different people in different places (e.g., in different countries).

Starting with a transformed B cell or a cultured plasma cell of the invention, various steps of culturing, sub-culturing, cloning, sub-cloning, sequencing, nucleic acid preparation etc. can be performed in order to perpetuate the antibody expressed by the transformed B cell or the cultured plasma cell, with optional optimization at each step. In one embodiment, the above methods further comprise techniques of optimization (e.g., affinity maturation or optimization) applied to the nucleic acids encoding the antibody. The invention encompasses all cells, nucleic acids, vectors, sequences, antibodies etc. used and prepared during such steps.

In all these methods, the nucleic acid used in the expression host may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

General

As used herein, the terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')$_2$, Fv or scFv. Further, the term "antibody" as used herein includes both antibodies and antigen binding fragments thereof.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

The term "comprising" encompasses "including" as well as "consisting" e.g., a composition "comprising" X may consist exclusively of X or may include something additional e.g., X+Y.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1. Isolation and Characterization of Monoclonal Antibodies from Human Memory B Cells Able to Potently Neutralize RSV From a cohort of 125 blood donors we selected 7 donors showing high serum antibody titers against RSV. CD22+ IgG+ B cells were sorted from cryopreserved peripheral blood mononuclear cells (PBMCs) and immortalized at 3 to 5 cells/well using Epstein Barr Virus (EBV) and CpG oligodeoxynucleotide 2006 and irradiated allogeneic PBMCs as feeder cells. Culture supernatants were harvested after 14 days and analyzed for the presence of neutralizing antibodies using a microneutralization assay based on infection of Hep-2 cells by RSV strain A2. Neat supernatants were incubated with 50-100 TCID$_{50}$ of viruses for 1 hour at room temperature prior to addition of Hep-2 target cells, which were incubated for 6 days. Viable cells were then detected with a spectrophotometer by adding to the cultures the WST-1 reagent (Roche) for 3 to 4 hours. From five independent experiments, 28 mAbs that neutralized RSV were isolated (FIG. 1). Four mAbs (HMB2437, HMB2435, HMB2416 and HMB2432) derived from 3 different donors (E, D and B) showed the highest potency against the reference RSV isolate A/A2/61 and these were then selected for further analysis. A fifth mAb, HMB2439, was not selected since in preliminary experiments showed very weak activity against RSV B strains.

The four selected mAbs were all IgG1 and two (HMB2437 and HMB2432) carried a kappa light chain, while the other two (HMB2435 and HMB2416) carried a lambda light chain. The VH and VL genes of HMB2437, HMB2435, HMB2416 and HMB2432 were cloned into IgG1 expression vectors and recombinant mAbs were produced by transient transfection of 293 Freestyle cells (293F). Supernatants from transfected cells were collected after 10 days of culture and IgG were affinity purified by Protein A chromatography. The four mAbs carried all different VH, D and JH, VL and JL gene fragments and were therefore considered not clonally related (Table 4). Based on the amino acid sequences, the isoelectric points (pI) of the four mAbs isolated was calculated and found to be in the range from 8.1 to 8.45 (Table 4). The pI values calculated for palivizumab and D25 were 8.51 and 7.00, respectively.

TABLE 4

V gene usage, isoelectric points (pI) and donor origin of the four selected mAbs.

|  |  |  | VH | D | JH | VL | JL | pI | Donor |
|---|---|---|---|---|---|---|---|---|---|
| HMB2437 | IgG1 | κ | 2-26*01 | 5-24*01 | 6*02 | 1-39*01 | 5*01 | 8.24 | E |
| HMB2435 | IgG1 | λ | 3-30*01 | 3-10*01 | 6*02 | 2-14*01 | 3*02 | 8.36 | D |
| HMB2416 | IgG1 | λ | 4-30*01 | 5-5*01 | 4*02 | 3-21*01 | 2*01 | 8.10 | B |
| HMB2432 | IgG1 | κ | 5-51*01 | 2-15*01 | 6*02 | 1-39*01 | 1*01 | 8.45 | B |

Figure 2:
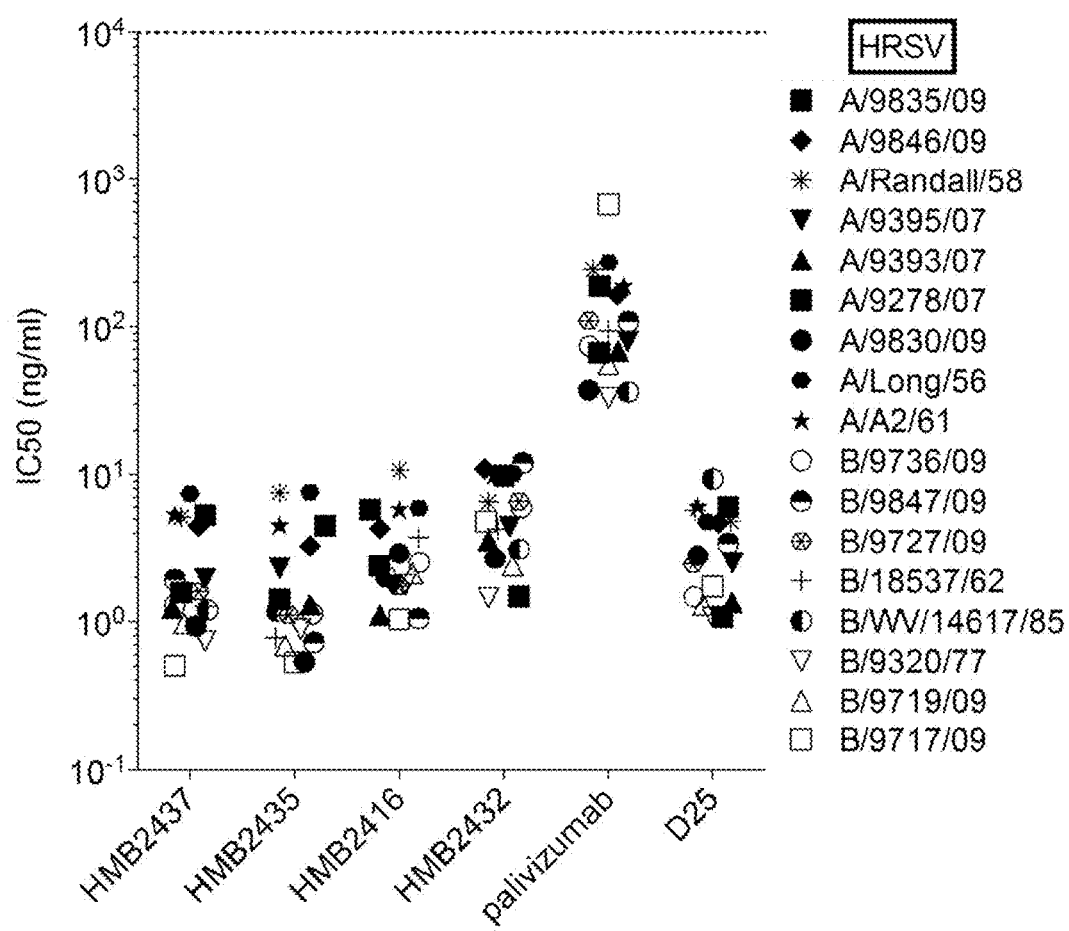
FIG. 2 shows the results of neutralization of RSV A and B strains by monoclonal antibodies HMB2437, HMB2435, HMB2416, HMB2432, palivizumab and D25.

The four mAbs were then tested for their breadth and potency against a panel of RSV A and B isolates (Table 5 and FIG. 2) in parallel with palivizumab and D25 mAbs. The following RSV strains were tested: RSV A2 (A, 1961 Australia; A/A2/61), RSV Long (A, Maryland US, 1956; A/Long/56), RSV Randall (A, Chicago US, 1958; A/Randall/58), RSV 9395/2007 (A, Pavia IT, 2007; A/9395/07), RSV 9393/2007 (A, Pavia IT, 2007; A/9393/07), RSV 9278/2007 (A, Pavia IT, 2007; A/9278/07), RSV 9830/2009 (A, Pavia IT, 2009; A/9830/09), RSV 9835/2009 (A, Pavia IT, 2009; A/9835/09), RSV 9846/2009 (A, Pavia IT, 2009; A/9846/09), RSV 9320 (B, Massachusetts US, 1977; B/9320/77), WV/14617/85 (B, Huntington W. Va., 1985; B/WV/14617/85), 18537 (B, Washington District of Columbia US, 1962; B/18537/62), RSV 9727/2009 (B, Pavia IT, 2009; B/9727/09), RSV 9736/2009 (B, Pavia IT, 2009; B/9736/09), RSV 9847/2009 (B, Pavia IT, 2009; B/9847/09), RSV 9719/2009 (B, Pavia IT, 2009; B/9719/09), RSV 9717/2009 (B, Pavia IT, 2009; B/9717/09).

TABLE 5

Virus neutralizing titers of human and reference monoclonal antibodies.

| | IC50 (ng/ml) | | | | | |
|---|---|---|---|---|---|---|
| RSV Viruses | HMB2437 | HMB2435 | HMB2416 | HMB2432 | palivizumab | D25 |
| A/9830/09 | 0.9 | 0.5 | 2.9 | 2.7 | 37.3 | 2.8 |
| A/9278/07 | 1.6 | 1.4 | 2.4 | 1.5 | 66.6 | 1.1 |
| A/9393/07 | 1.2 | 1.3 | 1.1 | 3.6 | 68.5 | 1.3 |
| A/9395/07 | 2.0 | 2.3 | 1.8 | 4.5 | 79.6 | 2.5 |
| A/A2/61 | 5.3 | 4.5 | 5.8 | 9.8 | 188.1 | 6.0 |
| A/Long/56 | 7.4 | 7.6 | 5.9 | 10.1 | 273.9 | 4.8 |
| A/Randall/58 | 5.2 | 7.5 | 10.7 | 6.5 | 242.9 | 4.9 |
| A/9846/09 | 4.5 | 3.3 | 4.3 | 11.0 | 164.7 | 4.7 |
| A/9835/09 | 5.3 | 4.5 | 5.8 | 9.8 | 188.1 | 6.0 |
| B/9717/09 | 0.5 | 0.5 | 1.0 | 4.8 | 678.0 | 1.7 |
| B/9719/09 | 1.0 | 0.7 | 2.1 | 2.4 | 55.6 | 1.3 |
| B/9320/77 | 0.7 | 0.9 | 1.8 | 1.5 | 33.0 | 1.1 |
| B/WV/14617/85 | 1.2 | 1.2 | 2.0 | 3.1 | 36.1 | 9.4 |
| B/18537/62 | 1.3 | 0.8 | 3.7 | 4.3 | 93.9 | 5.7 |
| B/9727/09 | 1.6 | 1.1 | 1.7 | 6.6 | 110.0 | 2.5 |
| B/9847/09 | 1.9 | 0.7 | 1.1 | 12.0 | 108.1 | 3.4 |
| B/9736/09 | 1.3 | 1.1 | 2.5 | 6.0 | 74.2 | 1.5 |

Figure 3:
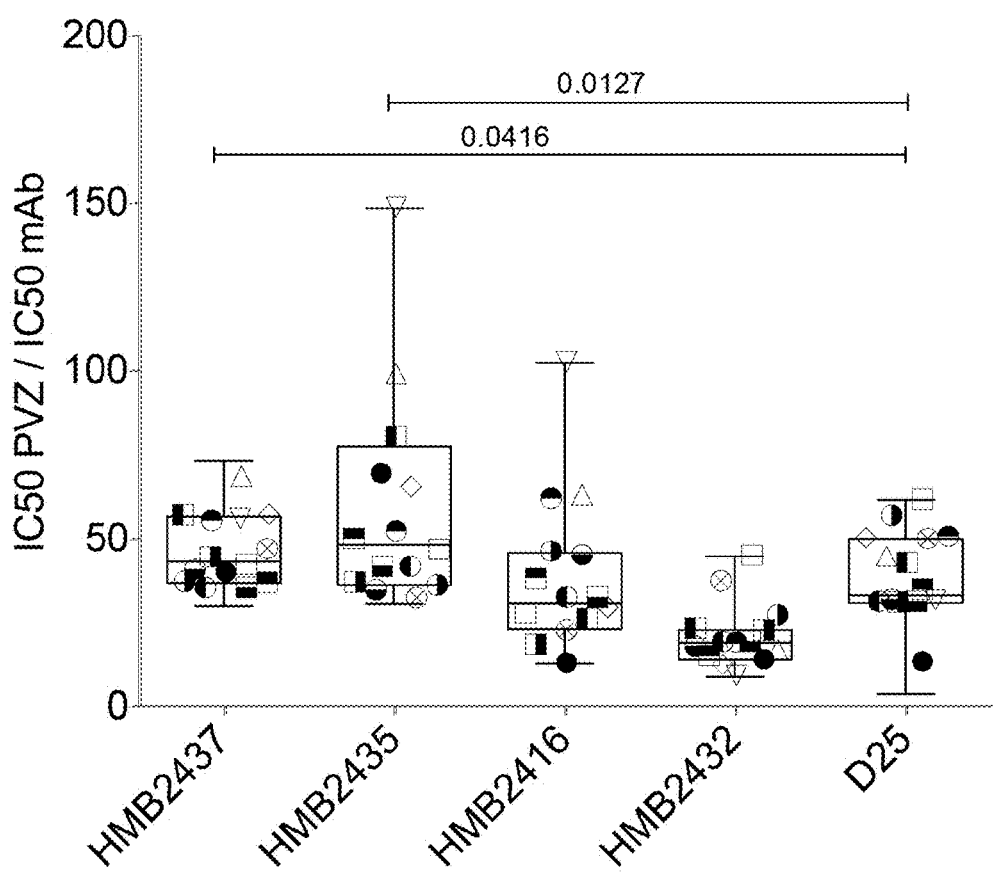
FIG. 3 shows a comparison of the neutralization potency of monoclonal antibodies HMB2437, HMB2435, HMB2416, HMB2432 and D25 with palivizumab (ratio of the palivizumab IC50 with the IC50s of the other monoclonal antibodies).

When compared to palivizumab the four mAbs showed a neutralizing potency against the full set of RSV A and B strains that was 9 to 148 fold higher than palivizumab and in this type of analysis HMB2435 and HMB2437 scored significantly better than D25 (FIG. 3).

Figure 4A:
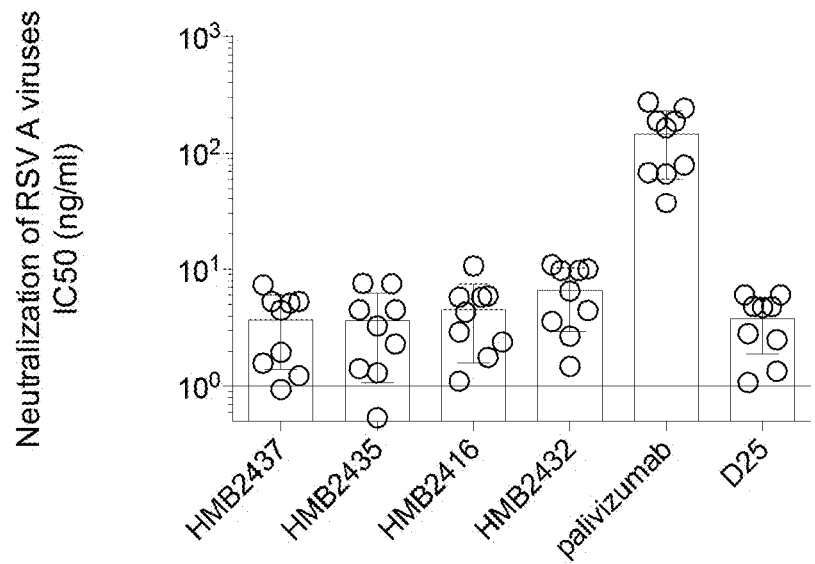
FIG. 4 shows a comparison of the neutralization potency of monoclonal antibodies HMB2437, HMB2435, HMB2416, HMB2432, D25 and palivizumab against RSV A (upper panel) and B (lower panel) viruses.
Figure 4B:
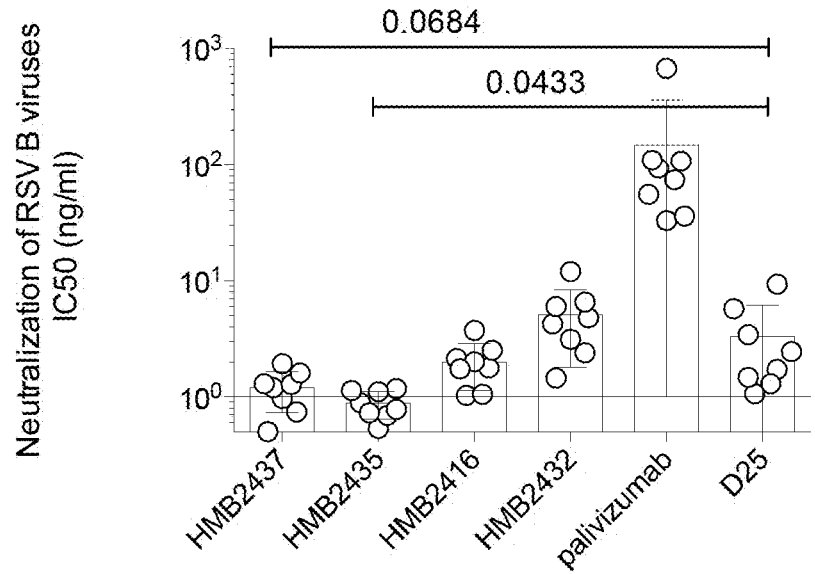

When compared with D25 the four antibodies showed a similar activity against RSV A strains, while HMB2435 showed a significantly (p=0.0433) higher potency against RSV B strains. A similar, but statistically not significant, trend was observed for mAb HMB2437. The other two mAbs HMB2416 and HMB2432 showed a neutralizing potency similar to D25 against both RSV A and B strains (FIG. 4).

Example 2. Epitope Mapping Studies

Figure 5:
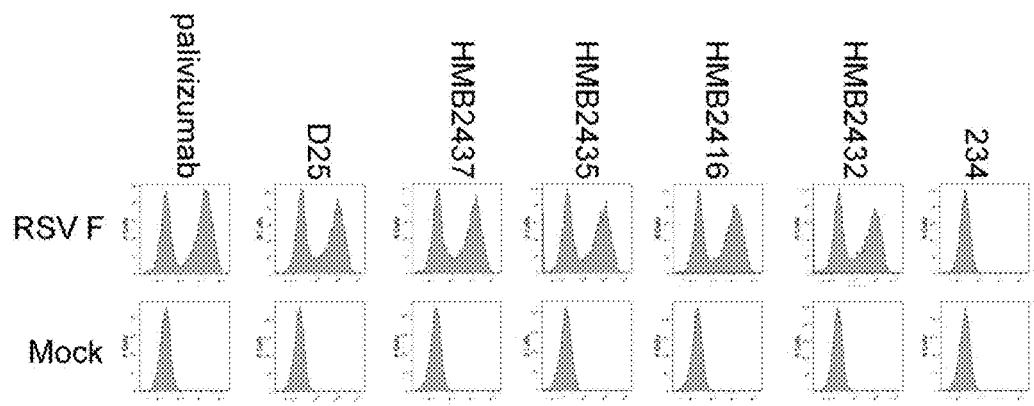
FIG. 5 shows the binding of monoclonal antibodies HMB2437, HMB2435, HMB2416, HMB2432, D25, palivizumab and 234 to cells transfected with a plasmid encoding the RSV F gene or an empty plasmid as a control.

In order to identify the target antigen recognized by HMB2435, HMB2437, HMB2416 and HMB2432 on RSV viruses, we analyzed the four mAbs in parallel with palivizumab and the control mAb 234 (specific for human MPV), for their ability to stain intracellularly 293F cells transiently transfected with mammalian expression vectors encoding for the full length F protein from either RSV (A2 strain) indicating that the four mAbs recognize epitopes present on RSV F proteins. The four mAbs HMB2435, HMB2437, HMB2416 and HMB2432 stained the cells transfected with the RSV F protein but not the cells transfected with an empty control vector (mock) (FIG. 5). These results indicate that the four mAbs target epitopes that are located on RSV F protein.

A DNA construct encoding RSV F residues 26-136 and 147-512 (corresponding to the F ecto-domain without the fusion peptide of the RSV strain A2) with a C-terminal histidine tag was codon optimized and synthesized. Recombinant F was expressed using a baculovirus expression vector in Sf21 cells and purified from the supernatant by nickel affinity and size exclusion chromatography (SEC). A similar construct was already used by others (Swanson et al. PNAS 2011 and McLellan et al. J Virol 2011) to solve the crystal structure of the post-fusion F protein.

The protein was analyzed under non-reducing conditions on an SDS-PAGE gel and gave a band at ≈65-70 kDa and when analyzed by SEC on a S200 column the "post-fusion" RSV F protein eluted as a symmetric peak with an apparent molecular weight of ≈150 kDa that corresponds to the MW of the trimeric F protein. This protein was used to test the four antibodies by ELISA. The three antibodies HMB2437, HMB2435 and HMB2416 did not react with the "post-fusion" protein, while HMB2432 reacted poorly. In parallel, palivizumab, D25 and 234 were also tested under the same conditions. As expected palivizumab reacted strongly with the post-fusion F protein while D25 did not.

These data indicate that the four antibodies recognize epitopes on the RSV F protein, which are either not accessible or poorly accessible on the post-fusion F protein. To test these mAbs against the pre-fusion F protein we engineered a stabilized soluble form of the F protein by: i) introducing of inter-monomeric disulphide bridges (cf. Magro, M. et al. (2012) Proc. Natl Acad. Sci. USA 109, 3089-3094), ii) deleting of the fusion peptide region, and iii) substituting of the trans-membrane region with a T4 fibritin motif (foldon) to stabilize the trimeric structure. When tested by surface plasmon resonance (SPR), palivizumab bound to both pre- and post-fusion proteins with similar affinities.

In striking contrast, HMB2435, HMB2437, HMB2416 and HMB2432 selectively bound to the pre-fusion F protein (Table 6). Using cross-competition SPR experiments and a panel of available antibodies of known specificity (palivizumab, D25 and 101F) we identified on the pre-fusion F protein four antigenic sites (S1, S2, S3 and S5) (FIG. 6). In particular, none of the four mAbs competed with palivizumab. HMB2432 competed with 101F (which recognize the antigenic site IV on the post-fusion), thus both 101F and HMB2432 were assigned to the site S2 on the pre-fusion F protein. HMB2416 competed with D25 and the two mAbs were assigned to site S3. HMB2437 competed with both 101F and D25 and was therefore assigned to a site in between S2 and S3. Finally, mAb HMB2435 did not compete with any of the mAbs tested indicating that it binds to a novel site, S5, on the pre-fusion F protein.

TABLE 6

Binding to pre- and post-fusion F proteins by ELISA and SPR

| RSV Viruses | Post-fusion F protein binding (ELISA) | Post-fusion F protein binding (SPR) | Pre-fusion F protein binding (SPR) |
|---|---|---|---|
| HMB2435 | − | − | + |
| HMB2437 | − | − | + |
| HMB2416 | − | − | + |
| HMB2432 | +/− | − | + |
| palivizumab | + | + | + |
| D25 | − | − | + |
| 234 | − | ND | ND |

SPR experiments were performed on a ProteOn-XPR36 instrument (Bio-Rad). Antibodies were immobilized on a ProteOn GLC sensor chip surface through amine coupling at 2,000 response units (RU) and a blank surface with no antibody was created under identical coupling conditions for use as a reference. RSV F protein was injected at a flow rate of 100 ml min$^{-1}$, at concentrations of 200, 100, 75, 50 and 25 nM in different sensor channels. The data were processed using Proteon software and double referenced by subtraction of the blank surface and buffer-only injection before local fitting of the data. Binding curves were locally fitted to the two states model, to perform a $K_d$ calculation. For competition experiment, antibodies were covalently coupled to a GLC sensor chip at 2,000 RU. RSV F protein was injected at 200 nM and the competing antibody was injected after 20 s of dissociation time.

Example 3. Removal of Unnecessary Somatic Mutations

Figure 12:
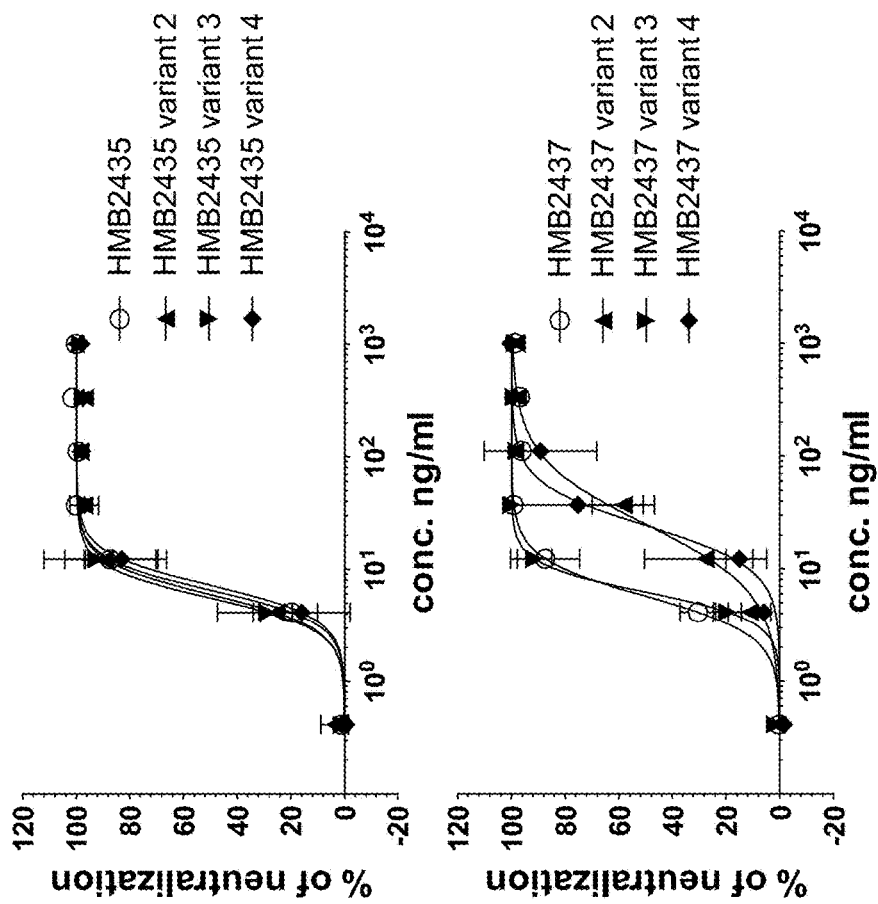
FIG. 12 shows the results of neutralization of RSV A2 strain by monoclonal antibodies HMB2435 and HMB2437 and the corresponding variants 2, 3 and 4.
Figure 13:
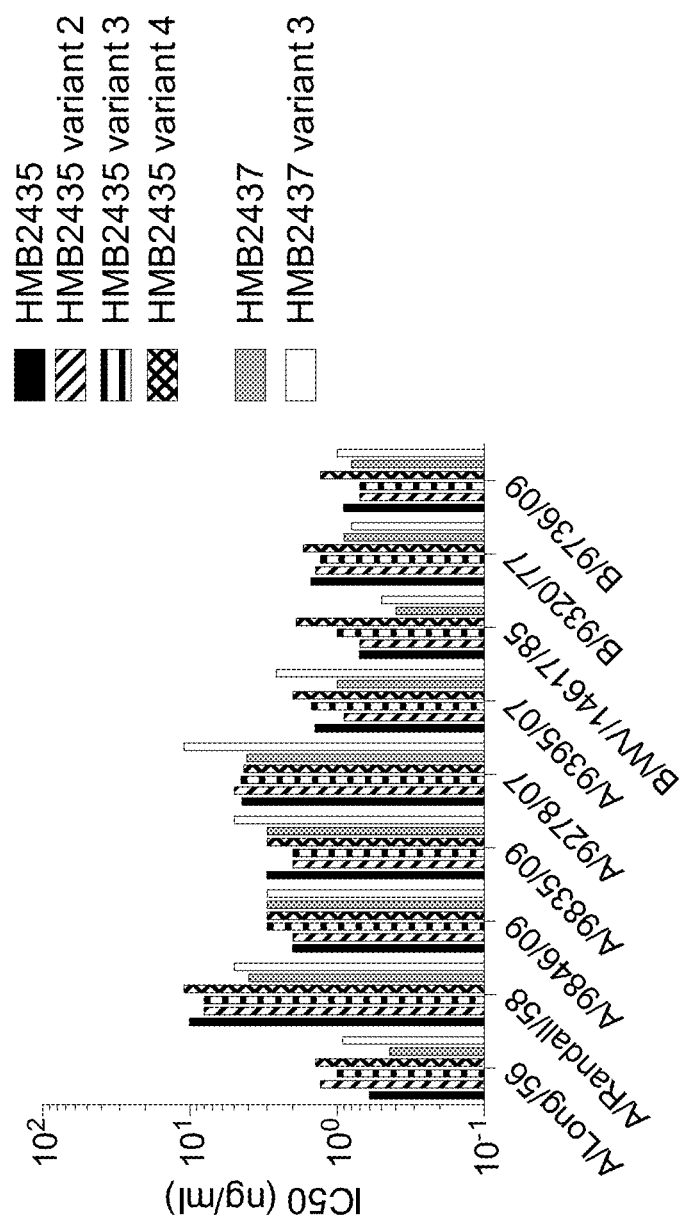
FIG. 13 shows a comparison of the neutralization potency of monoclonal antibodies HMB2435, HMB2435 variant 2, HMB2435 variant 3, HMB2435 variant 4, HMB2437 and HMB2437 variant 3 on a panel of 9 RSV A and RSV B strains.

In the development of therapeutic monoclonal antibodies the risk of antibody immunogenicity is also related to the degree of similarity of the antibody sequence with that of the unmutated ancestor antibody. In this respect, the removal of all the unnecessary somatic mutations is associated with a lower risk of antibody immunogenicity. We therefore removed all the somatic mutations from the framework heavy and light chain regions of antibodies HMB2435 and HMB2437, by synthetizing new antibody sequences in which we reverted back to the <<germline>> configuration (according to the IMGT VDJ and VJ assignments and rearrangement interpretation) all the somatic mutations located in the framework regions 1, 2, 3 and 4 of both variable heavy and light chains. Three additional antibody variants (variants 2, 3 and 4) of HMB2435 and HMB2437 antibodies were then produced using different heavy and light chain combinations. In particular: HMB2435 and HMB2437 variants 2 are formed by the original heavy chain sequences (SED ID NOs: 13 and 29, respectively) combined with the framework regions germlined light chains (SEQ ID NOs: 76 and 86, respectively); HMB2435 and HMB2437 variants 3 are formed by the framework regions germlined heavy chains sequences (SEQ ID NOs: 75 and 85, respectively) combined with the original light chain sequences (SEQ ID NOs: 14 and 30, respectively); HMB2435 and HMB2437 variants 4 are formed by the combination of framework regions germlined heavy and light chains (SEQ ID NOs: 75 and 76 for HMB2435 and SEQ ID NOs: 85 and 86 for HMB2437). An alignment of HMB2435 and HMB2437 heavy and light chains amino acid sequences in the original and framework regions germlined variants is provided in FIG. 11. The FIG. 11 shows that HMB2435 has 20 somatic mutations located in the framework regions (15 in the heavy chain and 5 in the light chain) and HMB2437 has 13 somatic mutations located in the framework regions (5 in the heavy chain and 10 in the light chain). When HMB2435 and HMB2437 and the corresponding variants 2, 3 and 4 were tested against RSV A2 strain in a neutralization assay (FIG. 12), HMB2435 and all the framework germlined variants neutralized with the same potency RSV A2 neutralization, thus indicating that the 20 amino acid somatic mutations in the framework regions of the heavy and light chain of HMB2435 are dispensable for its neutralizing activity and that therefore the HMB2435 variant 4 represents a fully framework regions germlined antibody with favorable characteristics for further development over the original HMB2435 antibody. In the case of HMB2437, however, not all the framework regions germlined variants neutralized RSV A2 virus with the same potency of the original HMB2437. In particular, HMB2437 variants 2 and 4 showed a 10-fold lower neutralization activity as compared to HMB2437 and HMB2437 variant 3. These results indicate that the 10 somatic mutations located in the framework regions of the HMB2437 light chain are not dispensable for its neutralizing activity. In summary, in the case of HMB2437 the same neutralizing activity is mantained only in the HMB2437 variant 3 in which the 5 somatic mutations in the heavy chain framework regions are reversed to the germline VH-encoded amino acids. We finally tested HMB2435 and HMB2437 and all the framework germlined variants that showed similar neutralizing activity as compared to the original antibody (i.e. HMB2435 variants 2, 3 and 4 and HMB2437 variant 3) against a panel of 9 RSV A and B viruses spanning 53 years of virus antigenic evolution. The results of the analysis of this extended panel of viruses (FIG. 13) confirmed that the reversion of the somatic mutations of the framework regions to the germline residues in the HMB2435 antibody variants 2, 3 and 4 and in HMB2437 antibody variant 3 did not reduce their neutralizing activity as compared to the originals HMB2435 and HMB2437 antibodies.

Table of Sequences and SEQ ID Numbers

| SEQ ID NO | Description | Sequence |
|---|---|---|
| | | HMB2435 ANTIBODY |
| 1 | CDRH1 aa | GFAFNNFA |
| 2 | CDRH2 aa | VSYDGTSP |
| 3 | CDRH3 aa | ARGLGSGSYSWIGYFYAMDV |
| 4 | CDRL1 aa | SSDVGGYVY |
| 5 | CDRL2 aa | DVS |
| 6 | CDRL3 aa | ISYTDRNTVV |
| 7 | CDRH1 nuc | ggattcgccttcaataattttgct |
| 8 | CDRH2 nuc | gtgtcctatgacggaaccagtcca |
| 9 | CDRH3 nuc | gcgagagggcttggttcggggagttattcgtggattggttacttttatgcaatggacgtc |
| 10 | CDRL1 nuc | agcagtgacgttggtggtggtatgtctat |
| 11 | CDRL2 nuc | gatgtcagt |
| 12 | CDRL3 nuc | atctcgtataccgacagaaacactgtcgtt |
| 13 | heavy chain aa | QVQLVESGGGVVQPGRPLRLSCAASGFAFNNFALHWVRQAPG KGPEWLAAVSYDGTSPYYAESVRARFSISRDNSKKTFYLQLDSLRP EDTAVYYCARGLGSGSYSWIGYFYAMDVWGRGTTVTVSS |
| 14 | light chain aa | QSALTQPASVSGSPGQSITISCTGTSSDVGGYVYVAWYQQHPGT aaAPKLIIYDVSDRPSGVSNRFSGSKSGNTASLTISGLQAEDDADYYC ISYTDRNTVVFGGGTKLTVL |
| 15 | heavy chain nuc | caggtgcagctggtggagtctggggggaggcgtggtccagcctggaggcccctcagactct cctgtgcagcctctggattcgccttcaataattttgcttttacactgggtccgccaggctccagg caagggtccagagtggctggcagctgtgtcctatgacggaaccagtccatactacgcagag tccgtcagggcccgattcagcatctccagagacaattccaagaaaacattctatctgcaatt ggacagcctgcgacctgaagacacggctgtctattactgtgcgagagggcttggttcgggga gttattcgtggattggttacttttatgcaatggacgtctgggccgagggacgacggtcaccgt ctcctca |
| 16 | light chain nuc | cagtctgccctgactcagcctgcctccgtgtctgggtctcctggacaatcgatcaccatctcc tgcactggaaccagcagtgacgttggtggttatgtctatgtcgcctggtaccaacaacaccc aggcacagcccccaaactcatcatttatgatgtcagtgatcggcctcaggggtttctaatcg attctctgggtccaagtctggcaacacggcctcctgaccatctctgggctccaggctgagg acgacgctgattattactgcatctcgtataccgacagaaacactgtcgtttttggcggcggga ccaagttgaccgtcctg |
| | | HMB2437 ANTIBODY |
| 17 | CDRH1 aa | GFSLTDARMG |
| 18 | CDRH2 aa | IFSNDEK |
| 19 | CDRH3 aa | ARVDQGWVNTYSAFYYGM DF |
| 20 | CDRL1aa | QYISTH |
| 21 | CDRL2 aa | GAS |
| 22 | CDRL3 aa | QQTYKTPIT |
| 23 | CDRH1 nuc | ggattctcactcacagatgctagaatgggt |
| 24 | CDRH2 nuc | attttctcgaatgacgaaaaa |
| 25 | CDRH3 nuc | gcacgagtcgatcaggatggtaaacacgtacagcgccttttattatggtatggacttc |
| 26 | CDRL1 nuc | cagtacattagcacccat |
| 27 | CDRL2 nuc | ggtgcctcc |
| 28 | CDRL3 nuc | caacagacttataaaaccccgatcacc |
| 29 | heavy chain aa | QVTLKESGPVLVKPSETLTLTCTVSGFSLTDARMGVSWIRQPPGK ALEWLAHIFSNDEKFYSTSLKTRLTISKDTSTSQVVLRMTNMDPVD TATYYCARVDQGWVNTYSAFYYGMDFWGQGTTVTVSS |
| 30 | light chain aa | DIQMTQSPSSLSASVGERVTITCRASQYISTHLNWYQHKPGKAPR aaLLIYGASHLEGGDPSRFSGSGSGTDFSLTITSLQPEDFATYYCQQT YKTPITFAQGTRLEIK |
| 31 | heavy chain nuc | caggtcaccttgaaggagtctggtcctgtgctggtgaaaccctcagagaccctcacgctgac ctgcaccgtctctggattctcactcacagatgctagaatgggtgtgagttggatccgtcagcc cccagggaaggccctggagtggcttgcacacattttctcgaatgacgaaaaattctacagca catctctgaagaccaggctcaccatctccaaggacacctccacaagccaggtggtccttag gatgaccaacatggaccctgtggacacagccacttattattgtgcacgagtcgatcagggat gggtaaacacgtacagcgccttttattatggtatggacttctggggccaagggaccacggtc accgtctcctca |
| 32 | light chain nuc | gacatccagatgacccagtctccatcctccctgtctgcatctgtaggagaaagagtcaccat cacttgccgggcaagtcagtacattagcacccatttaaattggtatcagcacaaaccaggga aagcccctcgtctcctgatctatggtgcctcccatttggaaggtggggacccatcacggttca gtggcagtggatctgggacagatttcagtctcaccattaccagtctgcaacctgaagattttgc aacttactactgtcaacagacttataaaaccccgatcaccttcgcccaagggacacgactg gagattaaa |
| | | HMB2416 ANTIBODY |
| 33 | CDRH1 aa | GGSISSGDYY |
| 34 | CDRH2 aa | IYFSGST |
| 35 | CDRH3 aa | AREDTTMAIPYYFDP |
| 36 | CDRL1 aa | NIGNEN |
| 37 | CDRL2 aa | SDS |

Table of Sequences and SEQ ID Numbers

| SEQ ID NO | Description | Sequence |
|---|---|---|
| 38 | CDRL3 aa | QVWDSSTDQVV |
| 39 | CDRH1 nuc | ggtggctccatcagcagtggtgattactac |
| 40 | CDRH2 nuc | atctacttcagtggcagcacc |
| 41 | CDRH3 nuc | gccagagaggatacaactatggctattccatactacttcgacccc |
| 42 | CDRL1 nuc | aatattggaaatgaaaat |
| 43 | CDRL2 nuc | tctgatagc |
| 44 | CDRL3 nuc | caggtgtgggatagtagtactgatcaagtggta |
| 45 | heavy chain aa | QVQLQESGPGLVKPSQTLSLTCTVSGGSISSGDYYWSWIRQPPG KGLEWIGYIYFSGSTYYNPSLKSRVTMSGDTSKNQFSLRLSSVTAA DTAVYYCAREDTTMAIPYYFDPWGRGILVTVSS |
| 46 | light chain aa | SYVLTQPPSVSVAPGRTARITCGRHNIGNENVHWYQQRPGQAP VLVIYSDSDRPSGIPERFSGSNSGNTATLSISRVEAGDEADYYCQV WDSSTDQVVFGGGTKLTVL |
| 47 | heavy chain nuc | caggtgcagctgcaggagtcgggcccaggactcgtgaagccttcacagaccctgtccctc acctgcactgtctctggtggctccatcagcagtggtgattactactggagttggatccgccag ccccccagggaaggggcctggagtggattgggtacatctacttcagtggcagcacctactaca atccgtccctcaagagtcgagttaccatgtcaggggacacgtccaagaatcagttctccctg aggctgagctctgtgactgccgcagacacggccgtgtattattgtgccagagaggatacaac tatggctattccatactacttcgacccctggggccggggaatcctggtcaccgtctcctca |
| 48 | light chain nuc | tcctatgtcctgactcagccaccctcagtgtcagtggccccccggaagg acggccaggatca cctgtgggagacataatattggaaatgaaaatgttcactggtaccagcagaggccaggcca ggcccctgtgctggtcatctattctgatagcgaccggccctcagggatccctgagcgattctc tggctccaactctgggaacacggccacc ctaagcatcagcagggtcgaagccggggatg aggccgactattattgtcaggtgtgggatagtagtactgatcaagtggtattcggcggaggga ccaagctgaccgtccta |

HMB2432 ANTIBODY

| SEQ ID NO | Description | Sequence |
|---|---|---|
| 49 | CDRH1 aa | GFSFSNYW |
| 50 | CDRH2 aa | VYPADSDT |
| 51 | CDRH3 aa | VRQIGGVVTTATDDYFYGMDI |
| 52 | CDRL1 aa | QTVKSF |
| 53 | CDRL2 aa | DAS |
| 54 | CDRL3 aa | QQSYRTPLT |
| 55 | CDRH1 nuc | ggatttagttttagcaactattgg |
| 56 | CDRH2 nuc | gtctatccggctgactctgacacc |
| 57 | CDRH3 nuc | gtgagacaaatcggggggtggtgacaactgctactgacgactacttctacggtatggacatc |
| 58 | CDRL1 nuc | cagaccgttaaaagcttt |
| 59 | CDRL2 nuc | gatgcatcc |
| 60 | CDRL3 nuc | caacagagttacaggacccctctgacg |
| 61 | heavy chain 1 aa | EVQLVQSGAEVKKPGTSLKISCKGSGFSFSNYWIGWVRQMPGKG LEWMGIVYPADSDTRYSPSFQGQVTISGDNSINTAYLQWSRLKA SDTATYYCVRQIGGVVTTATDDYFYGMDIWGPGTTVIVSS |
| 62 | light chain 1 aa | ETTLTQSPSSLSASVGDRVTITCRASQTVKSFLNWYQQKPGKAPK LLIYDASDLQSGVPSRFSGSGSGTDFTLTISRLQPEDFATYFCQQS YRTPLTFGQGTRVEIK |
| 63 | heavy chain 1 nuc | gaggtgcagctggtgcagtctggagcggaggtgaaaaaacccgggacgtctctgaagatct cctgcaagggttctggatttagttttagcaactattggatcggctgggtgcgccagatgcccgg gaaaggcctggagtggatggggatcgtctatccggctgactctgacaccagatacagcccg tccttccagggccaggtcaccatctcaggcgacaactccatcaataccgcctacctgcagt ggagccgcctgaaggcctcggacaccgccacctattactgtgtgagacaaatcgggggg tggtgacaactgctactgacgactacttctacggtatggacatctgggggcccagggaccacg gtcatcgtctcctca |
| 64 | light chain 1 nuc | gaaacgacactcacgcagtctccatcctccctgtctgcatctgtaggagacagagtcaccat cacttgccgggcaagtcagaccgttaaaagcttttaaattggtatcagcagaagccaggga aagcccctaaactcctgatctatgatgcatccgatttgcaaagtggggtcccatccaggttca gtggcagtggatctgggacagatttcactctcaccatcagccgtctgcaacctgaagattttg caacttacttctgtcaacagagttacaggaccccctctgacgttcggccaagggaccagggtg gaaatcaaa |
| 65 | heavy chain 2 aa | EVQLVQSGAEVKKPGTSLKISCKGSGFSFSNYWIGWVRQMPGKG LEWMGIVYPADSDTRYSPSFQGQVTISGDNSINTAYLQWSRLKA SDTATYYCVRQIGGVVTTATDDYFYGMDIWGPGTTVTVSS |
| 66 | light chain 2 aa | ETTLTQSPSSLSASVGDRVTITCRASQTVKSFLNWYQQKPGKAPK LLIYDASDLQSGVPSRFSGSGSGTDFTLTISRLQPEDFATYFCQQS YRTPLTFGQGTKVEIK |
| 67 | heavy chain 2 nuc | gaggtgcagctggtgcagtctggagcggaggtgaaaaaacccgggacgtctctgaagatct cctgcaagggttctggatttagttttagcaactattggatcggctgggtgcgccagatgcccgg gaaaggcctggagtggatggggatcgtctatccggctgactctgacaccagatacagcccg tccttccagggccaggtcaccatctcaggcgacaactccatcaataccgcctacctgcagt ggagccgcctgaaggcctcggacaccgccacctattactgtgtgagacaaatcgggggg tggtgacaactgctactgacgactacttctacggtatggacatctgggggcccagggaccacg gtcaccgtctcctca |

Table of Sequences and SEQ ID Numbers

| SEQ ID NO | Description | Sequence |
|---|---|---|
| 68 | light chain 2 nuc | gaaacgacactcacgcagtctccatcctccctgtctgcatctgtaggagacagagtcaccat cacttgccgggcaagtcagaccgttaaaagcttttaaattggtatcagcagaagccaggga aagcccctaaactcctgatctatgatgcatccgatttgcaaagtggggtcccatccaggttca gtggcagtggatctgggacagatttcactctcaccatcagccgtctgcaacctgaagattttg caacttacttctgtcaacagagttacaggacccctctgacgttcggccaagggaccaaggtg gaaatcaaa |

HMB2435 ANTIBODY FRAMEWORK REGIONS GERMLINED (FR-GL) VARIANTS

| SEQ ID NO | Description | Sequence |
|---|---|---|
| 69 | CDRH1 nuc | ggcttcgcttttaacaatttcgca |
| 70 | CDRH2 nuc | gtcagttacgacgggacttcacct |
| 71 | CDRH3 nuc | gccagaggactgggcagcgggtcctattcttggatcggctacttctatgctatggatgtg |
| 72 | CDRL1 nuc | agctccgacgtcggaggatacgtgtat |
| 73 | CDRL2 nuc | gatgtgagc |
| 74 | CDRL3 nuc | attagctacaccgacaggaatacagtggtc |
| 75 | heavy chain FR-GL aa | QVQLVESGGGVVQPGRSLRLSCAASGFAFNNFAMHWVRQAPG KGLEWVAVVSYDGTSPYYADSVKGRFTISRDNSKNTLYLQMNSL RAEDTAVYYCARGLGSGSYSWIGYFYAMDVWGQGTTVTVSS |
| 76 | light chain FR-GL aa | QSALTQPASVSGSPGQSITISCTGTSSDVGGYVYVSWYQQHPGK APKLMIYDVSNRPSGVSNRFSGSKSGNTASLTISGLQAEDEADYY CISYTDRNTVVFGGGTKLTVL |
| 77 | heavy chain FR-GL nuc | caggtgcagctggtcgagtctggaggaggagtggtccagccaggacggagtctgagactgt catgcgccgctagcggcttcgcttttaacaatttcgcaatgcactgggtgcggcaggcacca ggcaagggactggaatgggtcgctgtggtcagttacgacgggacttcacctactatgccga tagcgtgaagggcaggtttaccatctcccgcgacaactctaaaaatacactgtacctgcaga tgaactccctgcgagcagaggataccgccgtgtactattgtgccagaggactgggcagcgg gtcctattcttggatcggctacttctatgctatggatgtgtgggggcagggcactaccgtcactg tgtcttca |
| 78 | light chain FR-GL nuc | cagtccgcactgactcagccagcctctgtgagtggatcacccggccagagcatcacaattt cctgcaccggcacaagctccgacgtcggaggatacgtgtatgtctcttggtaccagcagca ccccggcaaggctcctaaactgatgatctatgatgtgagcaaccggcccagtggggtctca aatagattcagcggggtccaagtctggaaacacagcctctctgactatcagtggcctgcaggc cgaggacgaagctgattactattgtattagctacaccgacaggaatacagtggtctttggagg cgggactaaactgaccgtgctg |

HMB2437 ANTIBODY FRAMEWORK REGIONS GERMLINED (FR-GL) VARIANTS

| SEQ ID NO | Description | Sequence |
|---|---|---|
| 79 | CDRH1 nuc | ggcttctccctgaccgacgctcggatgggg |
| 80 | CDRH2 nuc | atttttagcaacgacgaaaag |
| 81 | CDRH3 nuc | gcccggggtggatcaggggtgggtcaataccctattcagccttctattatggaatggacttc |
| 82 | CDRL1 nuc | cagtacatttctacacac |
| 83 | CDRL2 nuc | ggagcttct |
| 84 | CDRL3 nuc | cagcagacatataaaactcccatcacc |
| 85 | heavy chain FR-GL aa | QVTLKESGPVLVKPTETLTLTCTVSGFSLTDARMGVSWIRQPPGK ALEWLAHIFSNDEKSYSTSLKSRLTISKDTSKSQVVLTMTNMDPVD TATYYCARVDQGWVNTYSAFYYGMDFWGQGTTVTVSS |
| 86 | light chain FR-GL aa | DIQMTQSPSSLSASVGDRVTITCRASQYISTHLNWYQQKPGKAP KLLIYGASSLQSGVPSRFSGSGSGTDFTLTISSLQPEDFATYYCQQT YKTPITFGQGTRLEIK |
| 87 | heavy chain FR-GL nuc | caagtgactctgaaggagtctggcccagtgctggtcaaacccaccgaaacactgactctga cctgcacagtgagcggcttctccctgaccgacgctcggatgggggtctcctggatcagaca cccacctggaaaggcactggagtggctggctcacatattagcaacgacgaaaagagctac tccacatctctgaaatctaggctgaccatcagtaaggatacaagtaaatcacaggtggtcct gactatgaccaacatggaccccgtggatacagcaacttactattgtgcccggggtggatcagg ggtgggtcaataccctattcagccttctattatggaatggacttctggggacaggggactaccgt caccgtctcttca |
| 88 | light chain FR-GL nuc | gacatccagatgacccagagccctagctcccctgtccgcatctgtgggggatcgggtcacca tcacatgcagagcctcccagtacatttctacacacctgaactggtatcagcagaagcccgg caaagcccctaagctgctgatctacggagccttctagtctgcagagtgccgtcgtgccctctaggtt cagtggctcagggagcggaacagactttactctgaccatttcaagcctgcagccagaggatt tcgctacttactattgtcagcagacatataaaactcccatcacctttggccaggggaccgg ctggaaatcaaa |

The invention claimed is:

1. An isolated nucleic acid molecule, comprising a polynucleotide that encodes an antibody or an antigen-binding fragment thereof, wherein the encoded antibody or antigen-binding fragment thereof comprises a heavy chain variable region (VH) comprising CDRH1, CDRH2, and CDRH3, and a light chain variable region (VL) comprising CDRL1, CDRL2, and CDRL3, wherein:

(i) a polynucleotide that encodes CDRH1 comprises the nucleic acid sequence of SEQ ID NO:7, a polynucleotide that encodes CDRH2 comprises the nucleic acid sequence of SEQ ID NO:8, a polynucleotide that encodes CDRH3 comprises the nucleic acid sequence of SEQ ID NO:9, a polynucleotide that encodes CDRL1 comprises the nucleic acid sequence of SEQ ID NO:72, a polynucleotide that encodes CDRL2 comprises the nucleic acid sequence of SEQ ID NO:73, and a polynucleotide that encodes CDRL3 comprises the nucleic acid sequence of SEQ ID NO:74;

(ii) a polynucleotide that encodes CDRH1 comprises the nucleic acid sequence of SEQ ID NO:69, a polynucleotide that encodes CDRH2 comprises the nucleic acid sequence of SEQ ID NO:70, a polynucleotide that encodes CDRH3 comprises the nucleic acid sequence of SEQ ID NO:71, a polynucleotide that encodes CDRL1 comprises the nucleic acid sequence of SEQ ID NO:10, a polynucleotide that encodes CDRL2 comprises the nucleic acid sequence of SEQ ID NO:11, and a polynucleotide that encodes CDRL3 comprises the nucleic acid sequence of SEQ ID NO:12;

(iii) a polynucleotide that encodes CDRH1 comprises the nucleic acid sequence of SEQ ID NO:69, a polynucleotide that encodes CDRH2 comprises the nucleic acid sequence of SEQ ID NO:70, a polynucleotide that encodes CDRH3 comprises the nucleic acid sequence of SEQ ID NO:71, a polynucleotide that encodes CDRL1 comprises the nucleic acid sequence of SEQ ID NO:72, a polynucleotide that encodes CDRL2 comprises the nucleic acid sequence of SEQ ID NO:73, and a polynucleotide that encodes CDRL3 comprises the nucleic acid sequence of SEQ ID NO:74;

(iv) a polynucleotide that encodes CDRH1 comprises the nucleic acid sequence of SEQ ID NO:23, a polynucleotide that encodes CDRH2 comprises the nucleic acid sequence of SEQ ID NO:24, a polynucleotide that encodes CDRH3 comprises the nucleic acid sequence of SEQ ID NO:25, a polynucleotide that encodes CDRL1 comprises the nucleic acid sequence of SEQ ID NO:82, a polynucleotide that encodes CDRL2 comprises the nucleic acid sequence of SEQ ID NO:83, and a polynucleotide that encodes CDRL3 comprises the nucleic acid sequence of SEQ ID NO:84;

(v) a polynucleotide that encodes CDRH1 comprises the nucleic acid sequence of SEQ ID NO:79, a polynucleotide that encodes CDRH2 comprises the nucleic acid sequence of SEQ ID NO:80, a polynucleotide that encodes CDRH3 comprises the nucleic acid sequence of SEQ ID NO:81, a polynucleotide that encodes CDRL1 comprises the nucleic acid sequence of SEQ ID NO:26, a polynucleotide that encodes CDRL2 comprises the nucleic acid sequence of SEQ ID NO:27, and a polynucleotide that encodes CDRL3 comprises the nucleic acid sequence of SEQ ID NO:28; or (vi) a polynucleotide that encodes CDRH1 comprises the nucleic acid sequence of SEQ ID NO:79, a polynucleotide that encodes CDRH2 comprises the nucleic acid sequence of SEQ ID NO:80, a polynucleotide that encodes CDRH3 comprises the nucleic acid sequence of SEQ ID NO:81, a polynucleotide that encodes CDRL1 comprises the nucleic acid sequence of SEQ ID NO:82, a polynucleotide that encodes CDRL2 comprises the nucleic acid sequence of SEQ ID NO:83, and a polynucleotide that encodes CDRL3 comprises the nucleic acid sequence of SEQ ID NO:84;

wherein the encoded antibody or antigen-binding fragment thereof is capable of neutralizing a group A RSV infection and a group B RSV infection, and not a MPV infection, and wherein the encoded antibody or antigen-binding fragment thereof specifically binds to an RSV pre-fusion F protein and not to a RSV post-fusion F protein.

2. The isolated nucleic acid of claim 1, wherein the polynucleotide that encodes CDRH1 comprises the nucleic acid sequence of SEQ ID NO:7, the polynucleotide that encodes CDRH2 comprises the nucleic acid sequence of SEQ ID NO:8, the polynucleotide that encodes CDRH3 comprises the nucleic acid sequence of SEQ ID NO:9, the polynucleotide that encodes CDRL1 comprises the nucleic acid sequence of SEQ ID NO:72, the polynucleotide that encodes CDRL2 comprises the nucleic acid sequence of SEQ ID NO:73, and the polynucleotide that encodes CDRL3 comprises the nucleic acid sequence of SEQ ID NO:74.

3. The isolated nucleic acid of claim 1, wherein the polynucleotide that encodes CDRH1 comprises the nucleic acid sequence of SEQ ID NO:69, the polynucleotide that encodes CDRH2 comprises the nucleic acid sequence of SEQ ID NO:70, the polynucleotide that encodes CDRH3 comprises the nucleic acid sequence of SEQ ID NO:71, the polynucleotide that encodes CDRL1 comprises the nucleic acid sequence of SEQ ID NO:10, the polynucleotide that encodes CDRL2 comprises the nucleic acid sequence of SEQ ID NO:11, and the polynucleotide that encodes CDRL3 comprises the nucleic acid sequence of SEQ ID NO:12.

4. The isolated nucleic acid of claim 1, wherein the polynucleotide that encodes CDRH1 comprises the nucleic acid sequence of SEQ ID NO:69, the polynucleotide that encodes CDRH2 comprises the nucleic acid sequence of SEQ ID NO:70, the polynucleotide that encodes CDRH3 comprises the nucleic acid sequence of SEQ ID NO:71, the polynucleotide that encodes CDRL1 comprises the nucleic acid sequence of SEQ ID NO:72, the polynucleotide that encodes CDRL2 comprises the nucleic acid sequence of SEQ ID NO:73, and the polynucleotide that encodes CDRL3 comprises the nucleic acid sequence of SEQ ID NO:74.

5. The isolated nucleic acid of claim 1, wherein the polynucleotide that encodes CDRH1 comprises the nucleic acid sequence of SEQ ID NO:23, the polynucleotide that encodes CDRH2 comprises the nucleic acid sequence of SEQ ID NO:24, the polynucleotide that encodes CDRH3 comprises the nucleic acid sequence of SEQ ID NO:25, the polynucleotide that encodes CDRL1 comprises the nucleic acid sequence of SEQ ID NO:82, the polynucleotide that encodes CDRL2 comprises the nucleic acid sequence of SEQ ID NO:83, and the polynucleotide that encodes CDRL3 comprises the nucleic acid sequence of SEQ ID NO:84.

6. The isolated nucleic acid of claim 1, wherein the polynucleotide that encodes CDRH1 comprises the nucleic acid sequence of SEQ ID NO:79, the polynucleotide that encodes CDRH2 comprises the nucleic acid sequence of SEQ ID NO:80, the polynucleotide that encodes CDRH3 comprises the nucleic acid sequence of SEQ ID NO:81, the polynucleotide that encodes CDRL1 comprises the nucleic acid sequence of SEQ ID NO:26, the polynucleotide that encodes CDRL2 comprises the nucleic acid sequence of SEQ ID NO:27, and the polynucleotide that encodes CDRL3 comprises the nucleic acid sequence of SEQ ID NO:28.

7. The isolated nucleic acid of claim 1, wherein the polynucleotide that encodes CDRH1 comprises the nucleic acid sequence of SEQ ID NO:79, the polynucleotide that encodes CDRH2 comprises the nucleic acid sequence of SEQ ID NO:80, the polynucleotide that encodes CDRH3 comprises the nucleic acid sequence of SEQ ID NO:81, the polynucleotide that encodes CDRL1 comprises the nucleic acid sequence of SEQ ID NO:82, the polynucleotide that encodes CDRL2 comprises the nucleic acid sequence of SEQ ID NO:83, and the polynucleotide that encodes CDRL3 comprises the nucleic acid sequence of SEQ ID NO:84.

8. The isolated nucleic acid of claim 1, wherein the polynucleotide encoding the VH comprises or consists of the polynucleotide sequence of SEQ ID NO:15 and the polynucleotide encoding the VL comprises or consists of the polynucleotide sequence of SEQ ID NO:78.

9. The isolated nucleic acid of claim 1, wherein the polynucleotide encoding the VH comprises or consists of the polynucleotide sequence of SEQ ID NO:77 and the polynucleotide encoding the VL comprises or consists of the polynucleotide sequence of SEQ ID NO:16.

10. The isolated nucleic acid of claim 1, wherein the polynucleotide encoding the VH comprises or consists of the polynucleotide sequence of SEQ ID NO:77 and the polynucleotide encoding the VL comprises or consists of the polynucleotide sequence of SEQ ID NO:78.

11. The isolated nucleic acid of claim 1, wherein the polynucleotide encoding the VH comprises or consists of the polynucleotide sequence of SEQ ID NO:31 and the polynucleotide encoding the VL comprises or consists of the polynucleotide sequence of SEQ ID NO:88.

12. The isolated nucleic acid of claim 1, wherein the polynucleotide encoding the VH comprises or consists of the polynucleotide sequence of SEQ ID NO:87 and the polynucleotide encoding the VL comprises or consists of the polynucleotide sequence of SEQ ID NO:32.

13. The isolated nucleic acid of claim 1, wherein the polynucleotide encoding the VH comprises or consists of the polynucleotide sequence of SEQ ID NO:87 and the polynucleotide encoding the VL comprises or consists of the polynucleotide sequence of SEQ ID NO:88.

14. The isolated nucleic acid of claim 1, wherein the encoded antibody is HMB2435 variant 2, HMB2435 variant 3, HMB2435 variant 4, HMB2437 variant 2, HMB2437 variant 3, or HMB2437 variant 4.

15. The isolated nucleic acid of claim 1, wherein the encoded antibody or antigen-binding fragment thereof is a human antibody, a monoclonal antibody, a human monoclonal antibody, a purified antibody, a single chain antibody, a Fab, a Fab', a F(ab')2, a FIT or a scFv.

16. A vector, comprising the nucleic acid of claim 1.

17. A host cell, comprising the nucleic acid of claim 1 or the vector of claim 16.

18. A recombinant antibody, or an antigen-binding fragment thereof, comprising:
(i) a heavy chain variable region (VH) comprising or consisting of the amino acid sequence of SEQ ID NO:61 and a light chain variable region (VL) comprising or consisting of the amino acid sequence of SEQ ID NO:66;
(ii) a VH comprising or consisting of the amino acid sequence of SEQ ID NO:65 and a VL comprising or consisting of the amino acid sequence of SEQ ID NO:62;
(iii) a VH comprising or consisting of the amino acid sequence of SEQ ID NO:65 and a VL comprising or consisting of the amino acid sequence of SEQ ID NO:66;
(iv) a VH comprising or consisting of the amino acid sequence of SEQ ID NO:13 and a VL comprising or consisting of the amino acid sequence of SEQ ID NO:76;
(v) a VH comprising or consisting of the amino acid sequence of SEQ ID NO:75 and a VL comprising or consisting of the amino acid sequence of SEQ ID NO:14;
(vi) a VH comprising or consisting of the amino acid sequence of SEQ ID NO:75 and a VL comprising or consisting of the amino acid sequence of SEQ ID NO:76;
(vii) a VH comprising or consisting of the amino acid sequence of SEQ ID NO:29 and a VL comprising or consisting of the amino acid sequence of SEQ ID NO:86;
(viii) a VH comprising or consisting of the amino acid sequence of SEQ ID NO:85 and a VL comprising or consisting of the amino acid sequence of SEQ ID NO:30; or
(ix) a VH comprising or consisting of the amino acid sequence of SEQ ID NO:85 and a VL comprising or consisting of the amino acid sequence of SEQ ID NO:86;
wherein the antibody or antigen-binding fragment thereof is capable of neutralizing a group A RSV infection and a group B RSV infection, and not a MPV infection, and
wherein the antibody or antigen-binding fragment thereof specifically binds to an RSV pre-fusion F protein and not to a RSV post-fusion F protein.

19. The recombinant antibody, or an antigen-binding fragment thereof of claim 18, wherein:
(i) the VH consists of the amino acid sequence of SEQ ID NO:61 and the VL consists of the amino acid sequence of SEQ ID NO:66;
(ii) the VH consists of the amino acid sequence of SEQ ID NO:65 and the VL consists of the amino acid sequence of SEQ ID NO:62;
(iii) the VH consists of the amino acid sequence of SEQ ID NO:65 and the VL consists of the amino acid sequence of SEQ ID NO:66;
(iv) the VH consists of the amino acid sequence of SEQ ID NO:13 and the VL consists of the amino acid sequence of SEQ ID NO:76;
(v) the VH consists of the amino acid sequence of SEQ ID NO:75 and the VL consists of the amino acid sequence of SEQ ID NO:14;
(vi) the VH consists of the amino acid sequence of SEQ ID NO:75 and the VL consists of the amino acid sequence of SEQ ID NO:76;
(vii) the VH consists of the amino acid sequence of SEQ ID NO:29 and the VL consists of the amino acid sequence of SEQ ID NO:86;
(viii) the VH consists of the amino acid sequence of SEQ ID NO:85 and the VL consists of the amino acid sequence of SEQ ID NO:30; or
(ix) the VH consists of the amino acid sequence of SEQ ID NO:85 and the VL consists of the amino acid sequence of SEQ ID NO:86.

20. The recombinant antibody of claim 18, wherein the antibody is HMB2432 variant 2, HMB2432 variant 3, HMB2432 variant 4, HMB2435 variant 2, HMB2435 variant 3, HMB2435 variant 4, HMB2437 variant 2, HMB2437 variant 3, or HMB2437 variant 4.

21. The recombinant antibody of claim 18, wherein the antibody or antigen binding fragment is a human antibody, a monoclonal antibody, a human monoclonal antibody, a purified antibody, a single chain antibody, Fab, Fab', F(ab')2, Fv or scFv.

22. A cell expressing the antibody or antigen binding fragment of claim 18.

23. A vector comprising a polynucleotide encoding the antibody or antigen binding fragment of claim 18.

24. A pharmaceutical composition comprising the antibody or the antigen binding fragment thereof of claim 18, and a pharmaceutically acceptable excipient, diluent or carrier.

25. The pharmaceutical composition of claim 24, further comprising a second antibody or an antigen binding fragment thereof that neutralizes infection of RSV, MPV, PVM, or any combination thereof.

26. A method of reducing RSV group A or group B RSV infection, or lowering the risk of group A RSV or group B RSV infection, the method comprising administering to a subject in need thereof, a therapeutically effective amount of the antibody or the antigen binding fragment thereof of claim 18.

27. The method of claim 26, wherein:
   (i) the VH of the antibody or antigen-binding fragment thereof consists of the amino acid sequence of SEQ ID NO:61 and the VL of the antibody or antigen-binding fragment thereof consists of the amino acid sequence of SEQ ID NO:66;
   (ii) the VH of the antibody or antigen-binding fragment thereof consists of the amino acid sequence of SEQ ID NO:65 and the VL of the antibody or antigen-binding fragment thereof consists of the amino acid sequence of SEQ ID NO:62;
   (iii) the VH of the antibody or antigen-binding fragment thereof consists of the amino acid sequence of SEQ ID NO:65 and the VL of the antibody or antigen-binding fragment thereof consists of the amino acid sequence of SEQ ID NO:66;
   (iv) the VH of the antibody or antigen-binding fragment thereof consists of the amino acid sequence of SEQ ID NO:13 and the VL of the antibody or antigen-binding fragment thereof consists of the amino acid sequence of SEQ ID NO:76;
   (v) the VH of the antibody or antigen-binding fragment thereof consists of the amino acid sequence of SEQ ID NO:75 and the VL of the antibody or antigen-binding fragment thereof consists of the amino acid sequence of SEQ ID NO:14;
   (vi) the VH of the antibody or antigen-binding fragment thereof consists of the amino acid sequence of SEQ ID NO:75 and the VL of the antibody or antigen-binding fragment thereof consists of the amino acid sequence of SEQ ID NO:76;
   (vii) the VH of the antibody or antigen-binding fragment thereof consists of the amino acid sequence of SEQ ID NO:29 and the VL of the antibody or antigen-binding fragment thereof consists of the amino acid sequence of SEQ ID NO:86;
   (viii) the VH of the antibody or antigen-binding fragment thereof consists of the amino acid sequence of SEQ ID NO:85 and the VL of the antibody or antigen-binding fragment thereof consists of the amino acid sequence of SEQ ID NO:30; or
   (ix) the VH of the antibody or antigen-binding fragment thereof consists of the amino acid sequence of SEQ ID NO:85 and the VL of the antibody or antigen-binding fragment thereof consists of the amino acid sequence of SEQ ID NO:86.

28. The method of claim 26, wherein the antibody is HMB2432 variant 2, HMB2432 variant 3, HMB2432 variant 4, HMB2435 variant 2, HMB2435 variant 3, HMB2435 variant 4, HMB2437 variant 2, HMB2437 variant 3, or HMB2437 variant 4.

29. The method of claim 28, wherein the antibody is HMB2432 variant 3.

30. The method of claim 28, wherein the antibody is HMB2435 variant 3.

31. The method of claim 28, wherein the antibody is HMB2435 variant 4.

32. The method of claim 28, wherein the antibody is HMB2437 variant 2.

33. The method of claim 26, wherein the antibody or antigen binding fragment is a human antibody, a monoclonal antibody, a human monoclonal antibody, a purified antibody, a single chain antibody, Fab, Fab', F(ab')2, Fv or scFv.

* * * * *

UNITED STATES PATENT AND TRADEMARK OFFICE
CERTIFICATE OF CORRECTION

PATENT NO. : 10,047,145 B2
APPLICATION NO. : 14/911966
DATED : August 14, 2018
INVENTOR(S) : Davide Corti Page 1 of 1

It is certified that error appears in the above-identified patent and that said Letters Patent is hereby corrected as shown below:

In the Claims

Column 105, Claim 15, Line 48:
"Fab, a Fab', a F(ab')2, a FIT or a scFv" should read, -- Fab, a Fab', a F(ab')2, a Fv or a scFv --.

Signed and Sealed this
Tenth Day of November, 2020

Andrei Iancu
*Director of the United States Patent and Trademark Office*

SEQUENCE LISTING

<160> NUMBER OF SEQ ID NOS: 88

<210> SEQ ID NO 1
<211> LENGTH: 8

```
<212> TYPE: PRT
<213> ORGANISM: Artificial Sequence
<220> FEATURE:
<223> OTHER INFORMATION: HMB2435 ANTIBODY CDRH1 aa

<400> SEQUENCE: 1

Gly Phe Ala Phe Asn Asn Phe Ala
1               5

<210> SEQ ID NO 2
<211> LENGTH: 8
<212> TYPE: PRT
<213> ORGANISM: Artificial Sequence
<220> FEATURE:
<223> OTHER INFORMATION: HMB2435 ANTIBODY CDRH2 aa

<400> SEQUENCE: 2

Val Ser Tyr Asp Gly Thr Ser Pro
1               5

<210> SEQ ID NO 3
<211> LENGTH: 20
<212> TYPE: PRT
<213> ORGANISM: Artificial Sequence
<220> FEATURE:
<223> OTHER INFORMATION: HMB2435 ANTIBODY CDRH3 aa

<400> SEQUENCE: 3

Ala Arg Gly Leu Gly Ser Gly Ser Tyr Ser Trp Ile Gly Tyr Phe Tyr
1               5                   10                  15

Ala Met Asp Val
            20

<210> SEQ ID NO 4
<211> LENGTH: 9
<212> TYPE: PRT
<213> ORGANISM: Artificial Sequence
<220> FEATURE:
<223> OTHER INFORMATION: HMB2435 ANTIBODY CDRL1 aa

<400> SEQUENCE: 4

Ser Ser Asp Val Gly Gly Tyr Val Tyr
1               5

<210> SEQ ID NO 5

<400> SEQUENCE: 5

000

<210> SEQ ID NO 6
<211> LENGTH: 10
<212> TYPE: PRT
<213> ORGANISM: Artificial Sequence
<220> FEATURE:
<223> OTHER INFORMATION: HMB2435 ANTIBODY CDRL3 aa

<400> SEQUENCE: 6

Ile Ser Tyr Thr Asp Arg Asn Thr Val Val
1               5                   10

<210> SEQ ID NO 7
<211> LENGTH: 24
<212> TYPE: DNA
<213> ORGANISM: Artificial Sequence
<220> FEATURE:
<223> OTHER INFORMATION: HMB2435 ANTIBODY CDRH1 nuc
```

-continued

<400> SEQUENCE: 7
ggattcgcct tcaataattt tgct                                          24

<210> SEQ ID NO 8
<211> LENGTH: 24
<212> TYPE: DNA
<213> ORGANISM: Artificial Sequence
<220> FEATURE:
<223> OTHER INFORMATION: HMB2435 ANTIBODY CDRH2 nuc

<400> SEQUENCE: 8
gtgtcctatg acggaaccag tcca                                          24

<210> SEQ ID NO 9
<211> LENGTH: 60
<212> TYPE: DNA
<213> ORGANISM: Artificial Sequence
<220> FEATURE:
<223> OTHER INFORMATION: HMB2435 ANTIBODY CDRH3 nuc

<400> SEQUENCE: 9
gcgagagggc ttggttcggg gagttattcg tggattggtt acttttatgc aatggacgtc   60

<210> SEQ ID NO 10
<211> LENGTH: 27
<212> TYPE: DNA
<213> ORGANISM: Artificial Sequence
<220> FEATURE:
<223> OTHER INFORMATION: HMB2435 ANTIBODY CDRL1 nuc

<400> SEQUENCE: 10
agcagtgacg ttggtggtta tgtctat                                       27

<210> SEQ ID NO 11

<400> SEQUENCE: 11

000

<210> SEQ ID NO 12
<211> LENGTH: 30
<212> TYPE: DNA
<213> ORGANISM: Artificial Sequence
<220> FEATURE:
<223> OTHER INFORMATION: HMB2435 ANTIBODY CDRL3 nuc

<400> SEQUENCE: 12
atctcgtata ccgacagaaa cactgtcgtt                                    30

<210> SEQ ID NO 13
<211> LENGTH: 127
<212> TYPE: PRT
<213> ORGANISM: Artificial Sequence
<220> FEATURE:
<223> OTHER INFORMATION: HMB2435 ANTIBODY heavy chain aa

<400> SEQUENCE: 13

Gln Val Gln Leu Val Glu Ser Gly Gly Gly Val Val Gln Pro Gly Arg
1               5                   10                  15

Pro Leu Arg Leu Ser Cys Ala Ala Ser Gly Phe Ala Phe Asn Asn Phe
            20                  25                  30

Ala Leu His Trp Val Arg Gln Ala Pro Gly Lys Gly Pro Glu Trp Leu
        35                  40                  45

```
Ala Ala Val Ser Tyr Asp Gly Thr Ser Pro Tyr Tyr Ala Glu Ser Val
     50                  55                  60

Arg Ala Arg Phe Ser Ile Ser Arg Asp Asn Ser Lys Lys Thr Phe Tyr
65                  70                  75                  80

Leu Gln Leu Asp Ser Leu Arg Pro Glu Asp Thr Ala Val Tyr Tyr Cys
                85                  90                  95

Ala Arg Gly Leu Gly Ser Gly Ser Tyr Ser Trp Ile Gly Tyr Phe Tyr
            100                 105                 110

Ala Met Asp Val Trp Gly Arg Gly Thr Thr Val Thr Val Ser Ser
        115                 120                 125
```

<210> SEQ ID NO 14
<211> LENGTH: 110
<212> TYPE: PRT
<213> ORGANISM: Artificial Sequence
<220> FEATURE:
<223> OTHER INFORMATION: HMB2435 ANTIBODY light chain aa

<400> SEQUENCE: 14

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Val Tyr Val Ala Trp Tyr Gln Gln His Pro Gly Thr Ala Pro Lys Leu
        35                  40                  45

Ile Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Asp Ala Asp Tyr Tyr Cys Ile Ser Tyr Thr Asp Arg
                85                  90                  95

Asn Thr Val Val Phe Gly Gly Gly Thr Lys Leu Thr Val Leu
            100                 105                 110
```

<210> SEQ ID NO 15
<211> LENGTH: 381
<212> TYPE: DNA
<213> ORGANISM: Artificial Sequence
<220> FEATURE:
<223> OTHER INFORMATION: HMB2435 ANTIBODY heavy chain nuc

<400> SEQUENCE: 15

```
caggtgcagc tggtggagtc tgggggaggc gtggtccagc ctggggaggcc cctcagactc    60 tcctgtgcag cctctggatt cgccttcaat aattttgctt tacactgggt ccgccaggct   120
ccaggcaagg gtccagagtg gctggcagct gtgtcctatg acggaaccag tccatactac   180
gcagagtccg tcagggcccg attcagcatc tccagagaca attccaagaa acattctat   240 ctgcaattgg acagcctgcg acctgaagac acggctgtct attactgtgc gagagggctt   300
ggttcgggga gttattcgtg gattggttac ttttatgcaa tggacgtctg gggccgaggg   360
acgacggtca ccgtctcctc a                                              381
```

<210> SEQ ID NO 16
<211> LENGTH: 330
<212> TYPE: DNA
<213> ORGANISM: Artificial Sequence
<220> FEATURE:
<223> OTHER INFORMATION: HMB2435 ANTIBODY light chain nuc

<400> SEQUENCE: 16

```
cagtctgccc tgactcagcc tgcctccgtg tctgggtctc ctggacaatc gatcaccatc        60
tcctgcactg gaaccagcag tgacgttggt ggttatgtct atgtcgcctg gtaccaacaa       120
cacccaggca cagcccccaa actcatcatt tatgatgtca gtgatcggcc ctcaggggtt       180
tctaatcgat tctctgggtc caagtctggc aacacggcct ccctgaccat ctctgggctc       240
caggctgagg acgacgctga ttattactgc atctcgtata ccgacagaaa cactgtcgtt       300
tttggcggcg ggaccaagtt gaccgtcctg                                        330
```

<210> SEQ ID NO 17
<211> LENGTH: 10
<212> TYPE: PRT
<213> ORGANISM: Artificial Sequence
<220> FEATURE:
<223> OTHER INFORMATION: HMB2437 ANTIBODY CDRH1 aa

<400> SEQUENCE: 17

```
Gly Phe Ser Leu Thr Asp Ala Arg Met Gly
1               5                   10
```

<210> SEQ ID NO 18
<211> LENGTH: 7
<212> TYPE: PRT
<213> ORGANISM: Artificial Sequence
<220> FEATURE:
<223> OTHER INFORMATION: HMB2437 ANTIBODY CDRH2 aa

<400> SEQUENCE: 18

```
Ile Phe Ser Asn Asp Glu Lys
1               5
```

<210> SEQ ID NO 19
<211> LENGTH: 20
<212> TYPE: PRT
<213> ORGANISM: Artificial Sequence
<220> FEATURE:
<223> OTHER INFORMATION: HMB2437 ANTIBODY CDRH3 aa

<400> SEQUENCE: 19

```
Ala Arg Val Asp Gln Gly Trp Val Asn Thr Tyr Ser Ala Phe Tyr Tyr
1               5                   10                  15

Gly Met Asp Phe
            20
```

<210> SEQ ID NO 20
<211> LENGTH: 6
<212> TYPE: PRT
<213> ORGANISM: Artificial Sequence
<220> FEATURE:
<223> OTHER INFORMATION: HMB2437 ANTIBODY CDRL1 aa

<400> SEQUENCE: 20

```
Gln Tyr Ile Ser Thr His
1               5
```

<210> SEQ ID NO 21

<400> SEQUENCE: 21

000

<210> SEQ ID NO 22
<211> LENGTH: 9
<212> TYPE: PRT

```
<213> ORGANISM: Artificial Sequence
<220> FEATURE:
<223> OTHER INFORMATION: HMB2437 ANTIBODY CDRL3 aa

<400> SEQUENCE: 22

Gln Gln Thr Tyr Lys Thr Pro Ile Thr
1               5

<210> SEQ ID NO 23
<211> LENGTH: 30
<212> TYPE: DNA
<213> ORGANISM: Artificial Sequence
<220> FEATURE:
<223> OTHER INFORMATION: HMB2437 ANTIBODY CDRH1 nuc

<400> SEQUENCE: 23
ggattctcac tcacagatgc tagaatgggt                                    30

<210> SEQ ID NO 24
<211> LENGTH: 21
<212> TYPE: DNA
<213> ORGANISM: Artificial Sequence
<220> FEATURE:
<223> OTHER INFORMATION: HMB2437 ANTIBODY CDRH2 nuc

<400> SEQUENCE: 24
attttctcga atgacgaaaa a                                             21

<210> SEQ ID NO 25
<211> LENGTH: 60
<212> TYPE: DNA
<213> ORGANISM: Artificial Sequence
<220> FEATURE:
<223> OTHER INFORMATION: HMB2437 ANTIBODY CDRH3 nuc

<400> SEQUENCE: 25
gcacgagtcg atcagggatg ggtaaacacg tacagcgcct tttattatgg tatggacttc   60

<210> SEQ ID NO 26
<211> LENGTH: 18
<212> TYPE: DNA
<213> ORGANISM: Artificial Sequence
<220> FEATURE:
<223> OTHER INFORMATION: HMB2437 ANTIBODY CDRL1 nuc

<400> SEQUENCE: 26
cagtacatta gcacccat                                                 18

<210> SEQ ID NO 27

<400> SEQUENCE: 27

000

<210> SEQ ID NO 28
<211> LENGTH: 27
<212> TYPE: DNA
<213> ORGANISM: Artificial Sequence
<220> FEATURE:
<223> OTHER INFORMATION: HMB2437 ANTIBODY CDRL3 nuc

<400> SEQUENCE: 28
caacagactt ataaaacccc gatcacc                                       27

<210> SEQ ID NO 29
<211> LENGTH: 128
```

<212> TYPE: PRT
<213> ORGANISM: Artificial Sequence
<220> FEATURE:
<223> OTHER INFORMATION: HMB2437 ANTIBODY heavy chain aa

<400> SEQUENCE: 29

Gln Val Thr Leu Lys Glu Ser Gly Pro Val Leu Val Lys Pro Ser Glu
1               5                   10                  15

Thr Leu Thr Leu Thr Cys Thr Val Ser Gly Phe Ser Leu Thr Asp Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Phe Tyr Ser Thr Ser
    50                  55                  60

Leu Lys Thr Arg Leu Thr Ile Ser Lys Asp Thr Ser Thr Ser Gln Val
65                  70                  75                  80

Val Leu Arg Met Thr Asn Met Asp Pro Val Asp Thr Ala Thr Tyr Tyr
                85                  90                  95

Cys Ala Arg Val Asp Gln Gly Trp Val Asn Thr Tyr Ser Ala Phe Tyr
            100                 105                 110

Tyr Gly Met Asp Phe Trp Gly Gln Gly Thr Thr Val Thr Val Ser Ser
        115                 120                 125

<210> SEQ ID NO 30
<211> LENGTH: 107
<212> TYPE: PRT
<213> ORGANISM: Artificial Sequence
<220> FEATURE:
<223> OTHER INFORMATION: HMB2437 ANTIBODY light chain aa

<400> SEQUENCE: 30

Asp Ile Gln Met Thr Gln Ser Pro Ser Ser Leu Ser Ala Ser Val Gly
1               5                   10                  15

Glu Arg Val Thr Ile Thr Cys Arg Ala Ser Gln Tyr Ile Ser Thr His
            20                  25                  30

Leu Asn Trp Tyr Gln His Lys Pro Gly Lys Ala Pro Arg Leu Leu Ile
        35                  40                  45

Tyr Gly Ala Ser His Leu Glu Gly Gly Asp Pro Ser Arg Phe Ser Gly
    50                  55                  60

Ser Gly Ser Gly Thr Asp Phe Ser Leu Thr Ile Thr Ser Leu Gln Pro
65                  70                  75                  80

Glu Asp Phe Ala Thr Tyr Tyr Cys Gln Gln Thr Tyr Lys Thr Pro Ile
                85                  90                  95

Thr Phe Ala Gln Gly Thr Arg Leu Glu Ile Lys
            100                 105

<210> SEQ ID NO 31
<211> LENGTH: 384
<212> TYPE: DNA
<213> ORGANISM: Artificial Sequence
<220> FEATURE:
<223> OTHER INFORMATION: HMB2437 ANTIBODY heavy chain nuc

<400> SEQUENCE: 31
caggtcacct tgaaggagtc tggtcctgtg ctggtgaaac cctcagagac cctcacgctg      60
acctgcaccg tctctggatt ctcactcaca gatgctagaa tgggtgtgag ttggatccgt     120
cagcccccag ggaaggccct ggagtggctt gcacacattt tctcgaatga cgaaaaattc     180
tacagcacat ctctgaagac caggctcacc atctccaagg acacctccac aagccaggtg     240

```
gtccttagga tgaccaacat ggaccctgtg acacagcca cttattattg tgcacgagtc    300
gatcagggat gggtaaacac gtacagcgcc ttttattatg gtatggactt ctggggccaa    360
gggaccacgg tcaccgtctc ctca                                          384
```

<210> SEQ ID NO 32
<211> LENGTH: 321
<212> TYPE: DNA
<213> ORGANISM: Artificial Sequence
<220> FEATURE:
<223> OTHER INFORMATION: HMB2437 ANTIBODY light chain nuc

<400> SEQUENCE: 32

```
gacatccaga tgacccagtc tccatcctcc ctgtctgcat ctgtaggaga aagagtcacc    60
atcacttgcc gggcaagtca gtacattagc acccatttaa attggtatca gcacaaacca   120
gggaaagccc ctcgtctcct gatctatggt gcctcccatt tggaaggtgg ggacccatca   180
cggttcagtg gcagtggatc tgggacagat ttcagtctca ccattaccag tctgcaacct   240
gaagattttg caacttacta ctgtcaacag acttataaaa ccccgatcac cttcgcccaa   300
gggacacgac tggagattaa a                                             321
```

<210> SEQ ID NO 33
<211> LENGTH: 10
<212> TYPE: PRT
<213> ORGANISM: Artificial Sequence
<220> FEATURE:
<223> OTHER INFORMATION: HMB2416 ANTIBODY CDRH1 aa

<400> SEQUENCE: 33

Gly Gly Ser Ile Ser Ser Gly Asp Tyr Tyr
1               5                   10

<210> SEQ ID NO 34
<211> LENGTH: 7
<212> TYPE: PRT
<213> ORGANISM: Artificial Sequence
<220> FEATURE:
<223> OTHER INFORMATION: HMB2416 ANTIBODY CDRH2 aa

<400> SEQUENCE: 34

Ile Tyr Phe Ser Gly Ser Thr
1               5

<210> SEQ ID NO 35
<211> LENGTH: 15
<212> TYPE: PRT
<213> ORGANISM: Artificial Sequence
<220> FEATURE:
<223> OTHER INFORMATION: HMB2416 ANTIBODY CDRH3 aa

<400> SEQUENCE: 35

Ala Arg Glu Asp Thr Thr Met Ala Ile Pro Tyr Tyr Phe Asp Pro
1               5                   10                  15

<210> SEQ ID NO 36
<211> LENGTH: 6
<212> TYPE: PRT
<213> ORGANISM: Artificial Sequence
<220> FEATURE:
<223> OTHER INFORMATION: HMB2416 ANTIBODY CDRL1 aa

<400> SEQUENCE: 36

Asn Ile Gly Asn Glu Asn

<210> SEQ ID NO 37

<400> SEQUENCE: 37

000

<210> SEQ ID NO 38
<211> LENGTH: 11
<212> TYPE: PRT
<213> ORGANISM: Artificial Sequence
<220> FEATURE:
<223> OTHER INFORMATION: HMB2416 ANTIBODY CDRL3 aa

<400> SEQUENCE: 38

Gln Val Trp Asp Ser Ser Thr Asp Gln Val Val
1               5                   10

<210> SEQ ID NO 39
<211> LENGTH: 30
<212> TYPE: DNA
<213> ORGANISM: Artificial Sequence
<220> FEATURE:
<223> OTHER INFORMATION: HMB2416 ANTIBODY CDRH1 nuc

<400> SEQUENCE: 39
ggtggctcca tcagcagtgg tgattactac                              30

<210> SEQ ID NO 40
<211> LENGTH: 21
<212> TYPE: DNA
<213> ORGANISM: Artificial Sequence
<220> FEATURE:
<223> OTHER INFORMATION: HMB2416 ANTIBODY CDRH2 nuc

<400> SEQUENCE: 40
atctacttca gtggcagcac c                                       21

<210> SEQ ID NO 41
<211> LENGTH: 45
<212> TYPE: DNA
<213> ORGANISM: Artificial Sequence
<220> FEATURE:
<223> OTHER INFORMATION: HMB2416 ANTIBODY CDRH3 nuc

<400> SEQUENCE: 41
gccagagagg atacaactat ggctattcca tactacttcg acccc              45

<210> SEQ ID NO 42
<211> LENGTH: 18
<212> TYPE: DNA
<213> ORGANISM: Artificial Sequence
<220> FEATURE:
<223> OTHER INFORMATION: HMB2416 ANTIBODY CDRL1 nuc

<400> SEQUENCE: 42
aatattggaa atgaaaat                                           18

<210> SEQ ID NO 43

<400> SEQUENCE: 43

000

<210> SEQ ID NO 44

```
<211> LENGTH: 33
<212> TYPE: DNA
<213> ORGANISM: Artificial Sequence
<220> FEATURE:
<223> OTHER INFORMATION: HMB2416 ANTIBODY CDRL3 nuc

<400> SEQUENCE: 44
caggtgtggg atagtagtac tgatcaagtg gta                                    33

<210> SEQ ID NO 45
<211> LENGTH: 123
<212> TYPE: PRT
<213> ORGANISM: Artificial Sequence
<220> FEATURE:
<223> OTHER INFORMATION: HMB2416 ANTIBODY heavy chain aa

<400> SEQUENCE: 45

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Phe Ser Gly Ser Thr Tyr Tyr Asn Pro Ser
    50                  55                  60

Leu Lys Ser Arg Val Thr Met Ser Gly Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Glu Asp Thr Thr Met Ala Ile Pro Tyr Tyr Phe Asp Pro
            100                 105                 110

Trp Gly Arg Gly Ile Leu Val Thr Val Ser Ser
        115                 120

<210> SEQ ID NO 46
<211> LENGTH: 108
<212> TYPE: PRT
<213> ORGANISM: Artificial Sequence
<220> FEATURE:
<223> OTHER INFORMATION: HMB2416 ANTIBODY light chain aa

<400> SEQUENCE: 46

Ser Tyr Val Leu Thr Gln Pro Pro Ser Val Ser Val Ala Pro Gly Arg
 1               5                  10                  15

Thr Ala Arg Ile Thr Cys Gly Arg His Asn Ile Gly Asn Glu Asn Val
            20                  25                  30

His Trp Tyr Gln Gln Arg Pro Gly Gln Ala Pro Val Leu Val Ile Tyr
        35                  40                  45

Ser Asp Ser Asp Arg Pro Ser Gly Ile Pro Glu Arg Phe Ser Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Ser Ser Thr Asp Gln
                85                  90                  95

Val Val Phe Gly Gly Gly Thr Lys Leu Thr Val Leu
            100                 105

<210> SEQ ID NO 47
<211> LENGTH: 369
<212> TYPE: DNA
```

<213> ORGANISM: Artificial Sequence
<220> FEATURE:
<223> OTHER INFORMATION: HMB2416 ANTIBODY heavy chain nuc

<400> SEQUENCE: 47

```
caggtgcagc tgcaggagtc gggcccagga ctcgtgaagc cttcacagac cctgtccctc    60
acctgcactg tctctggtgg ctccatcagc agtggtgatt actactggag ttggatccgc   120
cagcccccag ggaagggcct ggagtggatt gggtacatct acttcagtgg cagcacctac   180
tacaatccgt ccctcaagag tcgagttacc atgtcagggg acacgtccaa gaatcagttc   240
tccctgaggc tgagctctgt gactgccgca gacacggccg tgtattattg tgccagagag   300
gatacaacta tggctattcc atactacttc gaccctgggg ccggggaat cctggtcacc   360
gtctcctca                                                           369
```

<210> SEQ ID NO 48
<211> LENGTH: 324
<212> TYPE: DNA
<213> ORGANISM: Artificial Sequence
<220> FEATURE:
<223> OTHER INFORMATION: HMB2416 ANTIBODY light chain nuc

<400> SEQUENCE: 48

```
tcctatgtcc tgactcagcc accctcagtg tcagtggccc ccggaaggac ggccaggatc    60
acctgtggga gacataatat tggaaatgaa aatgttcact ggtaccagca gaggccaggc   120
caggcccctg tgctggtcat ctattctgat agcgaccggc cctcagggat ccctgagcga   180
ttctctggct ccaactctgg gaacacggcc accctaagca tcagcagggt cgaagccggg   240
gatgaggccg actattattg tcaggtgtgg gatagtagta ctgatcaagt ggtattcggc   300
ggagggacca agctgaccgt ccta                                          324
```

<210> SEQ ID NO 49
<211> LENGTH: 8
<212> TYPE: PRT
<213> ORGANISM: Artificial Sequence
<220> FEATURE:
<223> OTHER INFORMATION: HMB2432 ANTIBODY CDRH1 aa

<400> SEQUENCE: 49

Gly Phe Ser Phe Ser Asn Tyr Trp
1               5

<210> SEQ ID NO 50
<211> LENGTH: 8
<212> TYPE: PRT
<213> ORGANISM: Artificial Sequence
<220> FEATURE:
<223> OTHER INFORMATION: HMB2432 ANTIBODY CDRH2 aa

<400> SEQUENCE: 50

Val Tyr Pro Ala Asp Ser Asp Thr
1               5

<210> SEQ ID NO 51
<211> LENGTH: 21
<212> TYPE: PRT
<213> ORGANISM: Artificial Sequence
<220> FEATURE:
<223> OTHER INFORMATION: HMB2432 ANTIBODY CDRH3 aa

<400> SEQUENCE: 51

Val Arg Gln Ile Gly Gly Val Val Thr Thr Ala Thr Asp Asp Tyr Phe

Tyr Gly Met Asp Ile
            20

<210> SEQ ID NO 52
<211> LENGTH: 6
<212> TYPE: PRT
<213> ORGANISM: Artificial Sequence
<220> FEATURE:
<223> OTHER INFORMATION: HMB2432 ANTIBODY CDRL1 aa

<400> SEQUENCE: 52

Gln Thr Val Lys Ser Phe
1               5

<210> SEQ ID NO 53

<400> SEQUENCE: 53

000

<210> SEQ ID NO 54
<211> LENGTH: 9
<212> TYPE: PRT
<213> ORGANISM: Artificial Sequence
<220> FEATURE:
<223> OTHER INFORMATION: HMB2432 ANTIBODY CDRL3 aa

<400> SEQUENCE: 54

Gln Gln Ser Tyr Arg Thr Pro Leu Thr
1               5

<210> SEQ ID NO 55
<211> LENGTH: 24
<212> TYPE: DNA
<213> ORGANISM: Artificial Sequence
<220> FEATURE:
<223> OTHER INFORMATION: HMB2432 ANTIBODY CDRH1 nuc

<400> SEQUENCE: 55
ggatttagtt ttagcaacta ttgg                                          24

<210> SEQ ID NO 56
<211> LENGTH: 24
<212> TYPE: DNA
<213> ORGANISM: Artificial Sequence
<220> FEATURE:
<223> OTHER INFORMATION: HMB2432 ANTIBODY CDRH2 nuc

<400> SEQUENCE: 56
gtctatccgg ctgactctga cacc                                          24

<210> SEQ ID NO 57
<211> LENGTH: 63
<212> TYPE: DNA
<213> ORGANISM: Artificial Sequence
<220> FEATURE:
<223> OTHER INFORMATION: HMB2432 ANTIBODY CDRH3 nuc

<400> SEQUENCE: 57
gtgagacaaa tcggggggt ggtgacaact gctactgacg actacttcta cggtatggac    60
atc                                                                 63

<210> SEQ ID NO 58
<211> LENGTH: 18

```
<212> TYPE: DNA
<213> ORGANISM: Artificial Sequence
<220> FEATURE:
<223> OTHER INFORMATION: HMB2432 ANTIBODY CDRL1 nuc

<400> SEQUENCE: 58
cagaccgtta aaagcttt                                                 18

<210> SEQ ID NO 59

<400> SEQUENCE: 59

000

<210> SEQ ID NO 60
<211> LENGTH: 27
<212> TYPE: DNA
<213> ORGANISM: Artificial Sequence
<220> FEATURE:
<223> OTHER INFORMATION: HMB2432 ANTIBODY CDRL3 nuc

<400> SEQUENCE: 60
caacagagtt acaggacccc tctgacg                                       27

<210> SEQ ID NO 61
<211> LENGTH: 128
<212> TYPE: PRT
<213> ORGANISM: Artificial Sequence
<220> FEATURE:
<223> OTHER INFORMATION: HMB2432 ANTIBODY heavy chain 1 aa

<400> SEQUENCE: 61
```

Glu Val Gln Leu Val Gln Ser Gly Ala Glu Val Lys Lys Pro Gly Thr
1               5                   10                  15

Ser Leu Lys Ile Ser Cys Lys Gly Ser Gly Phe Ser Phe Ser Asn Tyr
            20                  25                  30

Trp Ile Gly Trp Val Arg Gln Met Pro Gly Lys Gly Leu Glu Trp Met
        35                  40                  45

Gly Ile Val Tyr Pro Ala Asp Ser Asp Thr Arg Tyr Ser Pro Ser Phe
    50                  55                  60

Gln Gly Gln Val Thr Ile Ser Gly Asp Asn Ser Ile Asn Thr Ala Tyr
65                  70                  75                  80

Leu Gln Trp Ser Arg Leu Lys Ala Ser Asp Thr Ala Thr Tyr Tyr Cys
                85                  90                  95

Val Arg Gln Ile Gly Gly Val Val Thr Thr Ala Thr Asp Asp Tyr Phe
            100                 105                 110

Tyr Gly Met Asp Ile Trp Gly Pro Gly Thr Thr Val Ile Val Ser Ser
        115                 120                 125

```
<210> SEQ ID NO 62
<211> LENGTH: 107
<212> TYPE: PRT
<213> ORGANISM: Artificial Sequence
<220> FEATURE:
<223> OTHER INFORMATION: HMB2432 ANTIBODY light chain 1 aa

<400> SEQUENCE: 62
```

Glu Thr Thr Leu Thr Gln Ser Pro Ser Ser Leu Ser Ala Ser Val Gly
1               5                   10                  15

Asp Arg Val Thr Ile Thr Cys Arg Ala Ser Gln Thr Val Lys Ser Phe
            20                  25                  30

Leu Asn Trp Tyr Gln Gln Lys Pro Gly Lys Ala Pro Lys Leu Leu Ile

```
            35                  40                  45
Tyr Asp Ala Ser Asp Leu Gln Ser Gly Val Pro Ser Arg Phe Ser Gly
        50                  55                  60

Ser Gly Ser Gly Thr Asp Phe Thr Leu Thr Ile Ser Arg Leu Gln Pro
65                  70                  75                  80

Glu Asp Phe Ala Thr Tyr Phe Cys Gln Gln Ser Tyr Arg Thr Pro Leu
                85                  90                  95

Thr Phe Gly Gln Gly Thr Arg Val Glu Ile Lys
            100                 105
```

```
<210> SEQ ID NO 63
<211> LENGTH: 384
<212> TYPE: DNA
<213> ORGANISM: Artificial Sequence
<220> FEATURE:
<223> OTHER INFORMATION: HMB2432 ANTIBODY heavy chain 1 nuc

<400> SEQUENCE: 63
gaggtgcagc tggtgcagtc tggagcggag gtgaaaaaac ccggacgtc tctgaagatc     60 tcctgcaagg gttctggatt tagttttagc aactattgga tcggctgggt gcgccagatg   120
cccgggaaag gctggagtg gatggggatc gtctatccgg ctgactctga caccagatac   180
agcccgtcct ccagggcca ggtcaccatc tcaggcgaca actccatcaa taccgcctac   240
ctgcagtgga gccgctgaa ggcctcggac accgccacct attactgtgt gagacaaatc   300
gggggggtgg tgacaactgc tactgacgac tacttctacg gtatggacat ctggggccca   360
gggaccacgg tcatcgtctc ctca                                          384

<210> SEQ ID NO 64
<211> LENGTH: 321
<212> TYPE: DNA
<213> ORGANISM: Artificial Sequence
<220> FEATURE:
<223> OTHER INFORMATION: HMB2432 ANTIBODY light chain 1 nuc

<400> SEQUENCE: 64
gaaacgacac tcacgcagtc tccatcctcc ctgtctgcat ctgtaggaga cagagtcacc     60
atcacttgcc gggcaagtca gaccgttaaa agcttttaa attggtatca gcagaagcca   120
gggaaagccc ctaaactcct gatctatgat gcatccgatt tgcaaagtgg ggtcccatcc   180
aggttcagtg gcagtggatc tgggacagat ttcactctca ccatcagccg tctgcaacct   240
gaagattttg caacttactt ctgtcaacag agttacagga cccctctgac gttcggccaa   300
gggaccaggg tggaaatcaa a                                             321

<210> SEQ ID NO 65
<211> LENGTH: 128
<212> TYPE: PRT
<213> ORGANISM: Artificial Sequence
<220> FEATURE:
<223> OTHER INFORMATION: HMB2432 ANTIBODY heavy chain 2 aa

<400> SEQUENCE: 65

Glu Val Gln Leu Val Gln Ser Gly Ala Glu Val Lys Lys Pro Gly Thr
1               5                   10                  15

Ser Leu Lys Ile Ser Cys Lys Gly Ser Gly Phe Ser Phe Ser Asn Tyr
            20                  25                  30

Trp Ile Gly Trp Val Arg Gln Met Pro Gly Lys Gly Leu Glu Trp Met
        35                  40                  45
```

Gly Ile Val Tyr Pro Ala Asp Ser Asp Thr Arg Tyr Ser Pro Ser Phe
     50                  55                  60

Gln Gly Gln Val Thr Ile Ser Gly Asp Asn Ser Ile Asn Thr Ala Tyr
65                  70                  75                  80

Leu Gln Trp Ser Arg Leu Lys Ala Ser Asp Thr Ala Thr Tyr Tyr Cys
                 85                  90                  95

Val Arg Gln Ile Gly Gly Val Val Thr Thr Ala Thr Asp Asp Tyr Phe
            100                 105                 110

Tyr Gly Met Asp Ile Trp Gly Pro Gly Thr Thr Val Thr Val Ser Ser
            115                 120                 125

<210> SEQ ID NO 66
<211> LENGTH: 107
<212> TYPE: PRT
<213> ORGANISM: Artificial Sequence
<220> FEATURE:
<223> OTHER INFORMATION: HMB2432 ANTIBODY light chain 2 aa

<400> SEQUENCE: 66

Glu Thr Thr Leu Thr Gln Ser Pro Ser Ser Leu Ser Ala Ser Val Gly
1               5                   10                  15

Asp Arg Val Thr Ile Thr Cys Arg Ala Ser Gln Thr Val Lys Ser Phe
            20                  25                  30

Leu Asn Trp Tyr Gln Gln Lys Pro Gly Lys Ala Pro Lys Leu Leu Ile
         35                  40                  45

Tyr Asp Ala Ser Asp Leu Gln Ser Gly Val Pro Ser Arg Phe Ser Gly
     50                  55                  60

Ser Gly Ser Gly Thr Asp Phe Thr Leu Thr Ile Ser Arg Leu Gln Pro
65                  70                  75                  80

Glu Asp Phe Ala Thr Tyr Phe Cys Gln Gln Ser Tyr Arg Thr Pro Leu
                 85                  90                  95

Thr Phe Gly Gln Gly Thr Lys Val Glu Ile Lys
            100                 105

<210> SEQ ID NO 67
<211> LENGTH: 384
<212> TYPE: DNA
<213> ORGANISM: Artificial Sequence
<220> FEATURE:
<223> OTHER INFORMATION: HMB2432 ANTIBODY heavy chain 2 nuc

<400> SEQUENCE: 67
gaggtgcagc tggtgcagtc tggagcggag gtgaaaaaac ccggggacgtc tctgaagatc      60 tcctgcaagg gttctggatt tagttttagc aactattgga tcggctgggt gcgccagatg     120
cccgggaaag gcctggagtg gatggggatc gtctatccgg ctgactctga caccagatac     180
agcccgtcct tccagggcca ggtcaccatc tcaggcgaca actccatcaa taccgcctac     240
ctgcagtgga gccgcctgaa ggcctcggac accgccacct attactgtgt gagacaaatc     300 ggggggggtgg tgacaactgc tactgacgac tacttctacg gtatggacat ctggggccca     360
gggaccacgg tcaccgtctc ctca                                             384

<210> SEQ ID NO 68
<211> LENGTH: 321
<212> TYPE: DNA
<213> ORGANISM: Artificial Sequence
<220> FEATURE:
<223> OTHER INFORMATION: HMB2432 ANTIBODY light chain 2 nuc

<400> SEQUENCE: 68

```
gaaacgacac tcacgcagtc tccatcctcc ctgtctgcat ctgtaggaga cagagtcacc      60
atcacttgcc gggcaagtca gaccgttaaa agcttttaa attggtatca gcagaagcca     120
gggaaagccc ctaaactcct gatctatgat gcatccgatt tgcaaagtgg ggtcccatcc    180
aggttcagtg gcagtggatc tgggacagat ttcactctca ccatcagccg tctgcaacct   240
gaagattttg caacttactt ctgtcaacag agttacagga cccctctgac gttcggccaa    300
gggaccaagg tggaaatcaa a                                               321
```

<210> SEQ ID NO 69
<211> LENGTH: 24
<212> TYPE: DNA
<213> ORGANISM: Artificial Sequence
<220> FEATURE:
<223> OTHER INFORMATION: HMB2435 ANTIBODY FRAMEWORK REGIONS GERMLINED
      (FR-GL) VARIANTS CDRH1 nuc

<400> SEQUENCE: 69

```
ggcttcgctt ttaacaattt cgca                                             24
```

<210> SEQ ID NO 70
<211> LENGTH: 24
<212> TYPE: DNA
<213> ORGANISM: Artificial Sequence
<220> FEATURE:
<223> OTHER INFORMATION: HMB2435 ANTIBODY FRAMEWORK REGIONS GERMLINED
      (FR-GL) VARIANTS CDRH2 nuc

<400> SEQUENCE: 70

```
gtcagttacg acgggacttc acct                                             24
```

<210> SEQ ID NO 71
<211> LENGTH: 60
<212> TYPE: DNA
<213> ORGANISM: Artificial Sequence
<220> FEATURE:
<223> OTHER INFORMATION: HMB2435 ANTIBODY FRAMEWORK REGIONS GERMLINED
      (FR-GL) VARIANTS CDRH3 nuc

<400> SEQUENCE: 71

```
gccagaggac tgggcagcgg gtcctattct tggatcggct acttctatgc tatggatgtg      60
```

<210> SEQ ID NO 72
<211> LENGTH: 27
<212> TYPE: DNA
<213> ORGANISM: Artificial Sequence
<220> FEATURE:
<223> OTHER INFORMATION: HMB2435 ANTIBODY FRAMEWORK REGIONS GERMLINED
      (FR-GL) VARIANTS CDRL1 nuc

<400> SEQUENCE: 72

```
agctccgacg tcggaggata cgtgtat                                          27
```

<210> SEQ ID NO 73

<400> SEQUENCE: 73

000

<210> SEQ ID NO 74
<211> LENGTH: 30
<212> TYPE: DNA
<213> ORGANISM: Artificial Sequence
<220> FEATURE:
<223> OTHER INFORMATION: HMB2435 ANTIBODY FRAMEWORK REGIONS GERMLINED (FR-GL) VARIANTS CDRL3 nuc

<400> SEQUENCE: 74
attagctaca ccgacaggaa tacagtggtc                                              30

<210> SEQ ID NO 75
<211> LENGTH: 127
<212> TYPE: PRT
<213> ORGANISM: Artificial Sequence
<220> FEATURE:
<223> OTHER INFORMATION: HMB2435 ANTIBODY FRAMEWORK REGIONS GERMLINED
      (FR-GL) VARIANTS heavy chain FR-GL aa

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Asn Asn Phe
            20                  25                  30

Ala Met His Trp Val Arg Gln Ala Pro Gly Lys Gly Leu Glu Trp Val
        35                  40                  45

Ala Val Val Ser Tyr Asp Gly Thr Ser Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Gly Ser Gly Ser Tyr Ser Trp Ile Gly Tyr Phe Tyr
            100                 105                 110

Ala Met Asp Val Trp Gly Gln Gly Thr Thr Val Thr Val Ser Ser
        115                 120                 125

<210> SEQ ID NO 76
<211> LENGTH: 110
<212> TYPE: PRT
<213> ORGANISM: Artificial Sequence
<220> FEATURE:
<223> OTHER INFORMATION: HMB2435 ANTIBODY FRAMEWORK REGIONS GERMLINED
      (FR-GL) VARIANTS light chain FR-GL aa

<400> SEQUENCE: 76

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Val Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ile Ser Tyr Thr Asp Arg
                85                  90                  95

Asn Thr Val Val Phe Gly Gly Gly Thr Lys Leu Thr Val Leu
            100                 105                 110

<210> SEQ ID NO 77
<211> LENGTH: 381
<212> TYPE: DNA
<213> ORGANISM: Artificial Sequence
<220> FEATURE:

<223> OTHER INFORMATION: HMB2435 ANTIBODY FRAMEWORK REGIONS GERMLINED
(FR-GL) VARIANTS heavy chain FR-GL nuc

<400> SEQUENCE: 77

```
caggtgcagc tggtcgagtc tggaggagga gtggtccagc caggacggag tctgagactg      60
tcatgcgccg ctagcggctt cgcttttaac aatttcgcaa tgcactgggt gcggcaggca     120
ccaggcaagg gactggaatg ggtcgctgtg gtcagttacg acgggacttc accttactat     180
gccgatagcg tgaagggcag gtttaccatc tcccgcgaca actctaaaaa tacactgtac     240
ctgcagatga actccctgcg agcagaggat accgccgtgt actattgtgc cagaggactg     300
ggcagcgggt cctattcttg gatcggctac ttctatgcta tggatgtgtg ggggcagggc     360
actaccgtca ctgtgtcttc a                                                381
```

<210> SEQ ID NO 78
<211> LENGTH: 330
<212> TYPE: DNA
<213> ORGANISM: Artificial Sequence
<220> FEATURE:
<223> OTHER INFORMATION: HMB2435 ANTIBODY FRAMEWORK REGIONS GERMLINED
(FR-GL) VARIANTS light chain FR-GL nuc

<400> SEQUENCE: 78

```
cagtccgcac tgactcagcc agcctctgtg agtggatcac ccggccagag catcacaatt      60
tcctgcaccg gcacaagctc cgacgtcgga ggatacgtgt atgtctcttg gtaccagcag     120
caccccggca aggctcctaa actgatgatc tatgatgtga gcaaccggcc cagtggggtc     180
tcaaatagat tcagcgggtc caagtctgga aacacagcct ctctgactat cagtggcctg     240
caggccgagg acgaagctga ttactattgt gttattagcta ccgacaggaa tacagtggtc     300
tttggaggcg ggactaaact gaccgtgctg                                       330
```

<210> SEQ ID NO 79
<211> LENGTH: 30
<212> TYPE: DNA
<213> ORGANISM: Artificial Sequence
<220> FEATURE:
<223> OTHER INFORMATION: HMB2437 ANTIBODY FRAMEWORK REGIONS GERMLINED
(FR-GL) VARIANTS CDRH1 nuc

<400> SEQUENCE: 79

```
ggcttctccc tgaccgacgc tcggatgggg                                        30
```

<210> SEQ ID NO 80
<211> LENGTH: 21
<212> TYPE: DNA
<213> ORGANISM: Artificial Sequence
<220> FEATURE:
<223> OTHER INFORMATION: HMB2437 ANTIBODY FRAMEWORK REGIONS GERMLINED
(FR-GL) VARIANTS CDRH2 nuc

<400> SEQUENCE: 80

```
atttttagca acgacgaaaa g                                                 21
```

<210> SEQ ID NO 81
<211> LENGTH: 60
<212> TYPE: DNA
<213> ORGANISM: Artificial Sequence
<220> FEATURE:
<223> OTHER INFORMATION: HMB2437 ANTIBODY FRAMEWORK REGIONS GERMLINED
(FR-GL) VARIANTS CDRH3 nuc

<400> SEQUENCE: 81

```
gcccgggtgg atcagggtg ggtcaatacc tattcagcct tctattatgg aatggacttc     60
```

<210> SEQ ID NO 82
<211> LENGTH: 18
<212> TYPE: DNA
<213> ORGANISM: Artificial Sequence
<220> FEATURE:
<223> OTHER INFORMATION: HMB2437 ANTIBODY FRAMEWORK REGIONS GERMLINED
      (FR-GL) VARIANTS CDRL1 nuc

<400> SEQUENCE: 82

```
cagtacattt ctacacac                                                  18
```

<210> SEQ ID NO 83

<400> SEQUENCE: 83

000

<210> SEQ ID NO 84
<211> LENGTH: 27
<212> TYPE: DNA
<213> ORGANISM: Artificial Sequence
<220> FEATURE:
<223> OTHER INFORMATION: HMB2437 ANTIBODY FRAMEWORK REGIONS GERMLINED
      (FR-GL) VARIANTS CDRL3 nuc

<400> SEQUENCE: 84

```
cagcagacat ataaaactcc catcacc                                        27
```

<210> SEQ ID NO 85
<211> LENGTH: 128
<212> TYPE: PRT
<213> ORGANISM: Artificial Sequence
<220> FEATURE:
<223> OTHER INFORMATION: HMB2437 ANTIBODY FRAMEWORK REGIONS GERMLINED
      (FR-GL) VARIANTS heavy chain FR-GL aa

<400> SEQUENCE: 85

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asp Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Val Asp Gln Gly Trp Val Asn Thr Tyr Ser Ala Phe Tyr
            100                 105                 110

Tyr Gly Met Asp Phe Trp Gly Gln Gly Thr Thr Val Thr Val Ser Ser
        115                 120                 125

<210> SEQ ID NO 86
<211> LENGTH: 107
<212> TYPE: PRT
<213> ORGANISM: Artificial Sequence
<220> FEATURE:
<223> OTHER INFORMATION: HMB2437 ANTIBODY FRAMEWORK REGIONS GERMLINED
      (FR-GL) VARIANTS light chain FR-GL aa

```
<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Ser Thr His
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Thr Tyr Lys Thr Pro Ile
                85                  90                  95

Thr Phe Gly Gln Gly Thr Arg Leu Glu Ile Lys
            100                 105

<210> SEQ ID NO 87
<211> LENGTH: 384
<212> TYPE: DNA
<213> ORGANISM: Artificial Sequence
<220> FEATURE:
<223> OTHER INFORMATION: HMB2437 ANTIBODY FRAMEWORK REGIONS GERMLINED
      (FR-GL) VARIANTS heavy chain FR-GL nuc

<400> SEQUENCE: 87
caagtgactc tgaaggagtc tggcccagtg ctggtcaaac ccaccgaaac actgactctg      60
acctgcacag tgagcggctt ctccctgacc gacgctcgga tgggggtctc ctggatcaga    120
cagccacctg gaaaggcact ggagtggctg gctcacattt ttagcaacga cgaaaagagc    180
tactccacat ctctgaaatc taggctgacc atcagtaagg atacaagtaa atcacaggtg    240
gtcctgacta tgaccaacat ggaccccgtg gatacagcaa cttactattg tgcccgggtg    300
gatcaggggt gggtcaatac ctattcagcc ttctattatg gaatggactt ctggggacag    360
gggactaccg tcaccgtctc ttca                                            384

<210> SEQ ID NO 88
<211> LENGTH: 321
<212> TYPE: DNA
<213> ORGANISM: Artificial Sequence
<220> FEATURE:
<223> OTHER INFORMATION: HMB2437 ANTIBODY FRAMEWORK REGIONS GERMLINED
      (FR-GL) VARIANTS light chain FR-GL nuc

<400> SEQUENCE: 88
gacatccaga tgacccagag ccctagctcc ctgtccgcat ctgtggggga tcgggtcacc     60
atcacatgca gagcctccca gtacatttct acacacctga actggtatca gcagaagccc    120
ggcaaagccc ctaagctgct gatctacgga gcttctagtc tgcagagtgg cgtgccctct    180
aggttcagtg gctcagggag cggaacagac tttactctga ccatttcaag cctgcagcca    240
gaggatttcg ctacttacta ttgtcagcag acatataaaa ctcccatcac ctttggccag    300
gggacccggc tggaaatcaa a                                              321
```